(12) United States Patent
Csordas et al.

(10) Patent No.: US 11,007,849 B2
(45) Date of Patent: May 18, 2021

(54) DETECTING RESIDUAL HOST CELL PROTEINS IN RECOMBINANT PROTEIN PREPARATIONS

(71) Applicants: MedImmune, LLC, Gaithersburg, MD (US); The Regents of the University of California, Santa Barbara, CA (US)

(72) Inventors: Andrew Csordas, Santa Barbara, CA (US); James B. McGivney IV, Gaithersburg, MD (US); Hyongsok Tom Soh, Santa Barbara, CA (US); Robert Strouse, Gaithersburg, MD (US); Faye Walker, Santa Barbara, CA (US)

(73) Assignees: MedImmune, LLC, Gaithersburg, MD (US); The Regents of the University of California, Santa Barbara, CA (US)

( * ) Notice: Subject to any disclaimer, the term of this patent is extended or adjusted under 35 U.S.C. 154(b) by 653 days.

(21) Appl. No.: 15/503,852

(22) PCT Filed: Aug. 14, 2015

(86) PCT No.: PCT/US2015/045221
§ 371 (c)(1),
(2) Date: Feb. 14, 2017

(87) PCT Pub. No.: WO2016/025804
PCT Pub. Date: Feb. 18, 2016

(65) Prior Publication Data
US 2017/0274734 A1    Sep. 28, 2017

Related U.S. Application Data

(60) Provisional application No. 62/154,981, filed on Apr. 30, 2015, provisional application No. 62/037,864, filed on Aug. 15, 2014.

(51) Int. Cl.
| | | |
|---|---|---|
| *A61K 48/00* | (2006.01) |
| *C07H 21/04* | (2006.01) |
| *B60H 1/26* | (2006.01) |
| *G01N 33/53* | (2006.01) |
| *G01N 33/68* | (2006.01) |
| *C12N 15/115* | (2010.01) |
| *B60J 7/16* | (2006.01) |
| *F04D 25/06* | (2006.01) |
| *F04D 25/14* | (2006.01) |

(52) U.S. Cl.
CPC ............ *B60H 1/262* (2013.01); *B60J 7/1642* (2013.01); *C12N 15/115* (2013.01); *F04D 25/0673* (2013.01); *F04D 25/14* (2013.01); *G01N 33/5308* (2013.01); *G01N 33/68* (2013.01); *C12N 2310/16* (2013.01)

(58) Field of Classification Search
CPC ... A61K 45/06; C12N 2310/16; C12N 15/115
See application file for complete search history.

(56) References Cited

U.S. PATENT DOCUMENTS

| | | | |
|---|---|---|---|
| 5,132,222 A | 7/1992 | Kanai et al. | |
| 2006/0205010 A1* | 9/2006 | Allioux ................... | C07K 1/22 435/7.1 |
| 2008/0261249 A1 | 10/2008 | Wang et al. | |
| 2009/0247421 A1 | 10/2009 | Boschetti et al. | |
| 2011/0250167 A1 | 10/2011 | Boschetti et al. | |
| 2012/0095200 A1* | 4/2012 | Brown .................. | C12N 15/111 536/23.1 |
| 2013/0059292 A1 | 3/2013 | Kim et al. | |
| 2013/0244891 A1* | 9/2013 | Waggoner ............ | G01N 33/533 506/9 |
| 2013/0344097 A1* | 12/2013 | Guo ................... | A61K 39/0011 424/185.1 |

FOREIGN PATENT DOCUMENTS

| | | |
|---|---|---|
| WO | WO 2004/094989 A2 | 4/2004 |
| WO | WO 2009/070749 A1 | 4/2009 |

OTHER PUBLICATIONS

Fortis et al., "A New Approach for the Detection and Indentification of Protein Impurities Using Combinatorial Solid Phase Ligand Libraries", Oct. 1, 2006, Journal of Proteome Research, vol. 5, No. 10, pp. 2577-2585.

Cho et al., "Quantitative selection and parallel characterization of aptainers", Nov. 12. 2013, PNAS, vol. 110, No. 46, pp. 18460-18465.

Supplementary Partial European Search Report for European Application EP 15832244 completed Dec. 1, 2017.

(Continued)

*Primary Examiner* — Amy H Bowman

(57) ABSTRACT

This application provides a method of using aptamers to determine the presence of HCP's in a recombinant protein preparation, and provides methods of preparing a plurality of aptamers for use in the method of detecting a plurality of HCP's in a recombinant protein preparation. In accordance with the description, a method of determining the presence or absence of a plurality of HCP's in a recombinant protein preparation comprises: providing a recombinant protein preparation; providing a final pool of aptamers; combining the recombinant protein preparation with the final pool of aptamers; and determining the presence or absence of a plurality of HCP's.

9 Claims, 4 Drawing Sheets

Specification includes a Sequence Listing.

(56) References Cited

OTHER PUBLICATIONS

International Search Report for PCT/US2015/045221 dated Dec. 14, 2015.
Boschetti et al., "The are of observing rare protein species in proteomes with peptide ligand libraries", Protemics, vol. 9, No. 6, Mar. 1, 2009, pp. 1492-1510.
Supplementary European Search Report for European Application EP 15832244 completed Mar. 1, 2018.

* cited by examiner

DETECTING RESIDUAL HOST CELL PROTEINS IN RECOMBINANT PROTEIN PREPARATIONS

CROSS-REFERENCE TO RELATED APPLICATIONS

This application is a U.S. National Stage application of International Application No. PCT/US2015/045221, filed on Aug. 14, 2015, said International Application No. PCT/US2015/045221 claims benefit under 35 U.S.C. § 119(e) of the U.S. Provisional Application No. 62/154,981, filed Apr. 30, 2015, and U.S. Provisional Application No. 62/037,864, filed Aug. 15, 2014. Each of the above listed applications is incorporated by reference herein in its entirety for all purposes.

REFERENCE TO THE SEQUENCE LISTING

This application incorporates by reference a Sequence Listing submitted with this application as text file entitled "HCP_600WO1_SL_2", created on Feb. 14, 2017, and having a size of 92.6 kilobytes.

This application claims priority to U.S. Provisional Patent Application No. 62/037,864, filed Aug. 15, 2014; and U.S. Provisional Patent Application No. 62/154,981, filed Apr. 30, 2015. The content of these applications is incorporated herein by reference in its entirety.

FIELD

This is in the recombinant protein field. More specifically, this pertains to methods of determining the presence of residual host cell proteins (HCPs) in recombinant protein preparations.

BACKGROUND

Recombinant proteins are typically produced in host cells. Host Cell Proteins (HCPs) are process-related impurities that arise from the host cells during the normal course of recombinant protein production [Wang et al., HCPs in Biologics Development: Identification, Quantitation and Risk Assessment, *Biotechnol. Bioeng.* 103(3):446-458 (2009)]. In recombinant biopharmaceuticals, HCPs carry potential clinical safety risks due to the activity of the HCPs themselves, or to the ability of the HCP to elicit an immune response. Indeed, demonstration of clearance and/or control of HCPs present in a biotherapeutic is a regulatory requirement [ICH Harmonised Tripartite Guideline Specifications: Test Procedures and Acceptance Criteria for Biotechnological/Biological Products Q6B (1999)]. Thus, the characterization, removal, and/or clearance of HCPs from recombinant biopharmaceuticals through the purification process are desirable before the biopharmaceutical may be released for use in treating humans or animals.

HCPs are currently detected in recombinant protein preparations using polyclonal antibodies (pAb) in an immunoassay format. The production of anti-HCP pAbs is time consuming and expensive, and there are significant quality and utility issues with the resulting anti-HCP pAbs: 1) Due to the immunization of animals, anti-HCP pAb production takes between 9-12 months at significant cost; 2) Recognition of all of the HCP s in a mixture is not possible due to either the lack of immunogenicity of some of the HCP in the animals used to generate the polyclonal immune response, or the low relative amounts of individual HCPs present in the HCP mixture used to immunize the animals.

A typical HCP pAb recognizes roughly 50-75% of HCPs in a recombinant protein preparation. With some estimates of 1,200 to 1,600 possible HCPs in an antigenic preparation, such an approach potentially leaves a great deal of HCPs undetectable by a pAb. Therefore, a better HCP detection reagent, one that recognizes all or nearly all potential HCPs, would be highly desirable to give better quantitative meaning to the HCP immunoassay results.

Aptamers have previously been generated against a single target (whether in purified form or as part of a complex mixture). When generating aptamers from a complex mixture, Fitter and James [Deconvolution of a Complex Target Using DNA Aptamers, *J. Cell Biol.*, 280 (40): 34193-34201 (2005)] teaches a serial processing strategy. In this strategy, Fitter and James use a target depletion strategy to avoid convergence of aptamers only to a few targets within the mixture. Specifically, in a serial processing strategy, Fitter and James perform repeated rounds of screening and after each round, they use the aptamers generated in the previous round to remove the targets from the mixture.

The method taught here is inherently a parallel strategy that does not require any depletion of targets. Specifically, the method presented herein uses next generation sequencing (NGS) to identify aptamers for binding to all targets in the mixture in parallel, and uses the aptamer arrays to measure the actual binding simultaneously of all aptamers to all targets in the mixture. It was not previously perceived possible to accomplish such a complex task. Specifically, it was not previously perceived possible to use a parallel strategy to identify aptamers binding to different targets and to decouple the identity of the aptamers and their ability to bind to each target. The pool of aptamers obtained here may be used for determining the presence of HCPs in recombinant protein preparations.

SUMMARY

In accordance with the description, a method of determining the presence or absence of a plurality of HCPs in a recombinant protein preparation comprises: providing a recombinant protein preparation; providing a final pool of aptamers; combining the recombinant protein preparation with the final pool of aptamers; and determining the presence or absence of a plurality of HCPs.

In some embodiments, the recombinant protein preparation is a biopharmaceutical preparation.

In one embodiment, determining the presence of a plurality of HCPs comprises microarray, chromatography, polymerase chain reaction, or enzyme-linked immunosorbent assay. In another embodiment, the final pool of aptamers has been chosen for the ability of the individual aptamers to bind HCPs.

One embodiment encompasses a method of preparing a final pool of aptamers for use in detecting or removing a plurality of HCPs in a recombinant protein preparation, where the method comprises: providing a library of potential aptamers; selecting a plurality of candidate aptamers from the library of potential aptamers by exposing the library of potential aptamers to an HCP mixture comprising a plurality of HCPs, and separating a plurality of candidate aptamers from the library of potential aptamers by the ability of each individual aptamer to bind to one HCP; and determining the identity of a plurality of aptamers binding a plurality of HCPs, wherein the method identifies a final pool of aptamers that specifically bind HCPs.

In an embodiment, the recombinant protein preparation is from a host cell transiently expressing the recombinant protein. In another embodiment, the recombinant protein preparation is from a stably transformed host cell. In another embodiment, the pool of candidate aptamers is the final pool of aptamers. In one embodiment, the pool of candidate aptamers undergoes additional selection before selection of the final pool of aptamers. In some embodiments, the pool of candidate aptamers undergoes one or more rounds of selection to obtain a final pool of aptamers.

In a further embodiment, the method comprises determining the identity of a final pool of aptamers that bind specific HCPs. In one mode, determining the identity of a final pool of aptamers comprises sequencing the final pool of aptamers. In another aspect, sequencing comprises sequencing the final pool of aptamers in parallel. In one embodiment, sequencing in parallel is performed using a next generation sequencing process.

In an additional embodiment, the method comprises determining the identity of a plurality of HCPs binding the aptamers. In a further aspect, determining the binding affinity of the plurality of candidate aptamers for the HCPs in the recombinant protein preparation comprises: affixing the candidate aptamers to a solid support, contacting the recombinant protein preparation with the candidate aptamers bound to the solid support, and determining binding affinity of the HCPs in the recombinant protein preparation to the candidate aptamers or affixing the HCPs from the recombinant protein preparation to a solid support, contacting the candidate aptamers to the HCPs bound to the solid support, and determining the binding affinity of the candidate aptamers to the HCPs in the recombinant protein preparation.

In one mode, the candidate aptamers are bound to the solid support as an array. In another aspect, the binding affinity is determined in parallel for the candidate aptamers to the HCPs in the recombinant protein preparation using the array. In one embodiment, the recombinant protein preparation comprises a plurality of HCPs of unknown identity. In another embodiment, the recombinant protein preparation comprises a plurality of HCPs of unknown amount. In one mode, the recombinant protein preparation comprises different amounts of multiple HCPs. In another mode, the library of potential aptamers comprises at least about 10, at least about $10^2$, at least about $10^3$, at least about $10^4$, at least about $10^5$, at least about $10^6$, at least about $10^7$, at least about $10^8$, at least about $10^9$, at least about $10^{10}$, or at least about $6 \times 10^{14}$ aptamers.

In one mode, selecting a plurality of candidate aptamers from the library of potential aptamers comprises displaying a library of potential aptamers on a solid support. In one mode, each solid support displays multiple copies of the same aptamer. In a mode, each solid support displays multiple aptamers. In another aspect, the solid support and the aptamers form an aptamer particle. In an embodiment, the method comprises isolating the aptamers with an ability to bind HCPs. In one aspect, fluorescence-activated cell sorting (FACS) is used to isolate aptamers with an ability to bind to HCPs in the recombinant protein preparation. In another aspect, selecting a plurality of candidate aptamers from a library of potential aptamers comprises microfluidic selection.

In a further mode, the solid support used to select candidate aptamers from the library of potential aptamers are beads. In another mode, the beads are magnetic beads. In one embodiment, HCPs are bound to the solid support. In some embodiments, the solid support to which the HCPs are bound are beads. In another embodiment, the beads are trapped in a micro-magnetic separation device. In another embodiment, multiple rounds of selection are performed to select a plurality of candidate aptamers from the aptamer library. In a further embodiment, the selection conditions in the multiple rounds of selection are different. In a different embodiment the selection conditions in the multiple rounds of selection are the same.

In one aspect, the nucleic acid sequence of only the final pool of aptamers is obtained. In another aspect, the nucleic acid sequence of aptamers at different steps in the selection is obtained. In a further aspect, after obtaining the nucleic acid sequence of the aptamers in a library of potential aptamers, an additional discrimination step identifies candidate aptamers for an array on which the candidate aptamers may be bound to determine affinity for HCPs. In one mode, the additional discrimination step comprises at least one of enrichment fold analysis, repeating motif analysis, and copy number analysis.

In one mode, the array is used to determine the binding affinity for at least about 10 aptamers to HCPs. In another mode, the array determines the binding affinity for at least about 10, at least about 100, at least about 150, at least about 200, at least about 250, at least about 300, at least about 250, at least about 300, at least about 500, at least about 1000, at least about 2000, at least about 5000, at least about 10,000, at least about 20,000, at least about $10^5$, at least about $10^6$, at least about $10^7$, at least about $10^8$, at least about $10^9$, at least about $10^{10}$, or at least about $6 \times 10^{14}$ aptamers to HCPs. In another mode, aptamers are attached to a solid support using a linker. In another mode, the binding affinity for the aptamers to HCPs is determined by measuring $K_D$ or $K_A$. In another mode, aptamers bind specific HCPs with a $K_D$ of at least about 2 µM.

In one aspect, the method generates at least about 10, at least about 20, at least about 200, at least about 300, at least about 400, at least about 500, at least about 600, at least about 700, at least about 800, at least about 900, at least about 1000, or at least about $6 \times 10^{14}$ aptamers that bind specific HCPs. In one embodiment, the aptamers are used to determine the presence of HCPs in a recombinant protein preparation. In another embodiment, aptamers are used to determine the identity of HCPs in a recombinant protein preparation. In an embodiment, aptamers are used to determine the amount of HCPs in a recombinant protein preparation.

Another mode encompasses a method of determining the identity of at least one HCP in a recombinant protein preparation comprising: providing at least one aptamer prepared by the methods herein; and determining the identity of at least one HCP.

In one aspect, the method employs a plurality of aptamers. In another aspect, the identity of at least one HCP is determined by mass spectrometry.

Another mode encompasses a method of detecting the presence of a plurality of HCPs in a recombinant protein preparation comprising: providing a final aptamer pool prepared by the methods herein; and determining whether some of the aptamers bind specific HCPs in the recombinant protein preparation.

Another mode encompasses a method of removing HCPs from a recombinant protein preparation comprising: providing a final pool of aptamers prepared by the methods herein; exposing the recombinant protein preparation comprising HCPs to the final pool of aptamers, allowing the aptamers to bind HCPs; and separating the HCPs binding aptamers from the recombinant protein preparation. In one aspect, the final pool of aptamers is affixed to a solid support. In one mode, the solid support is a plate, chromatography resin, or a bead. In an aspect the bead is a magnetic bead. In another mode, each of the aptamers in the final pool of aptamers is individually affixed to a solid support. In another aspect, all of the aptamers in the final pool of aptamers are affixed as a mixture to the solid support.

The embodiments can be more fully understood from the following detailed description and the accompanying drawings, which form part of this application.

DESCRIPTION OF THE SEQUENCES

Figure 1:
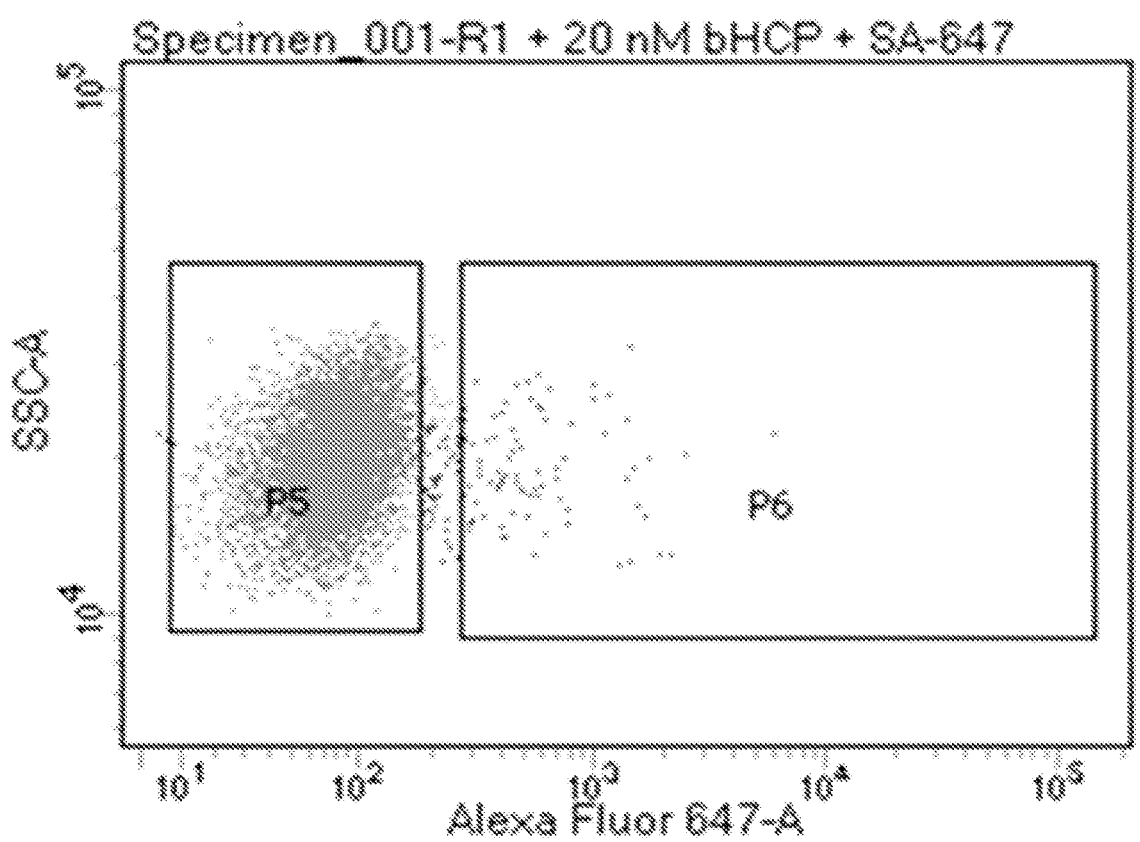
FIG. 1 depicts a FACS plot showing fluorescence intensity for individual aptamer particles bound to fluorescently labeled HCPs.

The table listed below provides the nucleic acid sequence, name or description, and sequence identifier number (SEQ ID NO) of primers, linkers, and aptamers referenced herein.

Table 1 contains SEQ ID NO: 1 to SEQ ID NO: 398, and provides a listing of sequences of primers and some of the aptamers referenced in present embodiments.

DETAILED DESCRIPTION

I. Definitions

In the context of this disclosure, a number of terms should be utilized.

In the present disclosure, "HCP" relates to Host Cell Protein.

As used herein "host cell protein mixture" and "HCP mixture" and "HCP antigen" are used interchangeably and refer to a mixture of HCPs obtained from a null host cell, i.e., a host cell not expressing a recombinant protein.

As used herein, a "recombinant protein preparation" refers to the preparation obtained after expressing a recombinant protein in a host cell. The recombinant protein preparation may be an antibody preparation. The recombinant protein preparation may be a biopharmaceutical preparation.

The term "aptamer" refers to an oligonucleic acid or peptide molecule that binds to a specific target molecule. Oligonucleotide aptamers may be classified as DNA, RNA, or xeno nucleic acid (XNA) aptamers, and usually consist of short strands of oligonucleotides or XNA. Peptide aptamers consist of a short variable peptide domain attached at both ends to a protein scaffold.

The term "potential aptamers" refers to a collection of aptamers that may be provided at the beginning of a method to identify aptamers to be used for the detection of HCPs. The potential aptamers may be randomly generated. The potential aptamers may be a library of potential aptamers.

"Candidate aptamers" are aptamers that have undergone some selection for binding to HCPs and are thus a subset of the potential aptamers.

Used interchangeably herein are "final pool of aptamers" and "final aptamer pool" which refer to the collection of aptamers prepared and identified to be used in the method of determining the presence of a plurality of HCPs in a recombinant protein preparation. The final pool of aptamers may be a subset of the candidate aptamers having undergone additional selection or may be the candidate aptamers. The final pool of aptamers is a plurality of aptamers.

The term "plurality of aptamers" refers in the instant application to at least about at least about 10, at least about $10^2$, at least about $10^3$, at least about $10^4$, at least about $10^5$, at least about $10^6$, at least about $10^7$, at least about $10^8$, at least about $10^9$, at least about $10^{10}$, or at least about $6 \times 10^{14}$ aptamers.

The term "anti-HCP aptamer" refers to an aptamer that has been prepared by the methods described herein and specifically binds to one HCP.

The term "microfluidics" refers to a system in which small volumes of fluid will be handled, with at least one dimension below about 1000 µm or below about 500 µm.

As used herein, the term "about" refers to a numeric value, including, for example, whole numbers, fractions, and percentages, whether or not explicitly indicated. The term about generally refers to a range of numerical values (e.g., +/−5-10% of the recited range) that one of ordinary skill in the art would consider equivalent to the recited value (e.g., having the same function or result). In some instances, the term about may include numerical values that are rounded to the nearest significant figure.

The amount of each HCP may be determined by concentration or quantity of the protein.

II. Producing Aptamers to HCPs

Aptamers may be used for the detection of HCPs. Because aptamer generation is not dependent on immune recognition, methods using aptamers have the potential to detect a greater number of HCPs than current methods.

In one embodiment, aptamers may be selected for determining the presence of HCPs in a recombinant protein preparation obtained from any one of the different cell types known (including, but not limited to, mammalian, bacterial, yeast, insect, or plant).

The present disclosure encompasses a plurality of approaches to producing a plurality of aptamers that bind specific HCPs. In one embodiment, a method of preparing a plurality of aptamers comprises the following steps. First, a library of potential aptamers is provided. Second, candidate aptamers may be selected from the library of potential aptamer by determining which candidate aptamer(s) show some degree of binding to HCPs. In such a method, the steps identify a plurality of aptamers that bind specific HCPs. In one method, the candidate aptamers may be the final pool of aptamers. In some embodiments, the aptamers may be for use in a method of detection or a method of removal of HCPs.

In another embodiment, the approach comprises the following steps. First, a library of potential aptamers is provided. Second, candidate aptamers may be selected from the library of potential aptamers by determining which aptamers show some degree of binding to HCPs. Third, the method may comprise determining the identity of (i) a plurality of aptamers binding a HCP and/or (ii) a plurality of HCPs binding the plurality of aptamers. In one embodiment, determining the identity of a plurality of aptamers comprises sequencing the aptamers. In one embodiment, the sequencing the aptamers is conducted in parallel. In one embodiment, the sequencing in parallel is conducted through a next-generation sequencing process.

In one embodiment, the pool of candidate aptamers undergoes additional selection before the preparation of the final pool of aptamers. In another embodiment, the approach comprises the following steps. First, a library of potential aptamers is provided. Second, candidate aptamers may be selected from the library of potential aptamers by determining which aptamers show at least some degree of binding to HCPs in an HCP mixture. Third, those candidate aptamers showing some degree of binding to HCPs in an HCP mixture may be sequenced. In some embodiments, the sequencing is performed in parallel. Fourth, the binding affinity for a plurality of the candidate aptamers may be specifically determined. Fifth, a final aptamer pool may be identified based on the binding affinity of the candidate aptamers to the HCPs in the HCP mixture, or the recombinant protein preparation. In one embodiment, the binding affinity may be specifically determined by employing a solid support displaying candidate aptamers. In one embodiment, the solid support may be an array. In an embodiment where the solid support is an array, the binding affinity for the candidate aptamers may be determined in parallel.

In another embodiment, the approach comprises the following steps. First, a library of potential aptamers is provided. Second, candidate aptamers may be selected from the library by determining which aptamers show some degree of binding to HCPs in an HCP mixture or a recombinant protein preparation. Third, those candidate aptamers showing some degree of binding to HCPs may be sequenced. In some embodiments the sequencing may be performed in parallel. Fourth, an array displaying the candidate aptamers may be provided. Fifth, the binding affinity for the candidate aptamers to the HCPs in the HCP mixture or the recombinant protein preparation may be determined using an array-based approach, and aptamers showing binding of less than 2 µM $K_D$ or less than 1 µM $K_D$ to the HCPs in the HCP mixture or the recombinant protein preparation may be chosen. Sixth, a plurality of aptamers that bind to specific HCPs in the HCP mixture or the recombinant protein preparation may be identified. In some embodiments, mutagenesis, or other forms of direct evolution may be used in the quest to identify aptamers that bind to specific HCPs.

The term "specifically binding" refers to the interaction of a binding molecule (here an aptamer) and its binding partner (here a HCP) where the interaction is dependent on the presence of a particular structure on the binding partner. The aptamer will preferentially bind or recognize the HCP even when the HCP is present in a mixture of other molecules (including other HCPs or the recombinant protein produced by a cell line of the same type).

In one embodiment, HCPs generated by a specific recombinant protein may be identified by determining the HCPs in a recombinant protein preparation; determining the HCPs in a protein preparation from a cell line of the same type, but not expressing the recombinant protein (null cell line); and subtracting the HCPs in the recombinant protein preparation from the HCPs in the null cell line.

Optionally, the final pool of aptamers may be used to determine the identity of the HCPs to which each aptamer binds. In some embodiments, the identified HCP may be isolated.

The affinity between some or all of the aptamers in the final aptamer pool generated through an embodiment described herein, and the HCP to which each aptamer most closely binds (i.e., has the lowest $K_D$) may be represented by a $K_D$ from about $1 \times 10^{-8}$ to about $1 \times 10^{-13}$. In another embodiment, it may be represented by a $K_D$ from about $1 \times 10^{-9}$ to about $1 \times 10^{-12}$ or from about $1 \times 10^{-9}$ to about $500 \times 10^{-12}$. In a recombinant protein preparation there are approximately 1,200 HCPs present at a concentration range of about 1 to 100 ng/mL. Thus, in order to see a signal with a scanner, the aptamers should have a $K_D$ from about $1 \times 10^{-8}$ to about $1 \times 10^{-13}$. In another embodiment, it may be represented by a $K_D$ from about $1 \times 10^{-9}$ to about $1 \times 10^{-12}$ or from about $1 \times 10^{-9}$ to about $500 \times 10^{-12}$.

In one embodiment, the HCPs are present in different amounts in the HCP mixture or in the recombinant protein preparation. Some HCPs may be present at very high concentrations and other HCPs may be present at very low concentrations. For example, the HCPs may differ in amount by at least about a 1:10 ratio, at least about a 1:100 ratio, or at least about a 1:1000 ratio. One advantage of the present methods is that this aptamer approach can be used to prepare aptamers or detect HCPs present at both high and low concentrations simultaneously.

A. Providing a Library of Potential Aptamers

The potential aptamers in a library may comprise nucleic acids. In one embodiment, the potential aptamers in a library may comprise DNA, or RNA, or XNA, or a combination thereof. In one embodiment, the potential aptamers in a library may comprise ssDNA. In a further embodiment, the potential aptamers in the library comprise randomized nucleotide sequences. In one embodiment, the potential aptamers also comprise polymerase chain reaction (PCR) primer sites. In one embodiment, the potential aptamer comprises about 100 nucleotides. In one embodiment the potential aptamer comprises about 50, about 60, about 70, about 80, about 90, about 100, about 110, about 120, or about 130 nucleotides. In one embodiment, the potential aptamer comprises from about 50 to about 130 nucleotides, from about 60 to about 120 nucleotides, from about 90 to about 110 nucleotides. In some embodiments, the aptamer library contains potential aptamers with the same number of nucleotides. In another embodiment, the library contains potential aptamers with different numbers of nucleotides. In one embodiment, different amounts of random sequences in the aptamers accounts for the different numbers of nucleotides in the potential aptamers. In some embodiments, the aptamers used to identify HCP in a CHO lysate contain 50 nucleotides.

In one embodiment, the potential aptamer comprises a random sequence of about 60 nucleotides. In one embodiment, the potential aptamer comprises a random sequence of from about 30 to about 100, from about 40 to about 90 nucleotides, or from about 50 to 70 nucleotides. In one embodiment, the potential aptamer comprises a random sequence of about 30, about 40, about 50, about 60, about 70, about 80, about 90, or about 100 nucleotides.

In another embodiment, the potential aptamer comprises PCR primer sites each of about 20 nucleotides. In one embodiment, the potential aptamer comprises PCR primer sites each from about 15 to about 25 nucleotides, or from about 18 to about 22 nucleotides. In one embodiment, the PCR primer sites are each about 15, about 18, about 19, about 20, about 21, about 22, or about 25 nucleotides.

In one embodiment, the potential aptamer comprises about 60 nucleotides in a randomized sequence flanked by PCR primer sites of about 20 nucleotides each arranged as 5'-primer site-randomized sequence-primer site-3'. In one embodiment, the PCR primer sites may be AGCAGCACAGAGGTCAGATG (set forth in SEQ ID NO: 1) and CCTATGCGTGCTACCGTGAA (set forth in SEQ ID NO: 2). Other PCR primer sites may also be used. Aptamer libraries and primers may be synthesized using phosphoramidite chemistry. Aptamer libraries and primers may be purchased at least from Integrated DNA Technologies.

In one embodiment, the library of potential aptamers comprises displaying the library of potential aptamers on a support. In one embodiment, each support displays multiple copies of the same aptamer. In an embodiment, each support displays multiple aptamers.

In one embodiment, the aptamers may be used in their native state (i.e. solution-phase state). In another embodiment, the aptamers may be formed into aptamer particles on a bead. In some embodiments, the aptamer particles are on a magnetic bead. In one embodiment, aptamer particles may be synthesized using emulsion polymerase chain reaction (PCR). In one embodiment water-in-oil emulsions may be prepared with PCR reagents, such that each droplet contains (in most cases) one DNA template and one bead (such as, for instance, a magnetic bead) coated with forward primer. PCR amplification may be performed within the droplet, yielding particles that display multiple copies of the aptamer on their surface. In one embodiment, the particle may display about $2.4 \times 10^5$ copies of the aptamer [Wang et al., Particle Display: A Quantitative Screening Method for Generating High-Affinity Aptamers, *Angew. Chem.* 53(19): 4796-4801 (2014)]. After breaking the emulsion and removing unreacted PCR reagents, the aptamer complement strands may be denatured and released by treatment with NaOH and the aptamer particles collected. If a magnetic bead was employed, the aptamer particles may be collected in subsequent steps by magnetic separation. In some embodiments, a bead may be used that is not magnetic.

B. Selecting Candidate Aptamers from a Library

A variety of techniques may be used to select a plurality of candidate aptamers from a library. In one embodiment, a plurality of candidate aptamers are selected from the library by exposing the library to a plurality of host proteins and separating a plurality of candidate aptamers from the library for their ability to each bind to at least one of the HCPs. In one embodiment, any technique used to select candidate aptamers from a library and for binding aptamers to a known target may be used in this portion of the method. Thus, description of particular methods of selecting candidate aptamers from a library does not limit this particular portion of the method.

In one embodiment, each of the candidate aptamers is selected for its high-affinity binding to only one HCP. In one embodiment, the candidate aptamers will have a $K_D$ of about 2 µM or lower for its target HCP. In another embodiment, the candidate aptamer will have a $K_D$ of from about 1 nM to about 25 nM or lower for its target HCP. In one embodiment, each of the candidate aptamers is sorted by its affinity for only one HCP. In one embodiment, at least about 10, at least about $10^2$, at least about $10^3$, at least about $10^4$, about $10^5$, about $10^6$, about $10^7$, about $10^8$, about $10^9$, or about $10^{10}$ candidate aptamers are identified by this process. A large number of different sequences may be synthesized in parallel on an array, cleaved off, and collected, making the generation of aptamer mixtures a very simple process.

In one embodiment, the candidate aptamers are the final pool of aptamers. In another embodiment, the candidate aptamers undergo additional selection before the composition of a final pool of aptamers is determined. There are a range of methods for selecting candidate aptamers from a library, with some described as follows:

1. Microfluidic Selection Platform

In one embodiment, aptamers may be generated through systematic evolution of ligands by exponential enrichment using microfluidics technology. In one embodiment, microfluidic selection begins by immobilizing HCPs on the surface of magnetic beads that may be micron sized. The coated beads may be incubated with a nucleic acid library, as discussed above.

During incubation, aptamers that bind the HCPs will bind to the HCP-coated beads. The beads can be washed and sorted using a variety of modes. In one embodiment, the beads are magnetic and are subject to high-stringency continuous washing at a flow rate of 50 mL/hour within a micromagnetic separation device (MMS). After the separation, the external magnets may be removed, the beads carrying the selected aptamers eluted, and aptamers amplified. Amplification of aptamers may be performed by polymerase chain reaction (PCR) to obtain double stranded DNA (dsDNA), which may be denatured into ssDNA for use in additional rounds of selection.

In one embodiment, the molar ratio between aptamer ssDNA and target may be at least about 1:1, about 5:1, about 10:1, about 25:1, about 50:1, about 75:1, about 100:1, about 200:1, about 500:1, with the higher ratios of aptamer ssDNA to target increasing the selection pressure on the process.

In some embodiments, a negative selection component may also be added by binding other molecules to the beads to increase the specificity of the selected aptamers. In one embodiment, the recombinant protein produced by the host cell may be used. In one embodiment, when a negative selection mode is used, the negative selection may occur before the positive selection using the depleted pool. In another embodiment, the negative selection may occur after the positive selection. Negative selection allows for removal of potential aptamers in the library that would bind to the recombinant protein that is being produced by the host cell in question.

In one embodiment, multiple rounds of selection may be used and the data compared between them. When multiple rounds of selection are used, the conditions in each round may be the same or may differ. For example, multiple rounds of selection may be used and candidate aptamers appearing in all of the rounds of selection favored more highly in the overall selection process. Alternatively, different conditions may be used in order to balance the stringency of the process with number of aptamers selected as candidate aptamers. Furthermore, microfluidic selection can also be combined with particle display selection, with different techniques used in different rounds and candidate aptamers being those that are selected through both processes. In one embodiment, from about 1 to about 4 rounds of microfluidic selection and from about 1 to about 4 rounds of particle display are used. In one embodiment, at least about 2, at least about 3, at least about 4, at least about 5, or at least about 6 total rounds of selection are used to determine the candidate aptamers.

2. Particle Display Method

If the aptamer library is provided on aptamer particles, in one embodiment, a particle display method may be used. In such a method, particles displaying aptamers are exposed to a plurality of HCPs and a plurality of candidate aptamer particles are selected for their ability to each bind to only one of HCPs. In one embodiment, the aptamers are sorted by their affinity for one HCP after their affinity has been measured.

In one embodiment, a plurality of HCPs is labeled with fluorescent moieties. FACS analysis may then be used to separate aptamer particles with higher affinity to one of the HCPs from aptamer particles with lower affinity to one of the HCP. In one embodiment, a single fluorescent label may be applied to the mixture of HCPs, labeling all of the proteins in a single step with a single fluorescent label as this method does not require differentiating which of the HCPs is binding.

Fluorescence intensity from proteins captured by the aptamer particles is proportional to the binding affinity of the aptamer to its target HCP. The direct correlation between fluorescence and aptamer affinity enables quantitative identification and sorting of the candidate aptamers with the highest affinities to HCPs.

Fluorescent labels that may be used in FACS analysis include, but are not limited to, fluorophores such as 7-AAD, Alexa Fluor® 405, Alexa Fluor® 488, Alexa Fluor® 532, Alexa Fluor® 546, Alexa Fluor® 647, Alexa Fluor® 700, APC (allophycocyanin), APC-Alexa Fluor® 750, APC-eFluor® 780, Cy5, eFluor® 450, eFluor® 605NC, eFluor® 625NC, eFluor® 650NC, eFluor® 660, FITC (fluorescein isothiocyanate), Fluorescein, Pacific Blue™, Pacific Orange, PE-Cyanine 5, PE-Cyanine 5.5, PE-Cyanine 5.5, PE-Cyanine 7, PE-eFluor® 610, PerCP-Cyanine 5.5, PerCP-eFluor® 710, Propidium Iodide (PI), R-PE (R-Phycoerythrin), RPE, RPE-Alexa Fluor® 610, RPE-Alexa Fluor® 700, RPE-Cy® 5.5, RPE-Cy® 7, RPE-Texas Red®, and TRI-COLOR®. Fluorescent labels also include quantum dots that may also be used in FACS analysis in place of traditional fluorophores. Quantum dots include, but are not limited to, Qdot® 525 nanocrystal, Qdot® 565 nanocrystal, Qdot® 585 nanocrystal, Qdot® 605 nanocrystal, Qdot® 655 nanocrystal, Qdot® 705 nanocrystal, Qdot® 800 nanocrystal (all from Life Technologies).

In one aspect, fluorescent labels may be attached to the HCPs through a biotin-streptavidin strategy. The HCPs may be biotinylated and the fluorescent protein conjugated to streptavidin. In one mode, EZ-Link Micro NHS-PEO4-Biotinylation Kit (Pierce Biotechnology), which includes a polyethylene glycol (PEG) spacer to improve water solubility, may be used. Protein concentrations may be adjusted to 0.5 mg/mL with phosphate-buffered saline (PBS) prior to biotinylation. A 50-fold molar excess of biotin reagent to label 50-100 μg protein may be used for 30 minutes or longer at room temperature, and free biotin removed via Zeba Desalt Spin Column (Pierce Biotechnology). Biotinylated protein concentration may be measured based on absorbance at 280 nm using, for example, a NanoDrop spectrophotometer (Thermo Scientific).

In another embodiment, the fluorescent label may be attached to the HCP through any reaction that affixes the fluorophore to the HCP. For example, a chemically-reactive derivative of a fluorophore may be used to react with the HCP. Examples include, isothiocyanate derivatives, succinimidyl esters, maleimide-activate fluorophores, etc.

3. Combining Techniques

Any technique known in the art may be used to select aptamers from a library. In some embodiments, at least one of the techniques described herein may be used to select aptamers from a library. In one embodiment, multiple rounds of a single technique may be combined and/or multiple techniques may be combined in a multi-step process.

C. Optionally Determining the Identity of a Plurality of Aptamers Binding HCPs

Once candidate aptamers are chosen that demonstrate some level of binding to the HCPs in the HCP mixture or the recombinant protein preparation, the identity of the candidate aptamers chosen may be ascertained. In one embodiment, the identity of the aptamers is ascertained through a parallel sequencing process, such as a next generation sequencing process.

1. Next Generation Sequencing

Next generation sequencing means sequence determination using methods that determine many (typically thousands to billions) of nucleic acid sequences in an intrinsically parallel manner, i.e. where DNA templates are prepared for sequencing not one at a time, but in a bulk process, and where many sequences are read out preferably in parallel, or alternatively using an ultra-high throughput serial process that itself may be parallelized. Such methods include but are not limited to pyrosequencing (for example, as commercialized by 454 Life Sciences, Inc., Branford, Conn.); sequencing by ligation (for example, as commercialized in the SOLiD™ technology, Life Technology, Inc., Carlsbad, Calif.); sequencing by synthesis using modified nucleotides (such as commercialized in TruSeq™ and HiSeq™ technology by Illumina, Inc., San Diego, Calif., and PacBio RS by Pacific Biosciences of California, Inc., Menlo Park, Calif.), sequencing by ion detection technologies (Ion Torrent, Inc., South San Francisco, Calif.); sequencing of DNA nanoballs (Complete Genomics, Inc., Mountain View, Calif.); nanopore-based sequencing technologies (for example, as developed by Oxford Nanopore Technologies, LTD, Oxford, UK), and like highly parallelized sequencing methods.

Such next-generation sequencing methods can be carried out, for example, using a one pass sequencing method or using paired-end sequencing. Next generation sequencing methods include, but are not limited to, hybridization-based methods, sequencing-by-synthesis methods, ligation-based methods, nanopore sequencing, as well as other methods.

In one embodiment, sequencing is performed on the candidate aptamers from the selection process. In another embodiment, sequencing is performed on multiple pools of candidate aptamers from the selection process.

In one embodiment, PCR may be used to amplify the candidate aptamers from the selection process before sequencing.

2. Optional Additional Discrimination Steps Using Sequence Information

In one embodiment, an additional discrimination step using information from a sequencing process identifies a final pool of aptamers. The final pool of aptamers may be used for the determination of binding affinity. Techniques may be employed to group aptamers or to enrich aptamers that may bind to HCPs in lower concentration. Alternatively, techniques may be employed to differentiate aptamers binding with high affinity to their target HCP from aptamers with low affinity to their target HCP by comparing aptamer pools from different screening rounds.

Repeating motif analysis includes evaluating the sequences of the initial group of candidate aptamers to examine the heterogeneity of the selected population and to identify homologous sequences. If at least one motif is shown in whole or in part in multiple candidate aptamers, it may signify that those aptamers bind to the same HCP or related HCPs (such as HCPs with homologous structures). These aptamers may be grouped and tested to determine if they bind to the same or a related HCP. In one embodiment, the at least one motif shown in whole or in part in multiple candidate aptamers may be located in the same or similar position (such as within 5, 10, or 15 nucleotides) within the candidate aptamer. In another embodiment, the at least one motif may be located in variable locations within the candidate aptamer.

In one embodiment, copy number analysis includes a process where aptamers may be rank-ordered based on their copy number and this information used to evaluate the aptamers. For instance, aptamers with a high copy number may bind to HCPs at a higher concentration, and aptamers with a lower copy number may bind to HCPs at a lower concentration. Having such information assists the investigator in evaluating the aptamers and selecting either a final pool of aptamers or selecting candidate aptamers for additional screening. In one embodiment, copy number analysis may be performed on the final pool of aptamers. In another embodiment, copy number analysis may be performed on multiple pools of candidate aptamers during the selection of a final pool of aptamers.

In one embodiment, enrichment fold analysis includes determining the copy number of each aptamer in each of multiple pools of candidate aptamers during the selection of a final pool of aptamers and ranking the aptamers by the ratio of the copy numbers between two selection rounds for every aptamer. Those aptamers that become enriched during selection (i.e. those that have a higher copy number for a later round of selection than they do for an earlier round of selection) are likely to be more meaningful aptamers. For example, there may be aptamers with a high copy number in multiple pools of selection, but do not demonstrate any notable enrichment fold. In such a case, those aptamers might be overrepresented as a result of biases during library synthesis or PCR. For example, if three pools of selection were obtained, the copy number for round 3 could be compared to the copy number for round 1 (round 3/round 1). Alternatively, or in combination, the copy number for round 3 could be compared to the copy number for round 2 (round 3/round 2). Alternatively, or in combination with one or both of the preceding approaches, the copy number for round 2 could be compared to the copy number for round 1 (round 2/round 1). As a ratio is obtained for each aptamer, those aptamers demonstrating higher enrichment fold are likely to be more meaningful.

D. Optionally Determining the Identity of HCPs Binding the Aptamers

In one embodiment, the plurality of HCPs binding the aptamers, such as the candidate aptamers, may be determined. The identity of a HCP binding an aptamer (whether the identity of the aptamer is known or unknown) may be determined using any of the methods described below in Section II.G. The identity of HCPs binding to candidate aptamers may be determined as a part of characterizing a final pool of aptamers where the candidate aptamers are the final pool of aptamers. The identity of HCPs binding to candidate aptamers may be determined as part of a continuing selection process where additional steps are employed to further select a different final pool of aptamers.

E. Optionally Determining Binding Affinity for Candidate Aptamers to HCP Preparation Approaches may optionally be used to determine the binding affinity for each aptamer to one HCP in an HCP mixture or in a recombinant protein preparation. In any of the methods of determining binding affinity, either the candidate aptamers may be used or those aptamers that are chosen after a further screening, such as at least one of enrichment fold, repeating motif, and copy number analysis without changing the name of the aptamers as candidate aptamers. In one embodiment, sequence information of the candidate aptamers may be employed in this optional process.

In one aspect, determining the binding affinity of the plurality of candidate aptamers for HCPs in an HCP mixture or a recombinant protein preparation comprises affixing the candidate aptamers to a solid support, contacting the aptamers affixed to the solid support with an HCP mixture or a recombinant protein preparation, and determining binding of HCPs to candidate aptamers. In another embodiment, the method comprises affixing the HCP mixture or recombinant protein preparation to a solid support, contacting the HCP mixture or recombinant protein preparation with candidate aptamers, and determining binding of the candidate aptamers to the HCPs.

In one embodiment, an array may be prepared in order to determine the binding affinity for candidate aptamers to HCPs in the HCP mixture or recombinant protein preparation. In one embodiment, the method comprises determining in parallel the binding affinity for the candidate aptamers to the HCPs in the HCP mixture or recombinant protein preparation using the array.

In one embodiment, the binding affinity for the candidate aptamers is determined by measuring the $K_D$ or $K_A$ of the candidate aptamers for their target HCP. In another embodiment, the aptamers specifically bind the HCP with a $K_D$ of at least 2 μM. In a further embodiment, the method generates a plurality of aptamers that specifically bind their target HCP. In one embodiment, the method generates at least about 2, at least about 20, at least about 200, at least about 300, at least about 400, at least about 500, at least about 600, at least about 700, at least about 800, at least about 900, at least about 1000, or at least about $6\times10^{14}$ aptamers that specifically bind the HCPs.

1. Aptamer Chip Array

An aptamer chip may be prepared with at least one array with a plurality of features. In one embodiment, the array may be prepared by printing chemically modified single stranded oligonucleotide substrates onto the reactive surface of an array chip. In one embodiment, the aptamer chip may be commercially sourced from Agilent Technologies (Santa Clara, Calif.), MYcroarray, or another vendor. In one embodiment, the aptamer chip may contain more than one array. In one embodiment, each array incorporates the aptamers for which binding affinity data is desired. The array may optionally incorporate control polynucleotides with random sequences. In another embodiment, each aptamer may be represented by two, three, or more than three copies to enable duplicate, triplicate, etc. measurement.

The candidate aptamers may be applied to the array either with the forward and/or reverse primer-binding regions from the library of potential aptamers or without the forward and/or reverse primer-binding regions from the library of potential aptamers. In one embodiment, the primer binding regions may be excised because the array cannot or does not optimally accommodate polynucleotides that are the length of the randomized portion of the candidate aptamer plus the primer portion. In another embodiment, the primer binding regions may be excised in order to confirm that the aptamers retain their function without these regions.

Linkers may be used to attach the candidate aptamers to the array surface. In one embodiment, a linker may be from about 10 to about 50 nucleotides, or from about 30 to about 45 nucleotides. In one embodiment, the linker may be about 40 nucleotides. In one embodiment, a poly-T linker may be used to attach the candidate aptamers to the array surface, such as an about 40 nucleotide poly-T linker. In another embodiment, a poly-A linker may be used to attach the candidate aptamers to the array surface, such as an about 40 nucleotide poly-A linker. In another embodiment, the linker may comprise a reverse primer. In an embodiment, the linker may comprise both, a forward and a reverse primer. The linkers for attachment to the solid surface may be the same or different than the PCR primers used above. For instance, a reverse primer strategy might comprise $X_{1-i}$-CC-TATGCGTGCTACCGTGAA (set forth in SEQ ID NO: 3), and a forward and reverse primer strategy might comprise AGGTCAGATG-$X_{1-i}$-CCTATGCGTG (set forth in SEQ ID NO: 4), wherein X represents any nucleotide and i is an integer to represent the number of nucleotides in the candidate aptamer. In the examples below, the candidate aptamers contain 50 nucleotides.

Once the array has been prepared, it is incubated with fluorescently labeled HCPs. In one embodiment, the array is divided into multiple identical arrays, which then may be incubated with the same concentration of fluorescently labeled HCP or different concentrations of fluorescently labeled HCP. If different concentrations are used, this allows the fluorescent signal from every single aptamer feature at each different HCP concentration to construct a binding isotherm, allowing for derivation of $K_D$ values for every sequence simultaneously.

For instance, the array may be incubated with about 10, about 25, about 50, about 75, about 100, about 150, about 200, or about 500 nM of labeled HCP or with about 1 µM labeled HCP. In one embodiment, Alexa Fluor® 647-labeled HCP may be used. After washing and drying, an array scanner may be used to measure the fluorescence intensity from every feature. If each sequence is applied to the array in triplicate, the signals may be averaged in the process of calculating the $K_D$ values.

In one embodiment, a Langmuirian binding isotherm may be assumed and the following equation used: $Y=B_{max} \times X/(K_D)+X$), where Y is the net fluorescence intensity at each concentration, X is the concentration of fluorescently labeled HCP, and $B_{max}$ is the net fluorescence intensity at saturation. In one embodiment, any aptamer sequence with a $B_{max}$ that is less than double the background is discarded.

In one mode, the array determines the specific binding affinity for at least 50 candidate aptamers to their target HCPs. In another mode, the array determines the binding affinity for at least about 100, at least about 150, at least about 200, at least about 250, at least about 300, at least about 500, at least about 1000, at least about 2,000, at least about 5,000, at least about 10,000, at least about 20,000, at least about 50,000 or at least about 100,000 candidate aptamers to their target HCPs.

2. Bead-Based Fluorescence Binding Assay

The binding affinity for candidate aptamers to specific HCPs in an HCP mixture or a recombinant protein preparation may also be evaluated using a bead-based fluorescence binding assay. In one mode, different aptamers in the form of aptamer particles, each displaying an aptamer with a unique sequence, may be incubated with an HCP mixture or a recombinant protein preparation. Optionally, a non-binding forward primer-displaying particle may be used as a negative control in each measurement. This can provide the relative binding affinities of selected candidate aptamers.

The $K_D$ of each candidate aptamer may also be determined using a bead-based fluorescence binding assay. In one embodiment, the reactions may take place in PBSMCT buffer (HyClone DPBS, catalog number SH30264.01) supplemented with 0.01% Tween-20 and $MgCl_2$ to 1 mM or 1.5 mM. The appropriate buffer volume may be added to each 1.5 mL tube so that the final reaction volume would be 100 µL. Biotinylated HCP (bHCP) may be added to each tube in concentrations ranging from 0.5 nM to 500 nM in the presence of 0.2 mg/mL (final concentration) of salmon sperm DNA (Invitrogen). A negative control with no bHCP may also be used with each aptamer.

ssDNA aptamers (Integrated DNA Technologies) may be 5' end amino modified and conjugated to 1 µm COOH beads (Invitrogen). Before starting the experiment, the beads may be diluted 1:500 in PBSMCT buffer. One microliter of the 1:500 dilution may be added to each tube containing buffer and bHCP. Each tube may be vortexed for 3 seconds, and then placed on a rotator for 1 hour at room temperature.

Following the one hour incubation, the tubes may be briefly spun down, a magnetic rack used to separate the beads from the supernatant, and 100 µL of a 1:1000 dilution of the stock solution of a premium grade streptavidin phycoerythrin solution (SA-PE, Life Technologies) added to each tube. Following vortexing for 3 seconds, the tubes may be incubated on a rotator at room temperature for 15 minutes.

After the 15 minute incubation with SA-PE, the tubes may be briefly spun down and placed on a magnetic rack for 1 minute. The supernatant may be removed and beads re-suspended in 100 µL of PBSMCT buffer. The tubes containing the 100 µL solutions may be placed on ice while transporting them to make measurements with an Accuri C6 (Becton Dickinson) flow cytometer.

Background subtracted median FL-2 fluorescence values may be plotted as a function of biotinylated HCP concentration. The data may be fit with a non-linear regression equation using a one site specific binding model from GraphPad. An equilibrium dissociation binding constant ($K_D$) may thus be determined for each aptamer.

F. Optionally Addressing Large Excesses of Recombinant Protein

The aptamer array can also be used to screen aptamers that bind to HCPs specifically, even in the presence of large excess amounts of recombinant proteins (such as a recombinant antibody, for example IgG). By fluorophore labeling the HCPs with one color and the recombinant protein with another, it will be possible to identify sequences that possess affinity for the HCP target and not for the recombinant IgG, based on the level and wavelength of fluorescence emitted from a given feature.

Once aptamer sequences have been identified on the array, these individual sequences can be synthesized and tested using bead or plate-based assays to confirm that they bind to the HCPs. This optional step further addresses the specificity of the present methods.

This optional technique may be used alone or in combination with the negative selection process described above where potential aptamers binding to the recombinant protein are removed from the aptamer library before selection of candidate aptamers.

G. Determining the Presence and/or Identity of the HCP to Which One or More Aptamers Bind The methods may also include determining the identity of the HCP to which one or more aptamers bind.

A variety of techniques may be used to identify the specific HCP to which an aptamer binds (whether the sequence of the aptamer is known or unknown). These techniques may include protein mass spectrometry, electrospray ionization (ESI), matrix-assisted laser desorption/ionization (MALDI). Alternatively, proteins may be enzymatically digested into smaller peptides by using a protease (such as trypsin), introduced into the mass spectrometer, and identified by peptide mass fingerprinting or tandem mass spectrometry.

Other techniques useful in the identification of the specific HCP to which an aptamer binds include Western blot, immunoassay, isoelectric focusing, capillary electrophoresis, microchip based electrophoresis, Raman spectroscopy, proton NMR, and determination of a crystal structure through x-ray crystallography, among others.

III. Methods of Detection of HCPs Using Aptamers

In one embodiment, a method of determining the presence of a plurality of HCPs in a recombinant protein preparation comprises providing a recombinant protein preparation, providing a final pool of aptamers, combining the recombinant protein preparation with the final pool of aptamers; and determining the presence of a plurality of HCPs. In one embodiment, determining the presence of a plurality of HCPs comprises microarray, chromatography, polymerase chain reaction, or enzyme-linked immunosorbent assay. In one embodiment, the final pool of aptamers is chosen for the ability of each aptamer to bind one HCP. In another embodiment, the final pool of aptamers is chosen for the ability of each aptamer to bind its target HCP using the methods described in section I above.

In one embodiment, a method of determining the identity of at least one HCP in a recombinant protein preparation comprises providing at least one aptamer prepared by any one of the methods discussed in section I above; and determining the identity of at least one HCP as discussed in section II.G. In one embodiment, the method employs a plurality of aptamers. In one embodiment, the method determines the presence and/or the identity of a plurality of HCPs.

In one embodiment, the concentration of HCPs in an HCP mixture or a recombinant protein preparation may be determined using the methods described herein.

A. Assay Platforms

Aptamers may be used in a variety of assay platforms in order to detect HCPs, including, but not limited to, array-based detection (such as a microarray which would allow detection of a large number of HCPs at the same time), ELISA and ELISA-type methods (such as ALPHAlisa), surface plasmon resonance, immuno-affinity methods including, but not limited to, immunoprecipitation, blotting, affinity chromatography, microfluidic platforms (such as Gyros), and process analytical technologies.

B. Efficacy

Methods of detection of HCPs using aptamers are expected to detect the HCP more accurately. In one embodiment, the methods of HCP detection are able to identify at least about 50%, about 55%, about 60%, about 65%, about 70%, about 75%, about 80%, about 85%, about 90%, about 91%, about 92%, about 93%, about 94%, about 95%, about 96%, about 97%, about 98%, about 99%, about 99.5%, or about 99.9% of the HCP in a recombinant protein preparation. In another embodiment, the methods of detection are able to identify about 100% of the HCP in the recombinant protein preparation.

In one embodiment, a pool of aptamers may be prepared and attached to solid supports to prepare a pool of aptamer particles. An HCP mixture is allowed to come in contact with the pool of aptamer particles. HCPs that are not bound to the pool of aptamer particles, termed un-bound HCP fraction, can be collected. HCPs that are bound to the pool of aptamer particles, termed bound HCP fraction, can be collected following disruption of the HCP/aptamer particle pool interface. The un-bound HCP fraction may be compared to the bound HCP fraction using techniques such as a two-dimensional gel electrophoresis, Western blotting, and/or mass spectrometry.

IV. Methods of Removal of HCPs

Once an HCP has been identified in the recombinant protein preparation, a variety of modes may be used to remove the HCP from the preparation. In one embodiment, the method of removing HCPs from a recombinant protein preparation comprises providing a plurality of aptamers; exposing the recombinant protein preparation to the plurality of aptamers; allowing the aptamers to bind the HCPs; and separating the aptamers bound to the HCPs from the recombinant protein preparation. In one embodiment, the plurality of aptamers used in the method is affixed to a solid support. In one embodiment, the solid support is a plate, chromatography resin, or a bead (including magnetic bead).

In one embodiment, at least one aptamer, such as one produced according to the methods described herein, may be used to remove HCP from the recombinant protein product. The aptamer may be affixed to a solid support, such as a porous resin or bead (including magnetic bead), the recombinant protein product applied and allowed to incubate, and the recombinant protein product separated from the solid support-aptamer-HCP complex. For example, in one embodiment, at least one affinity column with at least one aptamer may be used to remove HCP.

In one embodiment, each individual aptamer of a plurality of aptamers is affixed to a solid surface so that each solid surface has a homogenous preparation of aptamers affixed to it. In another embodiment, the plurality of aptamers is applied as a mixture to a solid surface so that each solid surface has a heterogeneous mixture of aptamers affixed to it.

Alternative embodiments can also proceed without using the aptamers, such as for example using gene knockout or siRNA techniques to eliminate or reduce the expression of the HCP that one desires to eliminate or reduce from the recombinant protein preparation once it has been specifically identified as described in section II.G above. An HCP binding to an aptamer can be isolated using methods known in the art, and additional aptamers or antibodies may be created to bind to it for a potentially higher-affinity removal process, if desired. Either such aptamers or antibodies can be used in the methods of removal as described above.

Exemplary Methods

Embodiment 1: A method of determining the presence or absence of a plurality of Host Cell Proteins (HCPs) in a recombinant protein preparation comprising: providing a recombinant protein preparation; providing a plurality of aptamers; combining the recombinant protein preparation with the plurality of aptamers; and determining the presence or absence of the plurality of HCPs.

Embodiment 2: The method of embodiment 1, wherein determining the presence or absence of the plurality of HCPs comprises microarray, chromatography, polymerase chain reaction, or enzyme-linked immunosorbent assay.

Embodiment 3: The method of any one of embodiments 1-2, wherein the plurality of aptamers are candidate aptamers chosen for their ability to specifically bind to their HCP targets.

Embodiment 4: The method of any of the preceding embodiments wherein the recombinant protein preparation is a biopharmaceutical preparation.

Embodiment 5: A method of preparing a plurality of aptamers for use in a method of detecting or removing a plurality of HCPs from a recombinant protein preparation comprising: providing a library of potential aptamers; selecting a plurality of candidate aptamers from the library of potential aptamers by exposing the library of potential aptamers to an HCP mixture comprising a plurality of HCPs, and separating a plurality of candidate aptamers from the library for the ability of each candidate aptamer to bind to its HCP target; and optionally determining the identity of a plurality of candidate aptamers, each binding its HCP target in a plurality of HCPs; wherein the method identifies a plurality of candidate aptamers that specifically bind to their target HCP in the HCP mixture.

Embodiment 6: The method of embodiment 5, wherein the HCP mixture is from a null cell line.

Embodiment 7: The method of any one of embodiments 5 or 6, wherein the pool of candidate aptamers is the final pool of aptamers.

Embodiment 8: The method of any one of embodiments 5 or 6, wherein the pool of candidate aptamers undergoes additional selection before selection of the final pool of aptamers.

Embodiment 9: The method of any one of embodiments 5 to 8, wherein the method comprises determining the identity of a plurality of candidate aptamers binding HCPs.

Embodiment 10: The method of embodiment 9, wherein determining the identity of a plurality of candidate aptamers comprises sequencing the plurality of candidate aptamers.

Embodiment 11: The method of embodiment 10, wherein sequencing comprises sequencing the plurality of candidate aptamers in parallel.

Embodiment 12: The method of embodiment 11, wherein the sequencing in parallel is performed using a next generation sequencing process.

Embodiment 13: The method of any one of embodiments 5 to 12, wherein the method comprises confirming the presence or absence of an HCP suspected to be bound by a particular aptamer by determining the identity of the HCP.

Embodiment 14: The method of any one of embodiments 5 to 12, comprising determining the binding affinity of the plurality of candidate aptamers for the HCP mixture comprising: affixing the candidate aptamers to a solid support; contacting the candidate aptamers bound to the solid support with an HCP mixture; and determining binding affinity of the HCPs in the HCP mixture to the candidate aptamers bound to the solid support; or affixing the HCPs from the HCP mixture to a solid support; contacting the candidate aptamers to the HCPs bound to the solid support; and determining the binding affinity of the candidate aptamers to the HCPs in the HCP mixture.

Embodiment 15: The method of embodiment 14, comprising providing an array displaying the candidate aptamers.

Embodiment 16: The method of embodiment 15, comprising determining in parallel the binding affinity of the candidate aptamers to the HCPs in the HCP mixture using the array displaying the candidate aptamers.

Embodiment 17: The method of any one of embodiments 5 to 16, wherein the HCP mixture comprises a plurality of HCPs of unknown identity.

Embodiment 18: The method of any one of embodiments 5 to 17, wherein the HCP mixture comprises a plurality of HCPs of unknown amount.

Embodiment 19: The method of any one of embodiments 5 to 18, wherein the HCP mixture comprises different amounts of a plurality of HCPs.

Embodiment 20: The method of any one of embodiments 5 to 19, wherein the library of potential aptamers comprises at least about 10, at least about $10^2$, at least about $10^3$, at least about $10^4$, at least about $10^5$, at least about $10^6$, at least about $10^7$, at least about $10^8$, at least about $10^9$, at least about $10^{10}$, or at least about $6\times10^{14}$ aptamers.

Embodiment 21: The method of any one of embodiments 5 to 20, wherein selecting a plurality of candidate aptamers from the library of potential aptamers comprises displaying a library of potential aptamers on a solid support.

Embodiment 22: The method of embodiment 21, wherein each unit of the solid support displays multiple copies of the same aptamer.

Embodiment 23: The method of any one of embodiments 21 or 22, wherein the solid support and the aptamers form aptamer particles.

Embodiment 24: The method of embodiment 23, wherein the method comprises isolating aptamer particles comprising aptamers with an ability to specifically bind only one of the HCPs in the HCP mixture.

Embodiment 25: The method of any one of embodiments 23 or 24, wherein fluorescence-activated cell sorting (FACS) is used to isolate aptamer particles with an ability to bind one of the HCPs in the HCP mixture.

Embodiment 26: The method of any one of embodiments 21 to 25, wherein selecting a plurality of candidate aptamers from the library of potential aptamers comprises microfluidic selection.

Embodiment 27: The method of any one of embodiments 5 to 26, wherein HCPs bound to a solid support are used to select candidate aptamers from the library of potential aptamers.

Embodiment 28: The method of embodiment 27, wherein the solid support are beads.

Embodiment 29: The method of embodiment 28, wherein the beads are magnetic beads.

Embodiment 30: The method of embodiment 29, wherein the HCPs bound to a solid support are trapped in a micromagnetic separation device.

Embodiment 31: The method of any one of embodiments 5 to 30, wherein multiple rounds of selection from the library of potential aptamers are performed to select a plurality of candidate aptamers.

Embodiment 32: The method of embodiment 31, wherein the selection conditions in the multiple rounds of selection are different.

Embodiment 33: The method of embodiment 31, wherein the selection conditions in the multiple rounds of selection are the same.

Embodiment 34: The method of any one of embodiments 31 to 33, wherein only the aptamers in the final pool of aptamers are sequenced.

Embodiment 35: The method of any one of embodiments 31 to 33, wherein the aptamers in multiple rounds of candidate aptamers are sequenced.

Embodiment 36: The method of any one of embodiments 10 to 35, wherein an additional discrimination step after sequencing identifies a final pool of aptamers.

Embodiment 37: The method of embodiment 36, wherein the additional discrimination step comprises at least one of enrichment fold analysis, repeating motif analysis, and copy number analysis.

Embodiment 38: The method of any one of embodiments 15 to 37, wherein the binding affinity of candidate aptamers bound to an array id determined for at least about 10 candidate aptamers to their HCP target.

Embodiment 39: The method of embodiment 38, wherein candidate aptamers bound to an array are used to determine the binding affinity for at least about 10, at least about 100, about 150, about 200, about 250, about 300, about 250, about 300, about 500, about 1000, about 2000, about 5000, about 10,000, about 20,000, about 50,000 or about 100,000 candidate aptamers to specific HCP targets.

Embodiment 40: The method of any one of embodiments 14 to 39, wherein the candidate aptamers are attached to a solid support using a linker.

Embodiment 41: The method of any one of embodiments 14 to 40, wherein the binding affinity for the candidate aptamers to their target HCP is determined by measuring $K_D$ or $K_A$.

Embodiment 42: The method of embodiment 41, wherein at least one candidate aptamer specifically binds an HCP with a $K_D$ of at least about 2 µM.

Embodiment 43: The method of any one of embodiments 5 to 42, wherein the method generates at least about 10, about 20, about 200, about 300, about 400, about 500, about 600, about 700, about 800, about 900, about 1000, or about $6 \times 10^{14}$ aptamers that specifically bind their target HCPs.

Embodiment 44: The method of any one of embodiments 5 to 43, wherein the aptamers are used to determine the presence of HCPs in a recombinant protein preparation.

Embodiment 45: The method of any one of embodiments 5 to 43, wherein the aptamers are used to determine the identity of HCPs in a recombinant protein preparation.

Embodiment 46: The method of any one of embodiments 5 to 43, wherein the aptamers are used to determine the amount of HCPs in a recombinant protein preparation.

Embodiment 47: A method of determining the identity of at least one HCP in a recombinant protein preparation comprising: providing at least one aptamer prepared by the method of any one of embodiments 5 to 43; contacting the at least one aptamer with a recombinant protein preparation; and determining the identity of at least one HCP in the recombinant protein preparation.

Embodiment 48: The method of embodiment 47, wherein the method employs a plurality of aptamers.

Embodiment 49: The method of any one of embodiment 47 or 48, wherein the identity of at least one HCP is determined by the aptamer that binds the HCP.

Embodiment 50: A method of detecting the presence or absence of HCPs in a recombinant protein preparation comprising: providing at least one aptamer; and determining whether the at least one aptamer specifically binds to HCPs in the recombinant protein preparation.

Embodiment 51: The method of embodiment 50, wherein the at least one aptamer is prepared by the method of any one of embodiments 5 to 46.

Embodiment 52: The method of embodiment 50 or 51, wherein the method employs a plurality of aptamers.

Embodiment 53: A method of removing HCPs from a recombinant protein preparation comprising: providing a pool of aptamers; exposing the recombinant protein preparation to the pool of aptamers; allowing the pool of aptamers to bind HCPs forming HCP:aptamer complexes; and separating the HCP:aptamer complexes from the recombinant protein preparation.

Embodiment 54: The method of embodiment 53, wherein the pool of aptamers is a final pool of aptamers.

Embodiment 55: The method of embodiment 53, wherein the pool of aptamers comprises the aptamers having a nucleotide sequence as set forth in SEQ ID NO: 74 to SEQ ID NO: 398.

Embodiment 56: The method of any one of embodiments 53 to 55, wherein the pool of aptamers is prepared by the method of any one of embodiments 5 to 46.

Embodiment 57: The method of any one of embodiments 53 to 56, wherein the pool of aptamers are affixed to a solid support.

Embodiment 58: The method of embodiment 57, wherein the solid support is a plate, chromatography resin, or a bead.

Embodiment 59: The method of embodiment 58, wherein the bead is a magnetic bead.

Embodiment 60: The method of any one of embodiments 57 to 59, wherein the aptamers in the pool of aptamers are each individually affixed to a solid support.

Embodiment 61: The method of any one of embodiments 57 to 59, wherein the aptamers in the pool of aptamers are applied as a mixture to the solid support.

Reference will now be made in detail to the present exemplary embodiments, examples of which are illustrated in the accompanying drawings. Other embodiments will be apparent to those skilled in the art from consideration of the specification and practice disclosed herein. The embodiments are further explained in the following examples. These examples do not limit the scope of the claims, but merely serve to clarify certain embodiments. It is intended that the specification and examples be considered as exemplary only, with a true scope and spirit being indicated by the following claims.

EXAMPLES

Example 1. Overview of Approach

A parallel aptamer generation workflow was utilized, comprising selecting a plurality of candidate aptamers from a library of potential aptamers for their ability to bind to a single HCP in an HCP mixture; sequencing the candidate aptamers in parallel; and determining in parallel the relative binding affinity of the candidate aptamers to their target HCP in the HCP mixture to select the candidate aptamers. The identity of the HCP to which an aptamer binds may be identified by binding individual aptamers on beads to prepare aptamer particles, and incubating the aptamer particles in the presence of an HCP mixture for an appropriate amount of time. After washing away aptamer particles that did not bind HCPs, the bound aptamer particles are eluted and the HCP identified by mass spectrometry.

Microfluidics may be used as an aptamer selection method to quickly isolate aptamers having high affinity against a HCP targets that are attached to magnetic beads. Target-coated beads are incubated with a ssDNA library consisting of randomized sequences which comprise the potential aptamer pool. Some of the aptamers will specifically bind to HCPs, and a microfluidic device is used to capture the magnetic beads and efficiently wash any aptamers not bound to HCPs. Magnetic beads carrying the aptamers bound to HCPs are eluted from the microfluidic device. The end result is a pool of candidate aptamers.

Particle display selection is a powerful aptamer selection method that leverages particle display (PD), emulsion PCR, and fluorescence-based particle sorting to isolate aptamers with high affinity for specific HCPs from the potential aptamer library. One advantage of particle display selection lies in the power of PD: each bead (particle) is coated with multiple copies of an aptamer of one specific sequence, simplifying aptamer identification (for example, via DNA sequencing).

Example 2. Selecting a Plurality of Candidate Aptamers

A pool of candidate aptamers that specifically bound HCPs was isolated by using microfluidics to enrich a potential aptamer library for aptamers that bind HCPs. A single round of aptamer enrichment was performed prior to starting particle display screening in order to decrease the diversity of the starting pool of aptamer particles to a number of aptamer particles that could be sorted by FACS. To perform this enrichment, an HCP mixture was first covalently conjugated to N-hydroxysuccinimide (NHS) activated beads (Pierce Biotechnologies, Rockford, Ill.). Successful conjugation of the HCPs to the beads was verified using a NanoOrange® Protein Quantification Kit (Molecular Probes®, Eugene, Oreg.). Potential aptamers were denatured, mixed with the HCP-coated beads, and after washing off non-bound aptamers, the bound aptamers were eluted from the HCPs by heating the HCP-coated beads in 50 µL of water for 5 minutes at 95° C. This microfluidics anti-HCP aptamer pool was used as the starting point for particle display.

A) CHO HCP

A null CHO host cell line was grown using standard bioreactor conditions at the 50 L scale and harvested by continuous centrifugation. The resulting harvest was diafiltered into PBS, aliquoted and stored at −80° C. until needed. An HCP mixture was prepared from this cell harvest.

B) HCP Coated Beads to be Used in Microfluidics Screening

HCP-coupled beads were prepared according the instructions for Pierce NHS-activated magnetic beads (Thermo Scientific cat #88826; Thermo Scientific, Rockford, Ill.) with several modifications. Briefly, a three-fold excess of HCP over the bead-binding capacity was used to obtain a final concentration of 150 µg HCP/mg bead. Beads were washed once with ice-cold 1 mM HCl, combined with HCP in PBS, and incubated at 4° C. for four hours with end-over-end rotation. Beads were washed twice with 0.1 M glycine, incubated with 3 M ethanolamine for two hours at room temperature, and washed once with nanopure $H_2O$. After three washes in storage buffer (10 mM Tris with 0.01% Tween-20), beads were reconstituted in storage buffer to the original concentration of 10 mg/mL and stored at 4° C.

C) Single Round of Aptamer Enrichment

A single round of aptamer enrichment proceeded as follows. One nmole ($6 \times 10^{14}$) of a ssDNA library was heated to 95° C. for 5 minutes, cooled to 4° C. for 5 minutes, and then incubated at room temperature for 5 minutes This ssDNA library was incubated with a final concentration of 3 µM of the HCP protein bound to the magnetic beads for two hours to allow aptamers to bind to their protein targets. After two hours, the beads were washed 3 times in PBSMCT buffer (1× phosphate buffered saline, 1.5 mM $MgCl_2$, and 1 mM $CaCl_2$, 0.01% Tween 20) (Hyclone; Logan, Utah). The ssDNA (aptamers) was eluted from the protein target by heating the beads in 50 µL of water for 5 minutes at 95° C. The aptamers obtained here were amplified by PCR in preparation of the next round.

Example 3. Selecting a Plurality of Candidate Aptamers

Particle display was used to select for specific aptamers that bound to specific HCPs. The microfluidics anti-HCP candidate aptamer pool was mixed with beads so that, statistically, only one aptamer of a single sequence was bound per bead. The goal is to have only 20% of the beads coated with aptamers. As the percentage of coated beads starts to get higher than this, the beads start to have more than one sequence in each droplet. Emulsion PCR was used to expand the number of aptamers per bead. In total, there were ~$10^7$ aptamer coated beads, with each bead coated homogeneously with multiple aptamers of a single sequence. These aptamer-coated beads were incubated with 20 nM Alexa-647-labeled HCPs in the presence of salmon-sperm DNA, which is added to reduce non-specific binding, and then sorted by FACS. Beads with a high amount of bound Alexa-647 signal were collected and then subjected to high-throughput DNA sequencing.

Specifically, following elution of the ssDNA aptamers off the beads, the DNA was amplified and purified (Qiagen) yielding dsDNA free of primers. This dsDNA was then used to perform emulsion PCR with 1 µm diameter forward primer coated beads in order to produce monoclonal aptamer candidate particles. Flow cytometry based binding assays with various concentrations of biotinylated HCP (bHCP) were performed with the monoclonal aptamer particles in order to determine appropriate conditions for sorting. Once suitable conditions were determined, aptamer containing particles were sorted using a fluorescence activated cell sorting (FACS) instrument.

A) Aptamer-Coated Particles Used in Particle Display

Aptamer particles were generated via emulsion PCR [Dressman et al., Transforming Single DNA Molecules Into Fluorescent Magnetic Particles for Detection and Enumeration of Genetic Variations, *Proc Nat Acad Sci* 100(15) 8817-8822 (2003)]. DNA extension was performed on forward-primer beads that had been synthesized according the protocol for coating Dynabeads® MyOne™ carboxylic acid magnetic particles (Invitrogen™ Life Technologies cat #65011) with amine-modified ssDNA. Briefly, 500 µL of 1 µm MyOne™ carboxylic acid magnetic particles ($10^7$/µL; Life Technologies) were washed once with 500 µL of 0.001 N NaOH, and three times with 1 mL of nuclease-free water, followed by re-suspension in 150 µL reaction mixture containing 200 mM NaCl, 0.2 mM 5'-amino-modified FP (5'-amino-PEG18-AGC AGC ACA GAG GTC AGA TG-3'), 1 mM imidazole chloride, 50% v/v dimethyl sulfoxide (DMSO), and 250 mM 1-ethyl-3-(3-dimethylaminopropyl) carbodiimide (EDC) (Pierce Biotechnology). Amino group modification enables covalent coupling, keeping FPs attached to the particles during thermal cycling, with PEG18 and the 5' end serving as a spacer. Particles were mixed well with reagents, vortexed, sonicated, and incubated overnight at room temperature on a rotator. After coupling the forward primer (FP), the bead surfaces were passivated with PEG12 molecules to prevent non-specific binding of the target HCPs. The remaining carboxyl groups on the particles were converted into amino-reactive NHS-esters in the presence of 250 mM EDC and 100 mM N-hydroxysuccinimide (NHS) in 2-(N-morpholino) ethanesulfonic acid (MES) buffer (100 mM, pH 4.7; Pierce Biotechnology) for 30 minutes at room temperature, followed by conjugation with 20 mM amino-PEG12 (Pierce Biotechnology) in MES buffer for one hour. The particles were washed four times with 500 µL of TE buffer (10 mM Tris, pH 8.0, 0.1 mM EDTA), suspended in 500 µL of TE buffer and stored at 4° C.

Emulsion PCR was prepared with an aqueous phase of 1× GoTaq® PCR Master Mix (Promega, Madison, Wis.), 25 mM $MgCl_2$, 3.5 mM of each dNTP (Promega), 40 nM FP, 3 µM reverse primer (RP), 0.25 U/µL of GoTaq® Hot Start Polymerase (Promega), 1 pM template DNA, and $3 \times 10^8$ FP-coated particles in a total volume of 1 mL; and an oil phase (prepared fresh each day) of 4.5% Span 80, 0.40%

Tween 80 and 0.05% Triton X-100 in mineral oil, all purchased from Sigma-Aldrich (St. Louis, Mo.). Water-in-oil emulsions were prepared by adding 1 mL of the aqueous phase to 7 mL of oil phase in a DT-20 tube (IKA) locked into the Ultra-Turrax® Device (IKA; Wilmington, Del.). This addition was performed drop-wise over 30 seconds while the mixture was being stirred at 900 rpm in the Ultra-Turrax®. After adding the aqueous phase, contents were mixed for 5 minutes. The emulsions were distributed in 100 aliquots into ~80 wells of a 96-well PCR plate. After 40 cycles of PCR the emulsions were collected into an emulsion collection tray (Life Technologies) by centrifuging at 30×g for 2 minutes. Emulsions were broken by adding 10 mL 2-butanol to the tray and transferring the collected sample to a 50 mL tube. After vortexing for 30 seconds, the particles were pelleted by centrifugation at 3,500×g for 5 minutes. After carefully removing the oil phase, the particles were re-suspended in 600 µL of emulsion breaking (EB) buffer (100 mM NaCl, 1% Triton X-100, 10 mM Tris-HCl, pH 7.5, and 1 mM EDTA) and then transferred to a new 1.5 mL tube. After vortexing for 30 seconds and centrifugation for 90 seconds at 15,000×g, the supernatant was removed. Particles were washed three times with TE pH 8.0 buffer using magnetic separation and then re-suspended in 300 µL TE.

B) Negative Controls

Two negative control samples were used to help establish gates for FACS-based sorting. Aptamer coated particles were incubated without bHCP, washed and then incubated with a streptavidin-Alexa Fluor®647 conjugate (SA-647) at a dilution of 1:500 from a stock concentration of 37 µM to determine if aptamers had affinity for the fluorescent label used in the experiment. A second negative control experiment was performed with forward primer coated beads and bHCP at the target concentration used for sorting. Following incubation and washing, the beads were incubated again with SA-647. This control was used to determine the extent to which our forward primers were binding to the target bHCP.

After setting gates based on the negative control experiments, the microfluidics anti-HCP aptamer pool on beads was incubated with bHCP at a concentration of 20 nM for 1.5 hours. The beads were washed once with PBSMCT buffer. Following this wash step, the beads were incubated with SA-647 for 15 minutes. Following the SA-647 incubation, the beads were washed again, the put back into PBSMCT buffer. Using a BD FACS Aria II instrument (BD Biosciences, Franklin Lakes, N.J.), particles with significantly higher fluorescence than background levels were sorted into a collection tube. Particles were sorted at a rate of approximately 2000 events/second for a total of three hours. Following sorting, particles were directly amplified with a pilot PCR reaction to determine an optimal cycle number for amplification of all the particles that were collected. dsDNA products resulting from this full scale amplification were purified using a Qiagen MinElute kit (Germantown, Md.).

FIG. 1 provides a FACS plot for initial UniQ-PASS generation of an anti-HCP aptamer pool, showing side scatter area versus Alexa Fluor® 647 area fluorescence intensity for 1 µm particles used in the experiment. The data show the results of aptamer coated particles incubated with 20 nM biotinylated HCP, followed by Alexa Fluor® 647 labeling. The particles in FACS gate P6 were collected and represented approximately 1.1% of the entire population evaluated. In contrast, the negative control experiments using no HCP and using forward primer coated beads plus 20 nM bHCP showed 0.0% and 0.2% of all events, respectively, in the high fluorescence P6 gate.

Example 4. Sequencing the Plurality of Candidate Aptamers in Parallel

Candidate aptamers were indexed with Illumina's TruSeq ChIP Sample Prep Kit (IP-202-1012; Illumina, San Diego, Calif.). The samples were quantified with Life Technologies Qubit® fluorometer (Q32857) and sequenced on Illumina's HiSeq 2500 with thirteen indexed TruSeq samples per lane. Eight TruSeq RNA-Seq prepared samples were added into the same pool as the 5 DNA aptamer samples solely to increase the total diversity in the run. These pooled samples were run on both lanes of a single read 90 bp rapid run.

High throughput sequencing was performed, generating approximately 7 million reads for each pool. Of the 7 million reads, approximately 1 million of the reads were unique sequences, and 10% of all the unique sequences were present in 10 copies or higher.

Example 5. Preparation of Microarray and Determination of Binding Affinity of the Candidate Aptamers to the HCP Preparation The sequences obtained from cloning and Sanger sequencing were put onto a microarray using in situ synthesis. Approximately 15,000 sequences (including control sequences) were synthesized on a single slide at known locations. A binding assay was carried out with fluorophore-labeled HCPs (bHCPs) on the slide. The slide was blocked with 0.5% acetylated bovine serum albumin (BSA) in PBSMCT buffer for 3.5 hours, and then washed. The slide was incubated with PBSMCT buffer containing 50 nM bHCP and 0.1 µg/µL salmon sperm DNA for 3 hours at room temperature, and washed again. The slide was then labeled with a streptavidin-Alexa Fluor® 647 fluorophore conjugate at a concentration of 15 nM for 15 minutes. Following washing of the slide with PBSMCT buffer, the entire slide was scanned with a GenePix® 4400B microarray scanner (Molecular Devices; Sunnyvale, Calif.). Features with high fluorescence intensity indicated binding of the HCP (target protein) to an aptamer. Each aptamer sequence was represented five times on the array (each aptamer was represented with five features) to ensure that binding events were significant.

Figure 2A:
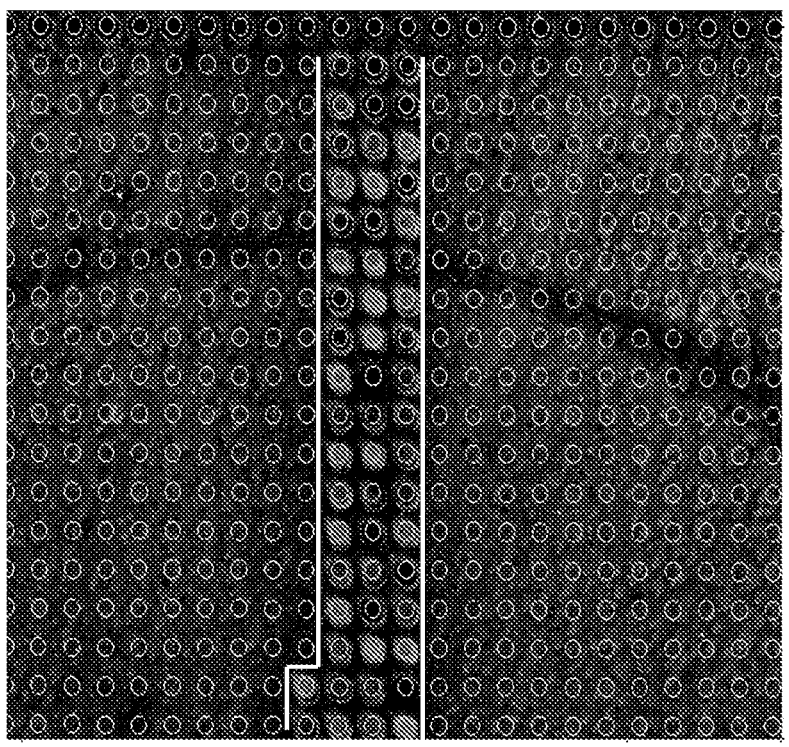
FIG. 2 shows two images from a microarray containing aptamers obtained after five rounds of particle display and incubated with Alexa Fluor® 647-labeled HCPs. Within white borders of FIG. 2A are wells containing individual aptamers surrounded by empty wells.
FIG. 2B depicts wells containing single-stranded DNA (ssDNA) of random sequences.
Figure 2B:
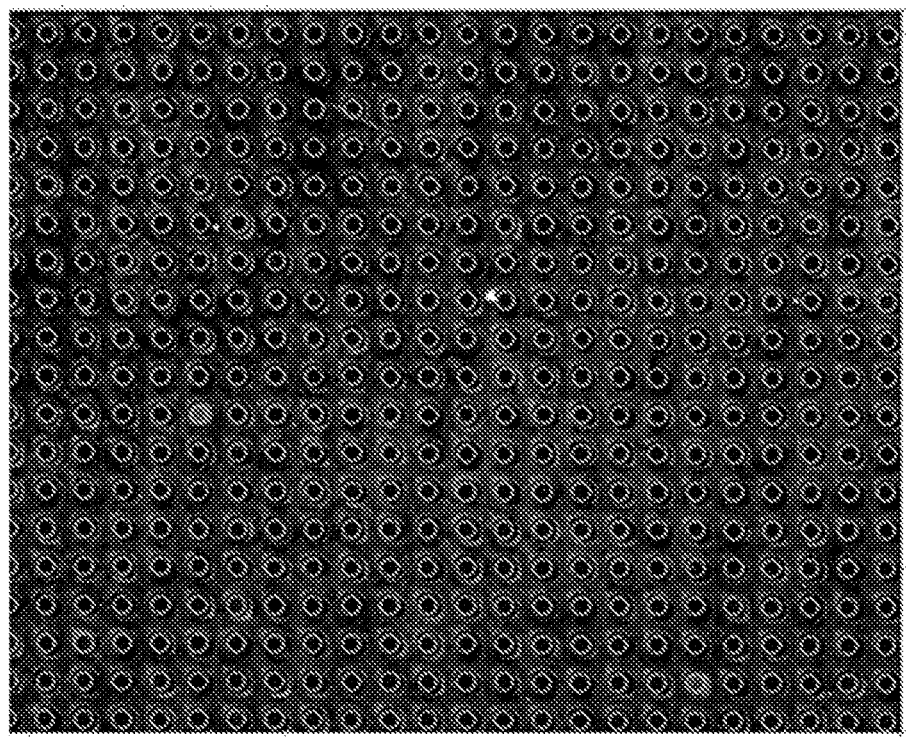

To determine specific binding of the HCPs to individual aptamers, 68 anti-HCP aptamers that were generated from five rounds of particle display, were sequenced and spotted on the array. The nucleotide sequence of these 68 aptamers are set forth in SEQ ID NO:5 to SEQ ID NO: 73 of Table 1, below. The 50 nucleotide aptamers were in situ synthesized, five times each, on a microarray slide. On a different section of the same slide, 5000 random, 50 nucleotide ssDNA oligonucleotides, were in situ synthesized on the slide. The slide was incubated with 50 nM bHCP in buffer with 0.1 µg/µL salmon sperm DNA for three hours. After labeling with a streptavidin-Alexa Fluor® 647 fluorophore conjugate at a concentration of 15 nM for 15 minutes, the slide was washed three times with PBS, and the slide was imaged. As seen in FIG. 2, protein binding was apparent in the spots containing candidate aptamers (FIG. 2A, within white borders), but binding was not apparent in the spots comprised of random ssDNA (FIG. 2B).

Figure 3:
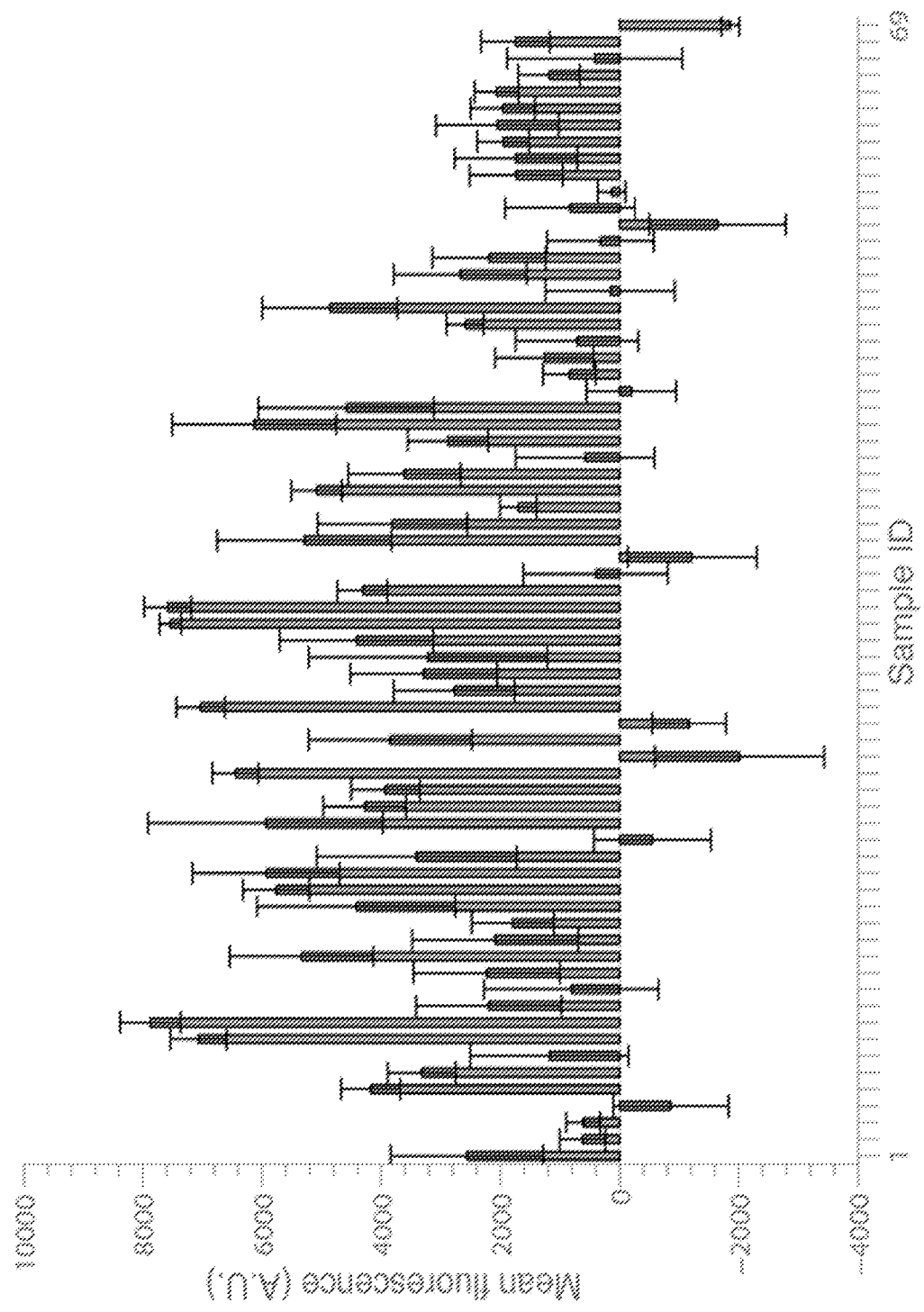
FIG. 3 shows a bar graph of the quantitation of the microarray in FIG. 2A.

The fluorescence intensity of all of the spots on the slide was quantitated. The fluorescence intensity of the individual aptamers was averaged, the background fluorescence subtracted, and the resulting fluorescence intensities were plotted as a bar graph and shown in FIG. 3. This figure shows that several of the aptamers generated a high fluorescence intensity signal, reflective of their ability to bind HCPs.

Example 6. Identification of HCPs that are Bound by Individual Aptamers Using Affinity Precipitation The specific HCPs bound by aptamers displaying positive fluorescence intensity in FIG. 3 were determined using affinity precipitation. Aptamer affinity precipitations were performed for 43 aptamers having different sequences as listed in Table 1, below. Individual 50 nucleotide (50-mer) aptamers and a 50-mer random oligonucleotide library were synthesized by Integrated DNA Technologies (Coralville, Iowa) with a 3' biotin and 18-mer internal spacer.

The 3'-biotin modified random oligonucleotide library serves as a negative control for the affinity precipitation reactions. Aptamers and oligonucleotides are supplied from the manufacturer lyophilized. Therefore, each 3'-biotin aptamer or 3'-biotin random oligonucleotides was dissolved to a final concentration of 2.5 µM in UltraPure water prior to use.

Streptavidin-coated beads (Dynabeads MyOne Streptavidin C1; Invitrogen by Life Technologies, Grand Island, N.Y.) were washed using 1× binding and washing (BW) buffer (5 mM Tris-HCl [pH 7.4], 0.5 mM EDTA, 1 M NaCl, 0.005% Tween-20). The streptavidin beads were then re-suspended according to manufacturer's instructions in 2×BW buffer (10 mM Tris-HCl [pH 7.4], 1 mM EDTA, 2 M NaCl, 0.01% Tween-20) prior to conjugation with 3'-biotin aptamers or 3'-biotin random oligonucleotides. Equal volumes of beads and 3'-biotin aptamer or 3'-biotin random oligonucleotide solution were incubated at room temperature with end over end rotation for 15 minutes. After incubation, the beads were washed twice with 1 mL 1×BW buffer and once with PBSMCT (phosphate buffered saline [pH 7.4], 2.5 mM magnesium chloride, 1 mM calcium chloride, 0.01% Tween-20) containing 0.1 mg/mL salmon sperm DNA (Invitrogen).

For affinity precipitation reactions, 1 mg of 3'-biotin aptamer or 3'-biotin oligonucleotide coated streptavidin beads were incubated with 0.5 mg HCP and 1 mg of salmon sperm DNA in a total volume 10 mL of PBSMCT. The mixture was incubated for 3-5 hours at room temperature with end over end rotation. Following incubation, the supernatant solution was removed and streptavidin beads coated with the 3'-biotin aptamer or the 3'-biotin oligonucleotide library were washed twice with 1 mL PBSMCT containing 0.1 mg/mL salmon sperm DNA, followed by one wash with PBSMCT. Bound HCPs were eluted from the 3'-biotin aptamer or 3'-biotin oligonucleotide coated streptavidin beads in 45 µL Elution buffer (1.5× NuPAGE® sample buffer [Novex by Life Technologies], 20% glycerol, 50 mM dithiothreitol [DTT]) at 97° C. for 10 minutes. The elution supernatant solutions were loaded onto a NuPAGE® 4-12% SDS-PAGE gel (Novex) with MOPS running buffer (Novex) and processed according to manufacturer's instructions. The gel was stained with SYPRO® Ruby protein gel stain (Molecular Probes, Invitrogen) according to manufacturer's instructions and analyzed using a Typhoon Trio Variable Mode Imager (GE Healthcare) using a 610 nm emission filter and 488 nm and 532 nm excitation wavelengths.

Figure 4:
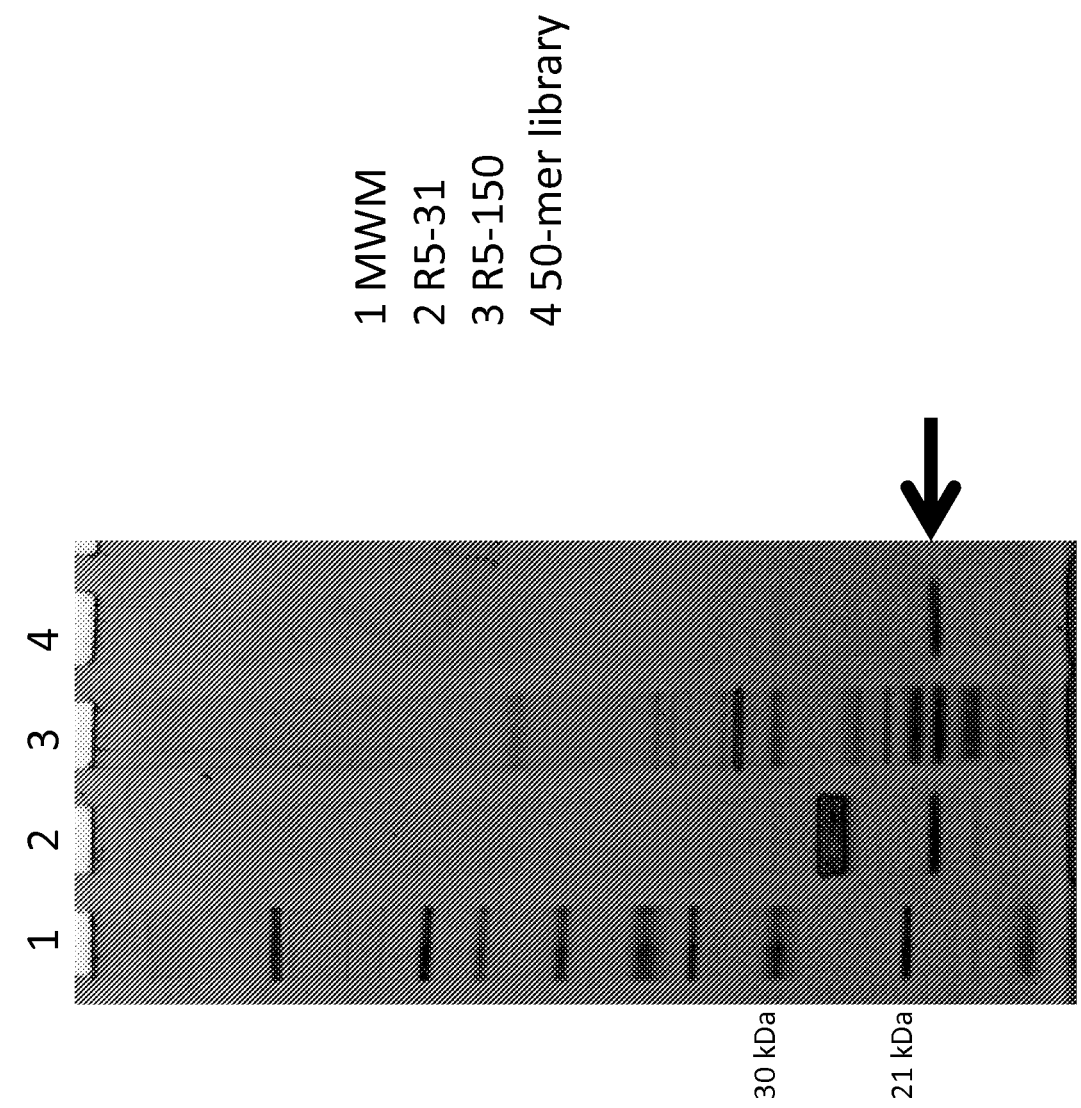
FIG. 4 shows an image from eluted supernatant solutions separated using a NuPAGE® gel electrophoresis, and the polypeptides visualized by staining the gel with SYPRO® Ruby protein gel stain.

Image of a representative nuPAGE® gel displaying the results obtained after affinity precipitation using two aptamers is shown if FIG. 4. Lane 1: molecular weight markers (Mark12, Invitrogen catalog number LC5677), with protein bands of 30 kDa and 21 kDa indicated; Lane 2: supernatant solution from the affinity precipitation reaction for the aptamer R5-31; Lane 3: supernatant solution from the affinity precipitation reaction for aptamer R5-150; Lane 4: supernatant solution from the affinity precipitation reaction of the random oligonucleotide library. The arrow on the right denotes the protein band corresponding to streptavidin (MW=17 kDa) in Lanes 2, 3 and 4. Lanes 2 and 3 show the presence of protein bands that are not present in Lane 4, indicating that specific and distinct HCPs are bound by aptamers R5-31 and R5-150. Affinity precipitations were carried out with at least 70 aptamers, with similar results.

Protein bands from SDS-PAGE gels were identified using in-gel trypsin digestion followed by liquid chromatography followed by mass spectrometry (LC-MS/MS). Half of each submitted sample was separated ~1.5 cm on a 10% Bis-Tris Novex mini-gel (Invitrogen) using the MES buffer system (described above). The gel was stained with Coomassie and each lane was excised into ten equally sized segments. Gel pieces were processed using a robot (ProGest, DigiLab) with the following protocol:

Washed with 25 mM ammonium bicarbonate followed by acetonitrile

Reduced with 10 mM DTT at 60° C. followed by alkylation with 50 mM iodoacetamide at RT Digested with trypsin (Promega) at 37° C. for 4h Quenched with formic acid, and the supernatant was analyzed directly without further processing.

The gel digests were analyzed by nano LC/MS/MS with a Waters NanoAcquity HPLC system interfaced to a ThermoFisher Q Exactive. Peptides were loaded on a trapping column and eluted over a 75 µm analytical column at 350 nL/min; both columns were packed with Jupiter Proteo resin (Phenomenex; Torrance, Calif.). The mass spectrometer was operated in data-dependent mode, with MS and MS/MS performed in the Orbitrap at 70,000 FWHM resolution and 17,500 FWHM resolution, respectively. The fifteen most abundant ions were selected for MS/MS. Data were searched using a local copy of Mascot with the following parameters: Enzyme: Trypsin; Database: Uniprot CHO (forward and reverse appended with common contaminants); Fixed modification: Carbamidomethyl (C); Variable modifications: Oxidation (M), Acetyl (Protein N-term), Pyro-Glu (N-term Q), Deamidation (NQ); Mass values: Monoisotopic; Peptide Mass Tolerance: 10 ppm; Fragment Mass Tolerance: 0.02 Da Spectral count is used in mass spectrometry as a measure of relative abundance. The identities of the HCPs bound by aptamers R5-31 and R5-150 are listed in Table 2 (below). Only HCPs with a spectral count of >50 were included, as these HCPs were assured to be in relatively high abundance. Overall, aptamer R5-31 bound to two HCPs while aptamer R5-150 bound to 8 HCPs (Table 2). The theoretical isoelectric point (pI) values and molecular weights (MWs) for all ten of the HCPs shows a wide distribution, indicating that the aptamers are not binding to a specific type of HCP (e.g. only HCPs with high pI; only HCPs lower than a certain MW).

TABLE 2

Identity of HCPs bound to Aptamers R5-31 and R5-150

| Aptamer | CHO HCP (Accession number) | Molecular weight | Theoretical isoelectric point |
|---|---|---|---|
| R5-31 | Annexin (G3IG05) | 27 kDa | 5.7 |
| | High mobility group protein B1 (G3HN43) | 22 kDa | 9.4 |
| R5-150 | Nucleolin (G3IF80) | 52 kDa | 4.4 |
| | Matrix metalloprotease-9 (G3H8V1) | 59 kDa | 5.6 |
| | Nuclease domain containing protein 1 (G3GZ85) | 100 kDa | 6.5 |
| | Polyadenylate binding protein 1 (G3I8S7) | 63 kDa | 9.7 |
| | Matrix metalloprotease-19 (G3HRK9) | 59 kDa | 7.7 |
| | Basement membrane-specific heparin sulfate proteoglycan core protein (G3HIM1) | 334 kDa | 6.4 |
| | Peroxisomal proliferator-activated receptor A-interacting complex 285 kDa protein (G3HGZ3) | 328 kDa | 8.2 |
| | Splicing factor 3B subunit (G3HAF4) | 136 kDa | 5.1 |

Example 7. Determination of the Distribution of HCPs Bound by a Select Group of Anti-HCP Aptamers Using Affinity Chromatography and Two-Dimensional Gel Electrophoresis (2DGE)

Individual 50-mer aptamers or 50-mer random oligonucleotides were synthesized by Integrated DNA Technologies (Coralville, Iowa) with a 3' amino terminus and 18-mer internal spacer. The 3'-biotin modified random oligonucleotide library serves as a negative control for the affinity chromatography reactions. Approximately 1 μmol (15 mg) of either a pool of 22 3'-amino-modified aptamers or a library of 3'-amino modified random oligonucleotides was dissolved in 2 mL coupling buffer (0.2 M sodium bicarbonate, 0.5 M sodium chloride, pH 8.3). These aptamers were chosen based on the relative number and intensity of HCPs resulting from affinity precipitation followed by SDS-PAGE (similar to the results shown at Lanes 2 and 3 of FIG. 4). The aptamers selected for this column are indicated in Table 1 (aboveXXX).

Two pre-packed 1 mL HiTrap NHS-activated HP Sepharose columns (GE) were conjugated with either the random oligonucleotide library or the pooled aptamers according to the manufacturer's instructions. Briefly, the top cap of the column was removed and 1 drop of cold 1 mM HCl was added to the column inlet. A syringe containing 1 mM HCl was then attached to the column inlet. The bottom cap of the column was removed and a second syringe was attached to the column outlet. At a manual flow rate of less than 1 ml/min (1 drop/2 sec), the column was washed with 6 mL of 1 mM HCl. Immediately following HCl wash, the ligand (either the 22 pooled aptamers or library) was loaded onto the column. After about 2 minutes, the column flow-through was passed back through the column to maximize exposure to the resin. This was repeated for 30 minutes at room temperature. The columns were washed with alternating 2 mL aliquots of Buffer A (0.5 M ethanolamine, 0.5 M NaCl, pH 8.3) and Buffer B (0.1 M Sodium acetate, 0.5 M NaCl, pH 4) according to the following pattern: 3×2 mL Buffer A, followed by 3×2 mL Buffer B, followed by 3×2 mL Buffer A, followed by allowing the column to equilibrate for approximately 30 minutes with Buffer A, followed by 3×2 mL Buffer B, followed by 3×2 mL Buffer A, followed by 3×2 mL Buffer B. Each column was then equilibrated with PBSMCT and stored at 5° C. until used.

Chromatography was performed on an AKTA Avant 125 FPLC instrument. The column was pre-equilibrated with PBSMCT+0.1 mg/mL salmon sperm DNA prior to loading. HCPs were diluted to 0.05 mg/mL in PBSMCT+salmon sperm DNA and 45 mL of the diluted HCP mixture was loaded onto the column at a flow rate of 1 mL/min. The column was washed with 10 column volumes (~10 mL) of PBSMCT+salmon sperm DNA. Bound HCPs were eluted in 5 column volumes (~5 mL) PBSMCT+2M NaCl; the eluate was collected and saved for further sample processing. Following elution, the column was then equilibrated with PBSMCT and stored until further use. This identical procedure was performed on both the 22 pooled aptamer-conjugated column and the random oligonucleotide library-conjugated column.

The eluted samples were prepared for analysis by two-dimensional gel electrophoresis (2DGE). Protein samples were buffer exchanged into 2-D cell lysis buffer (30 mM Tris-HCl, pH 8.8, 7 M urea, 2 M thiourea, 4% CHAPS). Samples are tested in pairs, with each sample of the pair labeled with a different CyDye (GE Healthcare Life Sciences): CyDye-3 (Cy3) or CyDye-5 (Cy5). Each sample was mixed with 1.0 μL of either CyDye, and kept in dark on ice for 30 minutes. The labeling reaction was stopped by adding 1.0 μL of 10 mM lysine to each sample, and incubating in dark on ice for 15 minutes. The Cy3- and Cy5-labeled samples were then mixed together. The 2×2-D Sample buffer (8 M urea, 4% CHAPS, 20 mg/ml DTT, 2% Pharmalytes, trace amount of Bromophenol blue), 100 μL de-streak solution and Rehydration buffer (7 M urea, 2 M thiourea, 4% CHAPS, 20 mg/ml DTT, 1% Pharmalytes, trace amount of Bromophenol blue) were added to the labeling mix to make the total volume of 250 μL for the 13 cm immobilized pH gradient strip (IPG strip). Each sample was mixed well and then centrifuged prior to being loaded into IPG strip holder.

2DGE works by separating proteins first based on their pI and then by mass. Isoelectric focusing (IEF; pH 3-10 linear gradient), which separates proteins by pI, was run on an Ettan isoelectric focusing (IEF) system (GE Healthcare) according to the manufacturer's instructions (GE Healthcare). Upon IEF completion, the IPG strips were incubated in the freshly made equilibration buffer-1 (50 mM Tris-HCl, pH 8.8, 6 M urea, 30% glycerol, 2% SDS, 10 mg/mL DTT, trace amount of Bromophenol blue) for 15 minutes with gentle shaking. The strips were rinsed in the freshly made equilibration buffer-2 (50 mM Tris-HCl, pH 8.8, 6 M urea, 30% glycerol, 2% SDS, 45 mg/mL iodoacetamide, trace amount of Bromophenol blue) for 10 minutes with gentle shaking. Each IPG strip was rinsed in SDS-gel running buffer before being transferred into individual 12% SDS-PAGE gels. SDS-PAGE was run at 15° C. and constant voltage until the dye front ran out of the bottom of the gel. Gels were scanned immediately following the SDS-PAGE using a Typhoon Trio Variable Mode Imager (GE Healthcare). The scanned images were then analyzed by Image Quant software (version 6.0, GE Healthcare). DeCyder software (version 6.5, GE Healthcare) was used for the spot count analysis.

When both columns were loaded with a total of 2.5 mg of HCPs, the eluate from the 22-pooled aptamer-conjugated column contained 243 distinct protein spots as determined by the DeCyder software from the two-dimensional gel, while the eluate from the random oligonucleotide library conjugated column contained 20 distinct spots, This indicates that the 22 pooled aptamer-conjugated column is binding specific HCPs while the random oligonucleotide library-conjugated column does not exhibit significant HCP binding.

Example 8. Determination of the Percent HCP Recognition (or "Coverage") of Select Anti-HCP Aptamers Using Affinity Chromatography and Two-Dimensional Gel Electrophoresis (2DGE)

Three hundred twenty-four (324) individual 50-mer aptamers were synthesized by Integrated DNA Technologies with a 3' amino terminus and 18-mer internal spacer. Approximately 12 μmol of a pool of 324 3'-amino-modified aptamers was dissolved in 2 mL coupling buffer. These 324 aptamers were chosen based on having the strongest relative fluorescence intensity for HCP binding resulting from a microarray analysis of 6000 candidate aptamers (determined from a microarray analysis performed in a manner similar to as described in Example 5). The aptamers selected for this chromatographic evaluation are indicated in Table 1, below and their nucleotide sequences are set forth in SEQ ID NOs 74-398.

A pre-packed 5 mL HiTrap NHS-activated HP Sepharose column was conjugated with 324 3'-modified anti-HCP aptamers in a manner similar to as described in Example 7. Briefly, the top cap of the column was removed and 1 drop of cold 1 mM HCl was added to the column inlet. A syringe containing 1 mM HCl was then attached to the column inlet. The bottom cap of the column was removed and a second syringe was attached to the column outlet. At a manual flow rate of less than 5 ml/min, the column was washed with 30 mL of 1 mM HCl. Immediately following HCl wash, the ligand (equi-molar mixture of 324 3'-amino modified aptamers) was loaded onto the column. After about 2 minutes, the column flow-through was passed back through the column to maximize exposure to the resin. This was repeated for 30 minutes at room temperature. The column was washed with alternating 10 mL aliquots of Buffer A and Buffer B according to the following pattern: 3×10 mL Buffer A, followed by 3×10 mL Buffer B, followed by 3×10 mL Buffer A, followed by allowing the column to equilibrate for approximately 30 minutes with Buffer A, followed by 3×10 mL Buffer B, followed by 3×2 mL Buffer A, followed by 3×10 mL Buffer B. The column was then equilibrated with PBSMCT and stored at 5° C. until used.

Chromatography was performed on an AKTA Avant 125 FPLC instrument in a manner similar to as described in Example 7. The column was pre-equilibrated with PBSMCT+0.1 mg/mL salmon sperm DNA prior to loading. HCPs were diluted to 2.5 mg/mL in PBSMCT+salmon sperm DNA and 95 mL of the diluted HCP mixture was loaded onto the column at a flow rate of 5 mL/min. The column was washed with 5 column volumes (~25 mL) of PBSMCT+salmon sperm DNA. Bound HCPs were eluted in 5 column volumes (~25 mL) PBSMCT+2M NaCl; the eluate was collected and saved for further sample processing. Following elution, the column was then equilibrated with PBSMCT and stored until further use.

The eluted sample and a sample of the HCP load (HCP mixture prior to chromatography) were prepared for analysis by 2DGE in a manner similar to as described in Example 7. Protein samples were buffer exchanged into 2-D cell lysis buffer. Each sample was mixed with 1.0 μL of either Cy3 or Cy5, and kept in dark on ice for 30 minutes. The labeling reaction was stopped by adding 1.0 μL of 10 mM lysine to each sample, and incubating in dark on ice for 15 minutes. The Cy3- and Cy5-labeled samples were then mixed together. The 2×2-D Sample buffer, 100 μL de-streak solution and Rehydration buffer were added to the labeling mix to make the total volume of 250 μL for the 13 cm IPG strip. Each sample was mixed well and then centrifuged prior to being loaded into IPG strip holder.

Upon IEF completion, the IPG strips were incubated in the freshly made equilibration buffer-1 for 15 minutes with gentle shaking. The strips were rinsed in the freshly made equilibration buffer-2 for 10 minutes with gentle shaking. Each IPG strip was rinsed in SDS-gel running buffer before being transferred into individual 12% SDS-PAGE gels. SDS-PAGE was run at 15° C. and constant voltage until the dye front ran out of the bottom of the gel. Gels were scanned immediately following the SDS-PAGE using a Typhoon Trio Variable Mode Imager. The scanned images were then analyzed by Image Quant software. DeCyder software was used for the spot count analysis.

The eluate from the 324-aptamer conjugated column, when loaded with a total of 250 mg of HCPs, contained 1627 distinct protein spots as determined by 2DGE, while the HCP load sample (input) contained 2052 distinct protein spots. The percent coverage, or number of spots bound to by the 324 aptamer-conjugated column, was 79.3%. Therefore, the 324 aptamers, specifically selected for their ability to bind to HCPs, bound to approximately 80% of the total HCPs present.

The foregoing written specification is considered to be sufficient to enable one skilled in the art to practice the embodiments. The foregoing description and Examples detail certain embodiments and describes the best mode contemplated by the inventors. It will be appreciated, however, that no matter how detailed the foregoing may appear in text, the embodiments may be practiced in many ways and the claims include any equivalents thereof.

TABLE 1

SEQ ID Numbers and Aptamer Sequences Used in Affinity Precipitation Studies

| Sequence | Name | SEQ ID NO: | Used in affinity chromatography column? |
|---|---|---|---|
| AGCAGCACAGAGGTCAGATG | PCR primer 1 | 1 | No |
| CCTATGCGTGCTACCGTGAA | PCR primer 2 | 2 | No |
| $X_1$-i-CCTATGCGTGCTACCGTGAA | Linker 1 | 3 | No |
| AGGTCAGATG-$X_1$-i-CCTATGCGTG | Linker 2 | 4 | No |
| GTTCATTCCGCCTTCTTTGGTCTAGGTCCGGACCAATTGTTATTTCGTTC | R5-150 | 5 | Yes |
| CGAAAACAAGCTTAGCAGGCCGTGCGTCGGCACGGCGCGATTATCGGCTA | R5-65 | 6 | No |
| CGAAAACAAACTTAGCAGGCCGTGCGTCGGCACGGCGCGATTATCGGCTA | R5-88 | 7 | No |

TABLE 1-continued

SEQ ID Numbers and Aptamer
Sequences Used in Affinity Precipitation Studies

| Sequence | Name | SEQ ID NO: | Used in affinity chromatography column? |
|---|---|---|---|
| GGAACTGGCTTATTGAGTAGGCTAATCATTCACCTGAAAAGGGTTGGCTC | R5-115 | 8 | No |
| CAAGGTGCGGTGTGGGGGGCCTTACAGACTGTTTAGGCTCCGTGACTGGC | R5-08 | 9 | Yes |
| TGGTGGGGTAGGATAGTAAGCTCGAATAATAAGCTGGGTGCGTGGTGCCG | R5-163 | 10 | Yes |
| GTACGGTGATTGAAACTGTACTTGCAGTCCTATATGGAGGTGGGAAGGTC | R5-130 | 11 | No |
| GTGTGTGGGGGTATTGGTTGAGTATTTGTGCCTATGGTCGGTCATCCTGT | R5-67 | 12 | Yes |
| AGGACGAGGACCTGACGTTGAGGACGTAGTTTTGGTCGGGGGGGGGTACA | R5-20 | 13 | Yes |
| ACGGGATGGAGTTTGTGTGGTTCACTCTTTGTGAACAGAGGGTTTGTGGA | R5-180 | 14 | No |
| GGGTGAATGCGTTAGGTACCAGGACAATATGCCCGTGGAGTTTCCAGTGC | R5-05 | 15 | No |
| GAGGTATGGCACTCCGAACGTCGGTGACCGAATGTGTGGCTCTGTGGTGT | R5-69 | 16 | Yes |
| CCGCGTGTCGGGGGGCTATTCGGTATATATCACGTCTCGCATGGGTGTGGG | R5-48 | 17 | Yes |
| CCGCGTGTTACAAGGCTCTTGGGTATATAGCATGTTTGCATGGGTGTGGG | R5-126 | 18 | Yes |
| GTGTTAAGAATGGTTTTGGAAATTGGGAAAGCTGGTCGATTTGGCCAGGG | R5-12 | 19 | No |
| GTCAGATGGTGTTATACCCGGGGTTTATTTAGTCCCTATTGGCGGGGTG | R5-138 | 20 | Yes |
| GGAGTCCGGACCTTGCTGCCTGGGGGTTTTTGAATTTGTTAACTGCTCTG | R5-33 | 21 | Yes |
| GTAATTCACTGGGCGGTATTTGTGTTTACTTCGGTTTTTGGTCTGGTCGG | R5-172 | 22 | No |
| GAACGGATCCCTGTGACTTCTGTCATGGCGGTGAACGGTGTACTACGGGG | R5-87 | 23 | Yes |
| GGGTTTTGGTGAGGGGGAAATGGAGTGGCATACGCCAGTTCACTAGGACC | R5-17 | 24 | No |
| CAGTTGCTTTGTGGGGGTCATCTTGCTGTGGTTGTGGGTTTATGGGGGCA | R5-177 | 25 | Yes |
| GGGGGCTTTATGCGGTATATGTCACTAGTTTGTTACTATCGGTTGGGAGG | R5-167 | 26 | Yes |
| TTGGGGTGCTAAGTAGATTTGGAAGTAGTGTGCATTACCTGGGTGTGCTG | R5-93 | 27 | Yes |
| GGGGGTTAGGTTTCTGTGTAAGGAGGGCTGAGACGTGCTTGGGTGGTATG | R5-145 | 28 | Yes |
| GGTAGCCCTGGCGGGAGCTAGAAAAGTCACGTTTACATAAGGTTAAGCGG | R5-18 | 29 | No |
| TGTACTATTGACGGTTGGTAAACCCGAGGGTTTTTCTGCATGGGGGATGG | R5-03 | 30 | No |
| AAAACACTGGGCGGTCGGATAACGGCACTCAATTTTTATTTCGGCAGCGG | R5-54 | 31 | No |
| TGTCATTTGTGCGGTGAGGTGGGTCCAGCTGGTCCGGGCGGGCTTAGGGG | R5-60 | 32 | No |
| GGGGGTTAGTTCTGGGACGTTGCCCCTGTGAGTACCATGGTGGCTATCCG | R5-151 | 33 | No |
| GGGGGTTAGTTCTGGGACGCTGCCCCTGTGAGTACCATGGTGGCTGTCCG | R5-21 | 34 | No |
| GGGGGTTAGTTCTGGGACGCTGCCCCTGTGAGTACCATGGTGGCTATCCG | R5-144 | 35 | No |
| CGCCACTCGGTTGTCTTATGATGGCTTTAGTTTCCGAGGGGGGTGAGAGG | R5-68 | 36 | No |
| CGGGATGTGGCCTATTGTACACAGGTGTCGTCCGTCGTCGTTGGTATG | R5-83 | 37 | No |
| CCTTCAACGTATCCCTGGGGAAGGGTGGTTATTTGGCCTAGGGGGAGGC | R5-26 | 38 | No |
| CGATCAACCCGACTAATCAAGAGGGTCGTCGGTTCGTCGTGGTAGGAAGG | R5-43 | 39 | No |
| CTAGCCTTACACAGCGGAAACTAGTCACTCCAACAATCTACGGCAGCGGG | R5-81 | 40 | No |
| AGCGTCACAGAGAAGGTCGGAGTGCAAGTAGCAGTATCATGGTATTGAGG | R5-140 | 41 | No |
| CGTTTGCCTATGCTCGTCTACCGCTCCCATCATTTGCCATTTCTTTCTCG | R5-82 | 42 | No |
| CGTCCTACCGTTACTTGAATCCCTCCCTAGTCGTTAGCTTACCCCCTATG | R5-09 | 43 | No |
| CAATGTGTCGGGGGCTCGACGAAGGAGTTTTCCGTACGGTCGCTACTAAG | R5-75 | 44 | No |
| GACCCACCTTACAGGGCAATTGACTCCAGACCGTCGGGGGTGCTCTGACG | R5-56 | 45 | No |
| CCCTGGCTTGGGCTAAAAGACGTTACTCGAGCGTATAGGGGGTCTGTACG | R5-35 | 46 | No |
| CACTCGTCCTGGGGCTTGGTCCCAGCCGCACTAACATCGAAGTCTCGCGC | R5-72 | 47 | No |
| GAAATATCTGGTGTCTCTTACTGGGGCGCAAAAAAAACGGGGGTTACGGG | R5-165 | 48 | No |
| CGGTATGTTGTCCAAGTATTTCTAGAAGGGGTTGGTAGTGGGCGGTCTTG | R5-141 | 49 | No |
| GCCGATCTTTATGCCTTCTCCGCCTGCATGAGCACCCGTCTTATGGTACC | R5-152 | 50 | No |
| GGTTCTAGAAATGCCGATTTGTTGACCACAACGAACAAACTTAGGCCATC | R5-79 | 51 | No |
| CATGCAGTAGTAGCCGGCCTGGTGCGGAGGAAGTACACCTAGAGGATGCG | R5-94 | 52 | No |
| CCAGTGTGAGTGTTTGCGTCCGGCTCCATAGTAAACGATTAACGCCGCCT | R5-162 | 53 | No |
| GGCACCGGGCCACTCCCCGTTAATGCAACTAATCCAGTCACATTGTCACG | R5-100 | 54 | No |
| GGCCGTGAACAATCTACCTTCCACCACGCCTTCTCCTTGTAAACAGCTCC | R5-13 | 55 | No |
| TCCTGTCTGGCTTCCCCTTTCTCGTCGTCATTTCACTTGTGCTCGATCCG | R5-114 | 56 | No |
| TGGAGGGGGGATTAATCTAGCAAGCGACGGGTGAACTA | R5-06 | 57 | No |
| TCCAAGTTCGAATTATCTTGGCATACCACCTATGCTCATGTAGGACGGGG | R5-61 | 58 | No |
| GGGTAGTTAGGACGTATGTGTTGTTTTCCCTGTCCAAAGGATGGCCGCGC | R5-78 | 59 | No |
| CCCGATGAAGTTACTAACGTGACAGGGTTCCATTGAGCTCGCGCCCAAGG | R5-37 | 60 | No |
| CAGGCAAGTGAAGGCCTCATTTTATGTGAGACATATTTTCCAGGCAGAGG | R5-40 | 61 | No |
| CTAGAGTTTCAAGGCTGTCTGTTATGTATCGGGATGATTAAGGACGAGGT | R5-176 | 62 | No |
| AAGTACAGTCCCATCTAGTCGGAGTCATGGAACAATTTGACTTACCGGG- | R5-161 | 63 | No |
| CCGGACGATACAATTCACCTGTTACTGTGGATTCGTTAAGCTTAGTCGGT | R5-89 | 64 | No |
| CCGGACGATACAATTCACCTGTTACTGTGAGTCGTTAAGCTTAGTCGGT | R5-121 | 65 | No |
| CCGGACGATACAATCCATCTGTTACTGTGGATTCGTTAAGCTTAGTCGGT | R5-31 | 66 | No |
| CCGGACGATACAATCCACCTGTTACTGTGGGTTCGTTAAGCTTAGTCGGT | R5-22 | 67 | No |
| CCGGACGATACAATCCACCTGTTACTGTGGATTCGTTAAGCTTAGTCGGT | R5-23 | 68 | No |
| CCGGACGATACAATCCACCTGTTATTGTGGATTCGTTAAGCTTAGTCGGT | R5-45 | 69 | No |
| CCGGACGATACAATCCACCTGTTACTGTGGATTCGTCGAGCTTAGTCGGT | R5-156 | 70 | No |
| CCGGGCGATACAATCCACCTGTTACTGTGGATTCGTTAAGCTTAGTCGGT | R5-139 | 71 | No |
| CCGGACGATACAATCCACCTGTTACTGTGGATCCGTTAAGCTTAGTCGGT | R5-142 | 72 | No |
| TTTTTTTTTTTTTTTTTTTTTTTTTTTTTTTTTTTTTTTT | poly-dT control | 73 | No |
| GGTTCTAGAAATGCCGATTTGTTGACCACAACAAACAAACTTAGGCCATC | R3-264 | 74 | Yes |
| CCGCGTTGTGCAATTTCACGGATGCGTCACTGGGGGGGTGGGTTCCG | R3-3621 | 75 | Yes |
| GTGTTAGAGTTCCTTAGGGGGGTTTCGTTTTCGGTGGGCTCGGGGTG | R3-730 | 76 | Yes |
| GCTTATTCGGCATGTATGATTGGGGGTGAGTTTGGGGGGGGTCACTTGTG | R3-1029 | 77 | Yes |
| GTGTTAGAGTTCCTTAGGGGGGGTTTCGTTTTTCGGTGGGCTCGGGGT | R3-413 | 78 | Yes |

TABLE 1-continued

SEQ ID Numbers and Aptamer
Sequences Used in Affinity Precipitation Studies

| Sequence | Name | SEQ ID NO: | Used in affinity chromatography column? |
|---|---|---|---|
| GCTTATTCGGCATGTATGATTGGGGGTGAGTTTGGGGGGGGGTCACTTG | R3-2970 | 79 | Yes |
| GTGTTAGAGTTCCTTAGGGGGGGGTTTCGTTTTTCGGTGGGGCTCGGGG | R3-2712 | 80 | Yes |
| GTCCGCCAGGTAAAATTGTTGGAGATTCGTGGGTGGGTATGGGGGATGGG | R3-5149 | 81 | Yes |
| CGCGCAAGTTCCAATCCGATAGAAAGGGGGAGCGGGGGGTCGGGATGAG | R3-1645 | 82 | Yes |
| GGGTGTCACTTCAAGGGGCTAGGTTGGTCGGTTGTTCGGTGGGGGGCAGG | R3-3741 | 83 | Yes |
| TGCCCGTCTGCTTGGGGGTATTTTCGGGGTGGGCCTTTTGTTGTTGGCAC | R3-3061 | 84 | Yes |
| AGGACGAGGACCTGACGTTGAGGACGTAGTTTTGGTCGGGGGGGGGTACA | R3-5935 | 85 | Yes |
| CCTTCAACGTATCCCTGGGAAAGGGTGGTTATTTGGCCTAGGGGGGGGC | R3-1587 | 86 | Yes |
| GGATAATTGCTCACATTCGTTGGGGGGGGGGGAGTGGTGTGTTTAACCG | R3-2866 | 87 | Yes |
| CGCGCAAGTTCCAATCCGATAGAAGAGGGGAGCGGGGGTCGGGATGAGG | R3-2912 | 88 | Yes |
| GGCAATAAAAGGCTGATCATTCCAGATTACGTCTCGTGGGGGGGGTCGG | R3-921 | 89 | Yes |
| GTCCACCAGGTAAAATTGTTGGAGATTCGTGGGTGGGTATGGGGGATGGA | R3-3991 | 90 | Yes |
| CGCCACTTGGTTGTCTTACGATGGCTTTAGTTTCCGAGGGGGGTGAGAGG | R3-4578 | 91 | Yes |
| CTCAGACTCGTACACCACAATCAGGACTGCGGTTCGGGGTGGCGTGGGAA | R3-1640 | 92 | Yes |
| ATCATGGGCTACCTCACAACGGGTTTATCATTTCTGGGGTTTGGGGGGCG | R3-4512 | 93 | Yes |
| CTGCTTTTGGCGTTCGATCGTGTTCCTGGTTTGTGTCCTGGGGTGGGTG | R3-2778 | 94 | Yes |
| TGACCGACACTTATGCGGGTAAGAAGAGTAGCGCGGGGTGGGGCATGCCG | R3-3252 | 95 | Yes |
| TAAGTGTCGGGGTCTGTCCATATTGTAAGGCATGGGGTGTGTCGGGGGCG | R3-1447 | 96 | Yes |
| TTGACGTTTTCCTCTGGGATAAGGGTTGGGGGGGATGTGGGCACTGCGAG | R3-1593 | 97 | Yes |
| AATGGGGCACAGACTACGGAGCGGAAGGTAGCTGTCTGGTCGGGGGGTCT | R3-5010 | 98 | Yes |
| CAGTTGCTTTGTGGGGGTCGTCTTGCTGTGGTTGTGGGTTTATGGGGGCA | R3-4916 | 99 | Yes |
| AATGGGGCACAGACTACGGAGCGGAAAGTAGCTGTCTGGTCGGGGGGGTC | R3-4737 | 100 | Yes |
| TGACCAACGGCCATTGACTTACTGGTGCCCAACATCCCGGGGTAGGGGTG | R3-1067 | 101 | Yes |
| GCTGTTATTCTTTACACGTGACGCGTTTGGGGTCTTGCGACCTGGGGGTG | R3-5604 | 102 | Yes |
| CGCTTTCTCCATTAGTGGCCTCATGACGGTAAGGAGTAGAGGGGGAGGTG | R3-370 | 103 | Yes |
| GCTTATTCGGCATGTATGATTGGGGGTGAGTTTGGGGGGGGTCACTTGT | R3-529 | 104 | Yes |
| CGCGCAAGTTCCAATCCGATAGAAGAGGGGAGCGGGGGGTCGGGATGAG | R3-324 | 105 | Yes |
| GTGTTAGAGTTCCTTAGGGGGGGGTTTCGTTTTTCGGTGGGGCTCAGGGT | R3-4488 | 106 | Yes |
| GTCCGCCGGGTAAAATTGTTGGAGATTCGTGGGTGGGTATGGGGGATGGA | R3-4436 | 107 | Yes |
| GTCCACCAGGTAAAATTGTTGGAGATTCGTGGGTGGGTATGGGGGATGGA | R3-2848 | 108 | Yes |
| GGCAATAAAAGGCTGATCACTCCAGATTACGTCTCGTGGGGGGGGTCGGT | R3-5316 | 109 | Yes |
| GGATAATTGCTCACATTCGTTGGGGGGGGGGAGTGGTGTGTTTAACCGA | R3-664 | 110 | Yes |
| GTCCGCCAGGTAAAATTGTTGGAGATTCGTGGGTGGGTATGGGGGATGGA | R3-274 | 111 | Yes |
| AGGACGAGGACCTGACGTTGAGGACGTAGTTTTGGTCGGGGGGGGTACAG | R3-620 | 112 | Yes |
| GGCAATAAAAGGCTGATCATTCCAGATTACGCCTCGTGGGGGGGGTCGGT | R3-5599 | 113 | Yes |
| GGATAATTGCTCACATTCGTTGGGGGGGGGGAGTGGTGTGTTTAACCGAC | R3-365 | 114 | Yes |
| CGCCACTTGGTTGTCTTATGATGGCTTTAGTTTCCGAGGGGGGTGGGAGG | R3-2459 | 115 | Yes |
| CGCCACTTGGTTGTCTTATGATGGCTTTAGTTTCCGAGGGGGGGTAGGGG | R3-4423 | 116 | Yes |
| GGCAATAAAAGGCTGATCATTCCAGATTACGTCTCGTGGGGGGGGTCGGT | R3-258 | 117 | Yes |
| CCTTCAACGTATCCCTGGGAAAGGGTGGTTATTCGGCCTAGGGGGGAGGC | R3-5477 | 118 | Yes |
| GATCACGCTTGTCGCTAGGGGGTGCGGGTGGGAAGCCATTTTCGTCCCA | R3-2713 | 119 | Yes |
| TCCCGTCCGATAGTTGGGGTAGGTGTATGCGGTTGTTTATGGGGGGGGAT | R3-5943 | 120 | Yes |
| GTATATCTCTCAGTGTCCGCCGGTTACGGGGGCCCGAACCAAGTGGGGGG | R3-3931 | 121 | Yes |
| GGCAATAAAAGGCTGATCATTCCGATTACGTCTCGTGGGGGGGGTCGGT | R3-2765 | 122 | Yes |
| CCTTCAACGTACCCCTGGGAAAGGGTGGTTATTTGGCCTAGGGGGGAGGC | R3-4350 | 123 | Yes |
| CCTTCAACGTATCCCTGGGAAAGGGTGGTTATTTGGTCTAGGGGGGAGGC | R3-5334 | 124 | Yes |
| CTGCTTTTGGCGTTCGATCGTGTTCCTGGTTTGTGTCCACGGGGTGGGTG | R3-678 | 125 | Yes |
| CCTTCAACGTATCCCTGGGAAAGGGTGGTTATTTGGCCTAGGGGGGAGGC | R3-2803 | 126 | Yes |
| GGCAATAAAAGGCTGATCATTCCAGATTACGTCTCGCGGGGGGGGTCGGT | R3-5632 | 127 | Yes |
| GTCCGCCAGGTAAAATTGTTGGAGATTCGTGGGAGGGTATGGGGGATGGA | R3-5262 | 128 | Yes |
| CGCCACTTGGTTGTCTTATGATGGCTTTAGTTTCCGGGGGGGGGTGAGAGG | R3-2804 | 129 | Yes |
| CTCAGACTCGTACACCACAATCAGGACTGCGGTTCGGGGTGGCGTGGG | R3-282 | 130 | Yes |
| CTGCTTTTGGCGTTCGATCGCGTTCCTGGTTTGTGTCCATGGGGTGGGTG | R3-3008 | 131 | Yes |
| CTGCTTTTCGGCGTTCGATCGTGTTCCTGGTTTGTGTCCATGGGGTGGGTG | R3-3915 | 132 | Yes |
| GGATAATTGCTCACATTCGTTGGGGGGGGGAGTGGTGCGTTTAACGAC | R3-5514 | 133 | Yes |
| CTGCTTTTGGCGTTCGACCGTGTTCCTGGTTTGTGTCCATGGGGTGGGTG | R3-1226 | 134 | Yes |
| GGTCCTAAAGGTCGAGCGTTAGAAACAGCCTAGAGGGGGGTGG | R3-4894 | 135 | Yes |
| CTGCTTTTGGCGCTCGATCGTGTTCCTGGTTTGTGTCCATGGGGTGGGTG | R3-3405 | 136 | Yes |
| CCTCCAACGTATCCCTGGGAAAGGGTGGTTATTTGGCCTAGGGGGGAGGC | R3-4384 | 137 | Yes |
| GCGGCGTCGGTCCAGGGGGTAGTAGTACTTACAGGGGTGGGATGCTTGTC | R3-660 | 138 | Yes |
| CCTTCAACGTATCCCTGGGAAAGGGTGGTCATTTGGCCTAGGGGGGAGGC | R3-1781 | 139 | Yes |
| CTGCTTTTGGCGTTCGATCGTGTTCCTGGTCTGTGTCCATGGGGTGGGTG | R3-2675 | 140 | Yes |
| CTGCTTTTGGCGTCCGATCGTGTTCCTGGTTTGTGTCCATGGGGTGGGTG | R3-4962 | 141 | Yes |
| GTCCCTCGTTTCTTGTACTACCCTTACTCCCCCCAACCCGCTGTTCTGT | R3-5302 | 142 | Yes |
| CTGCTTTTGGCGTTCGATCGTGTTCCCGGTTTGTGTCCATGGGGTGGGTG | R3-2602 | 143 | Yes |
| CCGCTTTTGGCGTTCGATCGTGTTCCTGGTTTGTGTCCATGGGGTGGGTG | R3-5318 | 144 | Yes |
| CTGCTTTTGGCGTTCGATCGTGTTCCTGGTTTGTGTCCATGGGGTGGGTG | R3-3241 | 145 | Yes |
| GGATAATTGCTCACATTCGTTGGGGGGGGAGTGGTGTGTTTAACCGACG | R3-513 | 146 | Yes |
| CTGCTTCTGGCGTTCGATCGTGTTCCTGGTTTGTGTCCATGGGGTGGGTG | R3-5143 | 147 | Yes |
| CCTTCAGCGTATCCCTGGGAAAGGGTGGTTATTTGGCCTAGGGGGGAGGC | R3-5960 | 148 | Yes |
| GGGTCTTATTCTGGTATTGTTAGTTATGGGGGTGTCGTCGGCGGGACCTG | R3-2023 | 149 | Yes |
| CAGTTGCTTTGTGGGGTCATCTTGCTGTGGTTGTGGGTCTATGGGGCA | R3-4286 | 150 | Yes |

TABLE 1-continued

SEQ ID Numbers and Aptamer
Sequences Used in Affinity Precipitation Studies

| Sequence | Name | SEQ ID NO: | Used in affinity chromatography column? |
|---|---|---|---|
| GTGTCTCGCTTGCAGGTTAGGGGGGGTTGGGGATTGACCCTTATACAGCG | R3-2897 | 151 | Yes |
| CTAGCGGGGGGTTTATCTAGATGTCGTGGGCCCTGGGGGGGCCTGCTACG | R3-3984 | 152 | Yes |
| CCTTCAACGCATCCCTGGGAAAGGGTGGTTATTTGGCCTAGGGGGGAGGC | R3-2393 | 153 | Yes |
| TCCCGTCCGATAGCTGGGGTAGGTGTATGCGGTTATTTATGGGGGGGGAT | R3-1975 | 154 | Yes |
| CGCCACTTGGTTGTCTTATGATGGCTTTAGTTTCCGAGGGGGGGTGAGAG | R3-2430 | 155 | Yes |
| GGAAAGTTGTTGTCCGGCGAAGTCTGAAGGGTCGGGTCTGGGGCATTCGG | R3-5885 | 156 | Yes |
| CCTTCAACGTATCCCTGGGAAAGGGTGGTTATTTGGCCTAGGGGGGAGGC | R3-146 | 157 | Yes |
| GTCCCTCGTTTTCTTGTGCTACTTTACTCCCCCCCAACCCGCTGTTCTGT | R3-4610 | 158 | Yes |
| CAGTTGCTTTGTGGGGGTCATCTTGCTGTGGTTGTGGGTTTGTGGGGGCA | R3-4906 | 159 | Yes |
| CTGCTTTTGGCGTTCGATCGTGTTCCTGGTTTGTGTCCATGGGGCGGGTG | R3-3886 | 160 | Yes |
| CCCTCAACGTATCCCTGGGAAAGGGTGGTTATTTGGCCTAGGGGGGAGGC | R3-4858 | 161 | Yes |
| CTGCTTTTGGCGTTCGATCGTGTTCCTGGTTTGTGTCCATGGGTGGGTG | R3-92 | 162 | Yes |
| CCTTCAACGTATCCCTGGGAAAGGGTGGTTATTTGGCCTAAGGGGGAGGC | R3-5707 | 163 | Yes |
| GCCCCTCGTTTTCTTGTACTACTTTACTCCCCCCCAACCCGCTGTTCTGT | R3-5077 | 164 | Yes |
| TTAACATTCTGGATTCCCTGTTTCAGCCAGCAAAGACTGGGGGGGGCAAG | R3-1856 | 165 | Yes |
| GTCCCTCGTTTTCTTGTACTACTTTACTCCCCCCCAACCCGCTGTTCTGT | R3-270 | 166 | Yes |
| CTGCTTTTGGCGTTCGATCGTGTTCCTGGTTTGTGTCCATGGGTGGGTG | R3-4322 | 167 | Yes |
| CCGGGGTGCAGCGGCCAGTATATACGAAATCTCACAGAAGGGGTGGGGGC | R3-561 | 168 | Yes |
| CCTTCAACGTATCCCTGGGAGAGGGTGGTTATTTGGCCTAGGGGGGAGGC | R3-3547 | 169 | Yes |
| ACGTAACCATCACCGGGTGCCCCCTCGGGGGGCAGGGTAATGTCGCGCC | R3-4462 | 170 | Yes |
| GAGGCGGGGATTTAGAAATGTGATCAACGAACCATTCCAAGGGGTGGGGG | R3-3467 | 171 | Yes |
| GTTGCAATTTTTCTACCTTGGAGGCGCCGTTCTTGGGGGTCACGGGTGGC | R3-5872 | 172 | Yes |
| GGCAATAAAAGGCTGATCATTCCAGATTACGTCTCGTGGGGGGTCGGTG | R3-1062 | 173 | Yes |
| GTCCCTCGTTTTCTTGTACTACTTTACTCCCCCCCAACCCGCTGTTCTG | R3-3387 | 174 | Yes |
| GTCCCCCGTTTTCTTGTACTACTTTACTCCCCCCCAACCCGCTGTTCTGT | R3-2813 | 175 | Yes |
| CTGAAGGACGTGCGCCATTGTTTCAGTGGGGTCGGGGATAAATTCTCGG | R3-3262 | 176 | Yes |
| CTCAGACTCGTACACCACGATCAGGACTGCGGTTCGGGTGGCGTGGG | R3-4907 | 177 | Yes |
| AATACGTCTGGCGGGAACGCTCTGAATCCATGGTGCTTCGGCGGGTGGGA | R3-1135 | 178 | Yes |
| CGCCACTTGGTTGTCTTATGATGGCTTTAGGTTCCGAGGGGGGTGAGAGG | R3-5697 | 179 | Yes |
| CAGTTGCTTTGTGGGGGTCATCTTGCTGTGGTTGTGGGTTTATGGGGGTA | R3-5059 | 180 | Yes |
| TAGGTCACAAGAGCTGATAGGGCAATCGACGGGGTGGGTGAGTATAGGCA | R3-765 | 181 | Yes |
| AGTGTGCTTGTGAGCCCGTGAATATCGCGTAGGGGTGGCTTCGGGGCCG | R3-2371 | 182 | Yes |
| TACCAAACGACAGGAATATAAAGGGGGATGGGTCTACTGGGCGACGTG | R3-761 | 183 | Yes |
| CAGTTGCTCTGTGGGGGTCATCTTGCTGTGGTTGTGGGTTTATGGGGGCA | R3-3737 | 184 | Yes |
| GGCCGCCTCGAAGGCTCGTTAATTGTTGGGACCGGGTGGGCTATTGTTCG | R3-2773 | 185 | Yes |
| CGCCACTTGGTTGTCTCATGATGGCTTTAGTTTCCGAGGGGGTGAGAGG | R3-4224 | 186 | Yes |
| CTGCTTTTGGCGTTCGATCGTGCTCCTGGTTTGTGTCCATGGGTGGGTG | R3-2462 | 187 | Yes |
| TTTGTAGACATTGTGGCTGGTGGGGATGGGTTTGGCTGTGGTGGTAGTT | R3-1736 | 188 | Yes |
| AGGACGAGGACCTGACGTTGAGGACGTAGTTTTGGTCGGGGGGTACAGG | R3-2261 | 189 | Yes |
| CGGGGGTCACCGGTCATGGATTAAGGCGTAGTTGATGGTATGGGTGGG | R3-2094 | 190 | Yes |
| TCCCGTCCGATAGCTGGGGTAGGTGTATGCGGTTGTTTATGGGGGGGATG | R3-2434 | 191 | Yes |
| CATGTCGAAACAATCTTGGGCCGGGGGGGGGGTCCATCCTAAAAAGGTGA | R3-4810 | 192 | Yes |
| CGCCACTTGGTTGTCTTATGGTGGCTTTAGTTTCCGAGGGGGTGAGAGG | R3-3755 | 193 | Yes |
| TCCCGTCCGATAGCTGGGGTAGGTGTATGCGGTTGTTTATGGGGGGGAT | R3-450 | 194 | Yes |
| AGTTGCCAATGGCGGTCATACAATGGACCTACGCGCGCGATGGGGGGTC | R3-1136 | 195 | Yes |
| GCAAGGTATGGTGTGTGATGGGTGGGGGGTGCAGAGGGTTCAGGGAGGTG | R3-2207 | 196 | Yes |
| CGGAGAGACAGGCTGGTTCGTTTCGGTCAGTGGGGGGGTTTTATGAGTTG | R3-3351 | 197 | Yes |
| AACAATGCTGGATATAGCATGCTGGGAGGGTGGTGTCGACGGGGGTTGTA | R3-4199 | 198 | Yes |
| GTCCCTCGTTTTCTTGTACTACTTTACCCCCCCCCAACCCGCTGTTCTGT | R3-3862 | 199 | Yes |
| CTGCTTTGGCGTTCGATCGTGTTCCTGGCTTGTGTCCATGGGTGGGTG | R3-2767 | 200 | Yes |
| CAGTTGCTTTGTGGGGGTCATCTTGCTGTGGTTGTGGGTTTATGGGGGC | R3-5393 | 201 | Yes |
| CTGCTTTTGGCGTTCGATCATGTTCCTGGTTTGTGTCCATGGGTGGGTG | R3-5847 | 202 | Yes |
| CAGTTGCTTTGTGGGGTCATCTTGCTGTGGTTGTGGGTTATGGGGCAG | R3-5802 | 203 | Yes |
| TCTTGGATCACCGTACATCTTTGCCATTGCTACCGCCATAGGGGTTCTTG | R3-2213 | 204 | Yes |
| AATGGGGCACAGACTACGGAGCGGAAAGTAGCTGTCTGGTCGGGGTCT | R3-315 | 205 | Yes |
| CGCCACTTGGTTGTCTTATGATGGCCTTAGTTTCCGAGGGGGTGAGAGG | R3-695 | 206 | Yes |
| GTTAAAGTGAAGTGCGAGCGTTGTTTAGCATTGTCGGGTGGGCTATTTGG | R3-2334 | 207 | Yes |
| CTGCTCTTGGCGTTCGATCGTGTTCCTGGTTTGTGTCCATGGGTGGGTG | R3-4166 | 208 | Yes |
| CAGTTGCTTTGTGGGGGTCATCTTGCTGTGGCTGTGGGTTATGGGGGCA | R3-2244 | 209 | Yes |
| GAAATATCTGGTGTCTCTTACTGGGCGCAAAAAAACGGGGGTTACGGGG | R3-611 | 210 | Yes |
| CAGTTGCTTTGTGGGGGTCATCTTGCTGTGGTTGTGGGTTATGGGGCA | R3-67 | 211 | Yes |
| CGCCACTTGGTTGTCTTATGATGGCTTTAGTTCCCGAGGGGGTGAGAGG | R3-5439 | 212 | Yes |
| GTGTCTCGCTTGCAGGTTAGGGGGGTTGGGGTTGACCCTTATACAGCG | R3-4449 | 213 | Yes |
| TCAGATTGTCGACAAACCAGTCCGGACGGATAGGGTGCTCGGGGGCTCGG | R3-5070 | 214 | Yes |
| TGTCATTTGTCGGTGAGGTGGGTCCAGCTGGTCCGGCGGGCTTAAGGG | R3-291 | 215 | Yes |
| AATGGGGCACAGACTACGGAGCGGAAAGTAGCCGTCTGGTCGGGGGTCT | R3-4632 | 216 | Yes |
| CAGCTGGACAACAGAGAGGCGATGAACTCAATCTCGGGGGGGTCATTTG | R3-3694 | 217 | Yes |
| CAGTTGCCTTGTGGGGGCATCTTGCTGTGGTTGTGGGTTTATGGGGCA | R3-2265 | 218 | Yes |
| GGCATATACTGGTGCGATCCGAATGCCGGCCGGTCCCATAGGCGGGGGT | R3-3424 | 219 | Yes |
| GTCAAGTATTCAAGTTCGACCAGGGGGGGTTCCGGGACAGGGATAGGGGG | R3-4978 | 220 | Yes |
| TGTACTATTGACGGTTGGTAAACCCGGGGGTTTTTCTGCATGGGGATGG | R3-2858 | 221 | Yes |
| CGCCACTTGGTTGTCTTATGACGGCTTTAGTTTCCGAGGGGGTGAGAGG | R3-1526 | 222 | Yes |

TABLE 1-continued

SEQ ID Numbers and Aptamer
Sequences Used in Affinity Precipitation Studies

| Sequence | Name | SEQ ID NO: | Used in affinity chromatography column? |
|---|---|---|---|
| CAGCATGGGTCATTTCGAGCTTGATAGTGTCTATGGCGGGGCGTTGCGGG | R3-1791 | 223 | Yes |
| CCTTCAACGTATCCCTGGGGAAGGGTGGTTATTTGGCCTAGGGGGAGGC | R3-4543 | 224 | Yes |
| TGGGGGCGAATACATGATGGGTTTCTAATGTAGAGGCAGAGGGGGAGAC | R3-3822 | 225 | Yes |
| ACGGGAGTTTACCATGGGGGCTTGTTAGGGGGGTAGATATGTATCAGATA | R3-519 | 226 | Yes |
| CGCCACTTGGTTGCCTTATGATGGCTTTAGTTTCCGAGGGGGGTGAGAGG | R3-3850 | 227 | Yes |
| AGGATGTTTAGTCCTAGTGGGGGGGTCTATTTCAACATAAGGGGTGGTGA | R3-3668 | 228 | Yes |
| CACCCACTTGGTTGTCTTATGATGGCTTTAGTTTCCGAGGGGGTGAGAGG | R3-879 | 229 | Yes |
| ACAACCCCGAGGTGCAACGACGAGTTAGGTATCCTGGGGAGGGCACACGT | R3-4613 | 230 | Yes |
| GGATAATTGCTCACATTCGTTGGGGGGGAGTGGTGTGTTTAACCGACG | R3-1020 | 231 | Yes |
| CTGCCTTTGGCGTTCGATCGTGTTCCTGGTTTGTGTCCATGGGTGGGTG | R3-2807 | 232 | Yes |
| AGGAAAGTAACCCGGAACGTACTTCCGTTTCTGGGTGGGGATGAGCGACG | R3-383 | 233 | Yes |
| ACTTCATAGTCACATTAGAGGGGGGGGTATGTCACCGTCTGTTTTTGCT | R3-5197 | 234 | Yes |
| CAGTTGCTTTGTGGGGGTCATCTTGCCGTGGTTGTGGGTTTATGGGGCA | R3-1769 | 245 | Yes |
| AAGGTCACTGGCTCATAATACTGTGAAGGGGTGCTCAACGGGTTGGGTGC | R3-5261 | 236 | Yes |
| CGCCACTTGGTTGTCTTATGATGGCTTTAGTTTCCGAGGGGGTGAGAGG | R3-71 | 237 | Yes |
| CTGCTTTTGGCGTTCGATTGTGTTCCTGGTTTGTGTCCATGGGTGGGTG | R3-5663 | 238 | Yes |
| TCAGCAGCGACTATTTGGGGCCAAGCCGGCCATGAGCTGTGGGGTCGCCG | R3-4451 | 239 | Yes |
| CGCCACTTGGCTGTCTTATGATGGCTTTAGTTTCCGAGGGGGTGAGAGG | R3-4979 | 240 | Yes |
| CGGCAAGGCATATGATCCGTCGACTCGATATACACTTCCCGGGGTGCGCG | R3-3501 | 241 | Yes |
| CGCCACTTGGTTGTCTTATGATGGCTTTAGCTTCCGAGGGGGGTGAGAGG | R3-2658 | 242 | Yes |
| TAGCAGGTTTAGGCCAGCGCACTACTACACCAAGGATGGGGGGATGCTG | R3-4967 | 243 | Yes |
| ACGGGAGTTTACCGTGGGGGCTTGTTAGGGGGGTAGATATGTATCAGATA | R3-5678 | 244 | Yes |
| CGCCACTTGGTTGTCCTATGATGGCTTTAGTTTCCGAGGGGGGTGAGAGG | R3-3852 | 245 | Yes |
| CCTTCAACGTATCCCTGGGAAAGGGTGGTTATTTGGCCTAGGGGGAGGCG | R3-2337 | 246 | Yes |
| GGTCTGTCACTCTTTCTCTCGCTTGCCCATGTCCCCACCCCCCTAGGCCA | R3-2145 | 247 | Yes |
| CAGTCGCTTTGTGGGGGTCATCTTGCCTGTGGTTGTGGGTTTATGGGGCA | R3-3585 | 248 | Yes |
| CAGTTGCTTTGTGGGGGTCATCCTGCTGTGGTTGTGGGTTTATGGGGCA | R3-4306 | 249 | Yes |
| TGTACTATTGACGGTTGGTAAACCCGAGGGTTTTTCTGCGTGGGGGATGA | R3-4019 | 250 | Yes |
| GGTCTGTCACTCTTTCTCTCGCTTGCCCATGTCCCCGTCCCCCTAGGCCA | R3-2727 | 251 | Yes |
| GCTTTTTTAACCTGGGGGCCCATGCTGGGAGTGGGGATTTGTAGGGGATG | R3-468 | 252 | Yes |
| GTGTCGGATCCGAGGAGCGCTCGGCTATTGCGCGGGGGAGGTTGTCTGGA | R3-1287 | 253 | Yes |
| CGCGAAGTGACATACGAGACGCGGTATCGGTTGGGGGGAGAAGACTTCGA | R3-5990 | 254 | Yes |
| CGCCACTCGGTTGTCTTATGATGGCTTTAGTTTCCGAGGGGGGTGAGAGG | R3-4014 | 255 | Yes |
| ACACTACCAACTGCCTACCATCACACCACACGTTTTTCAAAAACTTCGA | R3-3992 | 256 | Yes |
| AACAATGCTGGATATAGCATGCTGGGAGGGTGGTGTCGACGGGGATTGTA | R3-288 | 257 | Yes |
| CGCCACTTGGTTGTCTTATGATGGCTTCAGTTTCCGAGGGGGTGAGAGG | R3-4908 | 258 | Yes |
| TGTACTATTGACGGTTGGTAACCCGAGGGTTTTTCTGCATGGGGGATGGG | R3-3936 | 259 | Yes |
| GTCCCTCGTTTTCTTGTACTCTTTACTCCCCCCCAACCCGCTGTTCTGTG | R3-1431 | 260 | Yes |
| AAATGGTGGTGGAGGAACAAAGTATAAGCCTAAGGGGAGGGTTGGCCATG | R3-5694 | 261 | Yes |
| GGTCTGTCACTCTTTCCCTCGCTTGCCCATGTCCCCATCCCCTAGGCCA | R3-4496 | 262 | Yes |
| TTGGGGGTCCGTTAATGGGATGCTGTTATCTACGTGCGCGGCGTAGGGGGG | R3-3024 | 263 | Yes |
| GAATACTTCTGCGGGGTGGCAGCGGGGTCGTGGGCAACATTTTCACTACG | R3-1555 | 264 | Yes |
| CTGCTTTTGGCGTTCGATCGTGTCCCTGGTTTGTGTCCATGGGTGGGTG | R3-3284 | 265 | Yes |
| ACAAGGTTGTCCCGTGGGAGAACCTAGGTCAAACCCTATGTGGGTGGGTA | R3-3368 | 266 | Yes |
| ACTTCATAGTCACATTAGAGGGGGGGTATGTCACCGTCTGTTTTTGCTA | R3-602 | 267 | Yes |
| CGGTATGTTGCCCAAGTATTTCTAGAAGGGGTTGGTAGTGGGCGGTCTTG | R3-4026 | 268 | Yes |
| GCATCGGGGGCGCGCATGGGGGGGGACACCTTGTTGTCGGGGAGACCCACT | R3-2034 | 269 | Yes |
| CATGTCGAAACAATCTTGGGCCGGGGGGGGTCCATCCTAAAAAGGTGAG | R3-715 | 270 | Yes |
| CAGCTGGACAACAGAGAGGCGATGAACTCAATCTCGGGGGGGTCATTTGG | R3-418 | 271 | Yes |
| TGGGTACCGTCGAACACCCCATTGCTGCAGTGTCGGGGCATGGGTGGCAA | R3-499 | 272 | Yes |
| GTGCCTCGCTTGCAGGTTAGGGGGGGTTGGGGATTGACCCTTATACAGCGT | R3-5932 | 273 | Yes |
| GTCAAGTATTCAAGTTCGGCCAGGGGGGGTTCCGGGACAAGGATAGGGGG | R3-2634 | 274 | Yes |
| AACATTGCTGGATATAGCATGCTGGGAGGGTGGTGTCGACGGGGATTGTA | R3-3672 | 275 | Yes |
| TAAGTGTCGGGGTCTGTCCATATTGTAGGGCATGGGGTGTGTCGGGAGCG | R3-1218 | 276 | Yes |
| CTGCTTTTGGCGTTCGATCGTGTTTCTGGTTTGTGTCCATGGGTGGGTG | R3-3172 | 277 | Yes |
| CGCCACTTGGTTGTCTTATGATGGCTTTAGTCTCCGAGGGGGTGAGAGG | R3-2255 | 278 | Yes |
| GGTCTGTCACTCTTTCTCTCGCCTGCCCATGTCCCCATCCCCCTAGGCCA | R3-3966 | 279 | Yes |
| GTGTCTCGCTTGCAGGTTAGGGGGTCGGGGATTGACCCTTATACAGCGT | R3-5198 | 280 | Yes |
| ACGACCATCGGAACGGCTGGTTCGGGTCATGGTCCTGGTAGGGGGTCATC | R3-3611 | 281 | Yes |
| GTTCCTAGGCCCTGGTTTCATGGTGCCCTCTCGCATGAGCCGGTAGGGGT | R3-972 | 282 | Yes |
| AACCCACCTTACAGGGCAATTGACTCCGGACCGTCGGGGTGCTCTGACG | R3-3704 | 283 | Yes |
| GTCGAACGCTCCCTTGATCTTGGTCAGCGAGTATACTAGCTGGGGGGGGC | R3-632 | 284 | Yes |
| GGTCCGTCACTCTTTCTCTCGCTTGCCCATGTCCCCATCCCCCTAGGCCA | R3-2518 | 285 | Yes |
| GTACTTCTCTGTTTTTTGCTTGGGTAGTGTGGGGTACCATATAGGGTCG | R3-656 | 286 | Yes |
| TAAGTGTCGGGGTCTGTCCATATTGTAAGCGTGGGGTGTGTCGGGAGCG | R3-728 | 287 | Yes |
| TGTCATTTGTGCGGTGAGGTGGGTCCGGCTGGTCCGGGCGGGCTTAAGGG | R3-4712 | 288 | Yes |
| CGCGAAGACATACGAGACGCGGTATCGGTTGGGGGGAGAAGACTTCAA | R3-357 | 289 | Yes |
| CAGCATGGGTCATTTCGAGCTTGATAATGTCTATGGCGGGGCGTTGCGGG | R3-50 | 290 | Yes |
| GTGTCTCGCTTGCAGGTTAGGGGGTTGGGGATTGACCCTTATACAGCGT | R3-205 | 291 | Yes |
| TGTACTATTGACGGTTGGTAAACCCGAGGGTTTTTCTGCATGGGGGTGG | R3-1152 | 292 | Yes |
| AATCTAACTGCGATACACCTCTTGTGTTCGGGGGGTTGGGTAAGGCCCCA | R3-1252 | 293 | Yes |
| GGTCTGTCACTCCTTCTCTCGCTTGCCCATGTCCCCATCCCCCTAGGCCA | R3-2080 | 294 | Yes |

TABLE 1-continued

SEQ ID Numbers and Aptamer Sequences Used in Affinity Precipitation Studies

| Sequence | Name | SEQ ID NO: | Used in affinity chromatography column? |
|---|---|---|---|
| CGTCCTACCGTTACTTGAATCCCTTCCTAGTCGTTAGCTTACCCCCTATG | R3-4926 | 295 | Yes |
| TAAGTGTCGGGGTCTGTCCATATTGTGAGGCATGGGGTGTGTCGGGAGCG | R3-4371 | 296 | Yes |
| TGCGTTGCCGGTATAGGTAGAGCTGTACTGTGCGGGAGTATGGTGGGGGC | R3-5456 | 297 | Yes |
| CGCGAAGTGACATACAAGACGCGGTATCGGTTGGGGGGAGAAGACTTCAA | R3-2837 | 298 | Yes |
| AACAATGCTGGATATAGCATGCTGGGAGGGTGGCGTCGACGGGGATTGTA | R3-4260 | 299 | Yes |
| ATTTGTTACTACTCTAGCGGCATCATGTTGCAGGACACGATGGTGGGGGA | R3-5347 | 300 | Yes |
| CTGCTTTTGGCGTTCGGTCGTGTTCCTGGTTTGTGTCCATGGGGTGGGTG | R3-4162 | 301 | Yes |
| TTGACGTTTTCCTCTGGGATAAGGGTTGGGGGAGGTGTGGGCACTGCGAG | R3-3092 | 302 | Yes |
| ACCTGTGGCTGTTCCTTAAAGATATATACGGTCGGGGGTTTCCACGGGGC | R3-1382 | 303 | Yes |
| TCTCAGGGGGGGGGGAGCAGCTTTTCTTTTCTTCCGACGTGCAGGGCCGC | R3-5352 | 304 | Yes |
| GGGATTTCGATACATCGTTGCTGGGTAATAAAGGAGGCGAGAAGGGGGTG | R3-3073 | 305 | Yes |
| CGCCACTTGGTTGTCTTATGATGGCTTTAGTTTCCGAGGGGGCGAGAGG | R3-3273 | 306 | Yes |
| AACAATGCTGGATATAGCATGCTGGGAGGGTGGTGTCGACGGGGATTGTG | R3-5119 | 307 | Yes |
| CATGTTTACTACGCCATTGGGGCCCAGTGGCGCGGCGGGTGGACTCGGTA | R3-624 | 308 | Yes |
| TACCTACTCCGTAACTACACTGGGTGTGACTGGGGGGATTGGTCTATGTC | R3-2388 | 309 | Yes |
| GTGTCTCGCCTGCAGGTTAGGGGGGTTGGGGATTGACCCTTATACAGCGT | R3-3909 | 310 | Yes |
| GTATATCTCTCAGTGTCCGCCGGTTACGGGGCCCAAACCGAGTGGGGGG | R3-4758 | 311 | Yes |
| CGGAGAGACAGGCTGGTTCGTTTCGGTCGGTGGGGGAGTTTTATGAGTTG | R3-5612 | 312 | Yes |
| CAGCATGGGTCATTTCGAGCTTGATAATGTCTACGGCGGGGCGTTGCGGG | R3-5611 | 313 | Yes |
| GGATAATTGCTCACATTCGTTGGGAGGGGGAGTGGTGTGTTTAACCGAC | R3-4650 | 314 | Yes |
| CGGTTTCGTTTTCAGTGGGGGTATCGTTTCTATGTTAGTTTCGGGGTTGT | R3-3821 | 315 | Yes |
| GTGTCCCGCTTGCAGGTTAGGGGGGTTGGGGATTGACCCTTATACAGCGT | R3-2220 | 316 | Yes |
| GCTGTTATTCCTTACACGTGACACGTTTGGGGTCTTGCGACCTGGGGGTG | R3-4525 | 317 | Yes |
| CCGGGAGAAAAGCTGGTACGTTACTCGTTTGGTGTGGGGGCTACAAGGGC | R3-543 | 318 | Yes |
| TGTACTATTGACGGTTGGTAAACCCGAGGGTTCTTCTGCATGGGGGATGG | R3-4059 | 319 | Yes |
| CGCCACTTGGTCGTCTTATGATGGCTTTAGTTTCCGAGGGGGTGAGAGG | R3-2694 | 320 | Yes |
| ATAAGTCTCCCCAGCGATGTTGAATTCAGCTCAGGGGAGGGCACGGGTGT | R3-816 | 321 | Yes |
| AGAATACGAATGTTACTAGGGGTGGGCAATACTAGGGCATATTGAGTAGT | R3-330 | 322 | Yes |
| GGCCCCACGAGTGTTAGGGGAAAAGTGGTGGGGTAGTATCTGGGTCGGCT | R3-4163 | 323 | Yes |
| CGCCACTTGGTTGTCTTATGATGGCTTTAGTTTCCGAGGGGGTGAGAGGG | R3-1373 | 324 | Yes |
| CGCCGCTTGGTTGTCTTATGATGGCTTTAGTTTCCGAGGGGGTGAGAGG | R3-3699 | 325 | Yes |
| GGTCTGTCACTCTTTCTCTCGCTTGCCCATGTCCCCATCCCCCTGGGCCA | R3-2124 | 326 | Yes |
| GGTCTGTCACTCTTCCTCTCGCTTGCCCATGTCCCCATCCCCCTAGGCCA | R3-5387 | 327 | Yes |
| GTCACCGTACTTTTCTCGCCCTCTCTCATCCGTATGCTCTTGGGG | R3-1206 | 328 | Yes |
| GCTGTTATTCTTTACGCGTGACACGTTTGGGGTCTTGCGACCTGGGGGTG | R3-4022 | 329 | Yes |
| AAACGAAGCAAGCTCGAGCCCATGCCACCGGTGGCCCTTGCTTGGGGGTG | R3-4345 | 330 | Yes |
| CTTTCTAGTCAAGGAATGAACTGCTTTGGGGTTGTAGGGGTAAGTGTCGG | R3-5232 | 331 | Yes |
| GGTCTGTCACTCTTTCTCGCTTGCCCGTGTCCCCATCCCCCTAGGCCA | R3-5332 | 332 | Yes |
| GGATACTGGTAGGGGGAAGTTTTGTGGAATCGTGGAGCAGTGGGGGTTGG | R3-2524 | 333 | Yes |
| CTTTCTAGTCAAGGAATGAACTGCTTTAGGGTTGTGGGGGTAAGTGTCGG | R3-2493 | 334 | Yes |
| CAGTTGCTTTGTGGGGGCCATCTTGCTGTGGTTGTGGGTTTATGGGGCA | R3-3359 | 335 | Yes |
| CAGTTGCTTTGTGGGGGTCATCTTGCTGTGGTTGTGGGTTTATGGGGCAG | R3-802 | 336 | Yes |
| CTGGAATTAAACAATCTCGCCGGGGGGGGGACCTAAGCACTGTGATCG | R3-5665 | 337 | Yes |
| CAGCATGGGTCATTTCGAGCCTGATAATGTCTATGGCGGGGCGTTGCGGG | R3-3500 | 338 | Yes |
| GCCTCAGGAAGGTCGGGCTTGGGATAGTGGGGTAGCTATATACGGGGTAG | R3-4503 | 339 | Yes |
| CTGACGTATTAGGTGGGAACACCAATGACATAGTAGGGCTGCGGGGGTAG | R3-4942 | 340 | Yes |
| TCAGCAGCGACTATTTGGGTCCAAGCCGGCCATGGGCTGTGGGTCGCCG | R3-1498 | 341 | Yes |
| GGTGTTATTCTTTACACGTGACACGTTTGGGGTCTTGCGACCTGGGGGTG | R3-5183 | 342 | Yes |
| CAGTTGCTTTGTGGGGGTCATCTTGCTGTGGTTGTGGGCTTATGGGGCA | R3-3883 | 343 | Yes |
| CTTTCTCACATATGCGGGGTTGCATCTCAGGGAGCGGGGATCTAAGGGTA | R3-3701 | 344 | Yes |
| CAGCATGGGTCATTTCGGGCTTGATAATGTCTATGGCGGGGCGTTGCGGG | R3-4875 | 345 | Yes |
| TTCGTGCAGCGTTCATCACAGAATAGTGGGTTGGGGGATCGTAGTAACAG | R3-637 | 346 | Yes |
| GCCTCAGGAAGGTCGGGCTTAGGATAGTGGGGTGGCTATATACGGGGTAG | R3-3288 | 347 | Yes |
| CAGTTGCTTTGTGGGGGTCATCTTGCTGTGGTTGTGGGTTTATGGGGGCG | R3-3566 | 348 | Yes |
| TAAGCGTCGGGGTCTGTCCATATTGTAAGGCATGGGGTGTGTCGGGAGCG | R3-2790 | 349 | Yes |
| CCCAGTCTGTAGCGTAATCTCTGCGCAAACCTCGAGAACCGGGGGGTAGG | R3-5507 | 350 | Yes |
| GCGTCTCGCTTGCAGGTTAGGGGGGTTGGGGATTGACCCTTATACAGCGT | R3-4419 | 351 | Yes |
| GTATATCTCTCAGTGTCCGCCGGTTACGGGGCCCAAACCAAGTGGGGGGA | R3-2571 | 352 | Yes |
| CGGTATGTTGTCCAAGTATTTCTAGAAGGGGTTGGTAGTGGGGGTCTTTG | R3-304 | 353 | Yes |
| CCTTCTCCCGCATTTCCTTTTTTCCCGCTTATATGCCCTTACGTTTGGAC | R3-5553 | 354 | Yes |
| ACGACCGTCGGAACGGCTGGTTCGGGTCATGATCCTGGTAGGGGTCATC | R3-5244 | 355 | Yes |
| CAGCGACGAGTCCATTGTGGGACGTAGGGCGGGAGCTTTTAGTTGTTCG | R3-1018 | 356 | Yes |
| TATCATATCCCTGGCCTTCGAGGGTCTACTTAGGCGGGGGTCCAATGGCC | R3-4246 | 357 | Yes |
| AATGGGCACAGACTACGGAGCGGAAAGTAGCTGTCTGGTCGGGGGTCTG | R3-1931 | 358 | Yes |
| TGTACTATTGGCGGTTGGTAAACCCGAGGGTTTTTCTGCATGGGGGATGG | R3-3133 | 359 | Yes |
| GGTCTGTCACTCTTTCTCTCGCTTGCCCACGTCCCCATCCCCCTAGGCCA | R3-4813 | 360 | Yes |
| TTGACGTTTTCCTCTGGGATAAGGGTTGGGGAGATGTGGGCACTGCGAG | R3-3493 | 361 | Yes |
| CAGCATGGGTCATTTCGAGCTTGATAATGCCTATGGCGGGGCGTTGCGGG | R3-4021 | 362 | Yes |
| GGTCTGTCACTCTTTCTCCCGCTTGCCCATGTCCCCATCCCCCTAGGCCA | R3-1680 | 363 | Yes |
| GGCCCCACGAGTGCTAGGGGAAAAGTGGTGGGGTAGTATCTGGGCCGGCT | R3-4952 | 364 | Yes |
| TAAGTGTCGGGGTCTGTCCATATTGTAAGGCACGGGGTGTGTCGGGAGCG | R3-1325 | 365 | Yes |
| CCGCGTGTCGGGGGGCTATTCGGTATATATACACGTCTGCGTGGGTGTGGG | R3-3594 | 366 | Yes |

TABLE 1-continued

SEQ ID Numbers and Aptamer
Sequences Used in Affinity Precipitation Studies

| Sequence | Name | SEQ ID NO: | Used in affinity chromatography column? |
|---|---|---|---|
| CCTTCTCCCACATTTCCTTTTTTCCCGCTTATGTGCCCTTACGTTTGGAC | R3-727 | 367 | Yes |
| ACCGACCGCCTCGACTAAAAAAGTTGTAGGACTGGTGAGGGTTTGGGTGA | R3-2178 | 368 | Yes |
| CCAGTCTGCACATTACGGGGATACGGGCGGGGGATTTCGGAGTGCTTTTG | R3-5252 | 369 | Yes |
| TGTACTATTGACGGTCGGTAAACCCGAGGGTTTTTCTGCATGGGGGATGG | R3-4985 | 370 | Yes |
| GGGGTTAAGCTACTAGGGGGTCGTACGAATGGGGTTTTGTTGTCCTAGGT | R3-5219 | 371 | Yes |
| ATGCGTTAAATCGTTCCTCTGTAGTGTATTGGGTTTTGTGGTGGGTGCGG | R3-4465 | 372 | Yes |
| ACAACCCCGAGGTGCAACGACGAGTTAGGTATCCTAGGGGGGGCACACGT | R3-4636 | 373 | Yes |
| TCCCGCATTCCTCTCGCGTTCCTGCACCATGGGGGCGGACCCCATCTAC | R3-3879 | 374 | Yes |
| CAGTTGCTTTGCGGGGTCATCTTGCTGTGGTTGTGGGTTTATGGGGCA | R3-2335 | 375 | Yes |
| GCTGTTATTCTTTACACGTGACACGTTTGGGGTCTTGCGACCTGGGGGTG | R3-222 | 376 | Yes |
| GTCACCGTACTTTTGTCTTCTCGCCCTCTCTCATCCGTATGTTCTTGGGG | R3-2911 | 377 | Yes |
| TAAGTGTCGGGGTCTGTCCATATCGTAAGGCATGGGGTGTGTCGGGAGCG | R3-2340 | 378 | Yes |
| GGCCCCACGAGTGTTAGGGGAAAGGTGGTGGGGTAGTATCTGGGCCTGCT | R3-1196 | 379 | Yes |
| GTCACCGTACTTTCGTTTTCTCGCCCTCTCTCATCCGTATGTTCTTGGGG | R3-3145 | 380 | Yes |
| GTCAAGTATTCAAGTTCGACCAGGGGGGTTCCGGGACAAGGATAGGGGGG | R3-1035 | 381 | Yes |
| AATAGCCTAAAAATGGTGAGTTGCTATTAGGATTTAGGGGGGCCGAGCAC | R3-454 | 382 | Yes |
| CATGAGGTAAGATGGCGTCGGGGGGGGGAATCGGTCACCCGCACCTTCGC | R3-3613 | 383 | Yes |
| GCTGTTATTCTTTACACGTGACACATTTGGGGTCTTGCGACCTGGGGGTG | R3-2857 | 384 | Yes |
| GTCAAGTATTCAAGTTCGACCAGGGGGGGTTCCGGGACAAGGATAGGGGG | R3-5454 | 385 | Yes |
| CTGGTTTCAGGACCGACACGGTTCGCGTTGGGAGCGGGCGGTGAGGCTCG | R3-4285 | 386 | Yes |
| CTCAGACTCGTACACCACAATCAGGACTGCGGTTCGGGTGGCGTGG | R3-2479 | 387 | Yes |
| TCGATTCCGACGTGATCTGGGCTTATACCACTGGGGGGGAACACCGTGGG | R3-4927 | 388 | Yes |
| CAGCATGGGTCATTTCGAGCTTGATAATGTCTATGCGGGCGTTGCGGGG | R3-3299 | 389 | Yes |
| TCCCGCATTTCTCTCGCGTTCCTGCACCATGGGGGCGGGCCCCATCTAC | R3-3774 | 390 | Yes |
| TAAGTGTCGGGGTCTGTCTATATTGTAAGGCATGGGGTGTGTCGGGAGCG | R3-3483 | 391 | Yes |
| CCAGTCTGCACATTACGGGGATACGGGCAGGGGGTTTCGGAGTGCTTTTG | R3-4312 | 392 | Yes |
| GTCGAACGCTCCCTTGATCTTGGTCAGCGAGTATACTAGCTGGGGGGCG | R3-3961 | 393 | Yes |
| GTCACCGTACTTTTGTTTTCTCACCCTCTCTCATCCGTATGTTCTTGGGG | R3-4143 | 394 | Yes |
| CCGCGTTGTGCAATTTCACGGATGGCGTCACTGGGGGGGGTGGGGTTCCG | R3-3621 | 395 | Yes |
| GTGTTAGAGTTCCTTAGGGGGGGTTTCGTTTTTCGGTGGGGCTCGGGGTG | R3-730 | 396 | Yes |
| GCTTATTCGGCATGTATGATTGGGGGTGAGTTTGGGGGGGGTCACTTGTG | R3-1029 | 397 | Yes |
| GTGTTAGAGTTCCTTAGGGGGGGGTTTCGTTTTTCGGTGGGGCTCGGGGT | R3-413 | 398 | Yes |

What is claimed:

1. A method of removing host cell proteins (HCPs) from a recombinant protein preparation comprising:
   providing a pool of aptamers;
   exposing the recombinant protein preparation to the final pool of aptamers;
   allowing the final pool of aptamers to bind HCPs forming aptamer:HCP complexes; and
   separating the aptamer:HCP complexes from the recombinant protein preparation,
   wherein the pool of aptamers is prepared by a method comprising:
      providing a library of potential aptamers bound to a bead;
      exposing the library of potential aptamers to an HCP mixture comprising a plurality of HCPs;
      separating via microfluidic selection or particle display, a plurality of candidate aptamers from the library for the ability of each candidate aptamer to bind to its HCP target and optionally determining the identity of a plurality of candidate aptamers, each binding an HCP in a plurality of HCPs;
   wherein the method identifies a plurality of candidate aptamers that specifically bind to HCPs in the HCP mixture.

2. The method of claim 1, wherein the library of potential aptamers comprises at least about 10, at least about $10^2$, at least about $10^3$, at least about $10^4$, at least about $10^5$, at least about $10^6$, at least about 10', at least about $10^8$, at least about $10^9$, at least about $10^{10}$, or at least about $6 \times 10^{14}$ aptamers.

3. The method of claim 1, wherein selecting a plurality of candidate aptamers from the library of potential aptamers comprises displaying a library of potential aptamers on a solid support.

4. The method of claim 3, wherein each unit of the solid support displays multiple copies of the same aptamer.

5. The method of any one of claim 4, wherein the solid support and the aptamers form aptamer particles.

6. The method of claim 5, wherein fluorescence-activated cell sorting (FACS) is used to isolate aptamer particles with an ability to bind one of the HCPs in the HCP mixture.

7. The method of claim 1, wherein selecting a plurality of candidate aptamers from the library of potential aptamers comprises microfluidic selection.

8. The method of claim 1, wherein the binding affinity for the candidate aptamers to the target HCPs is determined by measuring KD or KA.

9. The method of claim 1, wherein the method generates at least about 10, about 20, about 200, about 300, about 400, about 500, about 600, about 700, about 800, about 900, about 1000, or about $6 \times 10^{14}$ aptamers that specifically bind their target HCPs.

* * * * *

SEQUENCE LISTING

<160> NUMBER OF SEQ ID NOS: 398

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
agcagcacag aggtcagatg                                                     20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
cctatgcgtg ctaccgtgaa                                                     20

<210> SEQ ID NO 3
<211> LENGTH: 70
<212> TYPE: DNA
<213> ORGANISM: Artificial Sequence

```
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(50)
<223> OTHER INFORMATION: a, c, t, g, unknown or other

<400> SEQUENCE: 3
nnnnnnnnnn nnnnnnnnnn nnnnnnnnnn nnnnnnnnnn nnnnnnnnnn cctatgcgtg      60
ctaccgtgaa                                                             70

<210> SEQ ID NO 4
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (11)..(60)
<223> OTHER INFORMATION: a, c, t, g, unknown or other

<400> SEQUENCE: 4
aggtcagatg nnnnnnnnnn nnnnnnnnnn nnnnnnnnnn nnnnnnnnnn nnnnnnnnnn      60
cctatgcgtg                                                             70

<210> SEQ ID NO 5
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
gttcattccg ccttctttgg tctaggtccg gaccaattgt tatttcgttc                  50

<210> SEQ ID NO 6
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
cgaaaacaag cttagcaggc cgtgcgtcgg cacggcgcga ttatcggcta                  50

<210> SEQ ID NO 7
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
cgaaaacaaa cttagcaggc cgtgcgtcgg cacggcgcga ttatcggcta                  50

<210> SEQ ID NO 8
<211> LENGTH: 50
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 8
ggaactggct tattgagtag gctaatcatt cacctgaaaa gggttggctc    50

<210> SEQ ID NO 9
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
caaggtgcgg tgtgggggggc cttacagact gtttaggctc cgtgactggc    50

<210> SEQ ID NO 10
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
tggtggggta ggatagtaag ctcgaataat aagctgggtg cgtggtgccg    50

<210> SEQ ID NO 11
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
gtacggtgat tgaaactgta cttgcagtcc tatatggagg tgggaaggtc    50

<210> SEQ ID NO 12
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
gtgtgtgggg gtattggttg agtatttgtg cctatggtcg gtcatcctgt    50

<210> SEQ ID NO 13
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
aggacgagga cctgacgttg aggacgtagt tttggtcggg gggggtaca    50

<210> SEQ ID NO 14
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide -continued

<400> SEQUENCE: 14
acgggatgga gtttgtgtgg ttcactcttt gtgaacagag ggtttgtgga            50

<210> SEQ ID NO 15
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
gggtgaatgc gttaggtacc aggacaatat gcccgtggag tttccagtgc            50

<210> SEQ ID NO 16
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
gaggtatggc actccgaacg tcggtgaccg aatgtgtggc tctgtggtgt            50

<210> SEQ ID NO 17
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
ccgcgtgtcg gggggctatt cggtatatat cacgtctgca tgggtgtggg            50

<210> SEQ ID NO 18
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
ccgcgtgtta caaggctctt gggtatatag catgtttgca tgggtgtggg            50

<210> SEQ ID NO 19
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
gtgttaagaa tggttttgga aattgggaaa gctggtcgat ttggccaggg            50

<210> SEQ ID NO 20
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
gtcagatggt gttatacccg ggggtttatt tagtccctat tggcggggtg    50

<210> SEQ ID NO 21
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
ggagtccgga ccttgctgcc tgggggtttt tgaatttgtt aactgctctg    50

<210> SEQ ID NO 22
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
gtaattcact gggcggtatt tgtgtttact tcggtttttg gtctggtcgg    50

<210> SEQ ID NO 23
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
gaacggatcc ctgtgacttc tgtcatggcg gtgaacggtg tactacgggg    50

<210> SEQ ID NO 24
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
gggttttggt gaggggggaaa tggagtggca tacgccagtt cactaggacc    50

<210> SEQ ID NO 25
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
cagttgcttt gtgggggtca tcttgctgtg gttgtgggtt tatgggggca    50

<210> SEQ ID NO 26
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26

```
gggggcttta tgcggtatat gtcactagtt tgttactatc ggttgggagg        50
```

<210> SEQ ID NO 27
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27

```
ttggggtgct aagtagattt ggaagtagtg tgcattacct gggtgtgctg        50
```

<210> SEQ ID NO 28
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28

```
gggggttagg tttctgtgta aggagggctg agacgtgctt gggtggccgg        50
```

<210> SEQ ID NO 29
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29

```
ggtagccctg gcgggagcta gaaaagtcac gtttacataa ggttaagcgg        50
```

<210> SEQ ID NO 30
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30

```
tgtactattg acggttggta aacccgaggg tttttctgca tgggggatgg        50
```

<210> SEQ ID NO 31
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31

```
aaaacactgg gcggtcggat aacggcactc aatttttatt tcggcagcgg        50
```

<210> SEQ ID NO 32
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
tgtcatttgt gcggtgaggt gggtccagct ggtccgggcg ggcttagggg        50

<210> SEQ ID NO 33
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
gggggttagt tctgggacgt tgcccctgtg agtaccatgg tggctatccg        50

<210> SEQ ID NO 34
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
gggggttagt tctgggacgc tgcccctgtg agtaccatgg tggctgtccg        50

<210> SEQ ID NO 35
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
gggggttagt tctgggacgc tgcccctgtg agtaccatgg tggctatccg        50

<210> SEQ ID NO 36
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
cgccactcgg ttgtcttatg atggctttag tttccgaggg gggtgagagg        50

<210> SEQ ID NO 37
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
cgggatgtgg ccctattgta cacaggtgtc gtcccgtcgt cgttggtatg        50

<210> SEQ ID NO 38
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
ccttcaacgt atccctgggg aagggtggtt atttggccta ggggggaggc        50

```
<210> SEQ ID NO 39
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
cgatcaaccc gactaatcaa gagggtcgtc ggttcgtcgt ggtaggaagg            50

<210> SEQ ID NO 40
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
ctagccttac acagcggaaa ctagtcactc caacaatcta cggcagcggg            50

<210> SEQ ID NO 41
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
agcgtcacag agaaggtcgg agtgcaagta gcagtatcat ggtattgagg            50

<210> SEQ ID NO 42
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
cgtttgccta tgctcgtcta ccgctcccat catttgccat ttctttctcg            50

<210> SEQ ID NO 43
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
cgtcctaccg ttacttgaat ccctccctag tcgttagctt accccctatg            50

<210> SEQ ID NO 44
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
caatgtgtcg ggggctcgac gaaggagttt tccgtacggt cgctactaag            50
```

<210> SEQ ID NO 45
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
gacccacctt acagggcaat tgactccaga ccgtcggggg tgctctgacg         50

<210> SEQ ID NO 46
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
ccctggcttg ggctaaaaga cgttactcga gcgtataggg ggtctgtacg         50

<210> SEQ ID NO 47
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
cactcgtcct ggggcttggt cccagccgca ctaacatcga agtctcgcgc         50

<210> SEQ ID NO 48
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
gaaatatctg gtgtctctta ctggggcgca aaaaaaacgg gggttacggg         50

<210> SEQ ID NO 49
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
cggtatgttg tccaagtatt tctagaaggg gttggtagtg ggcggtcttg         50

<210> SEQ ID NO 50
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
gccgatcttt atgccttctc cgcctgcatg agcacccgtc ttatggtacc         50

<210> SEQ ID NO 51
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
ggttctagaa atgccgattt gttgaccaca acgaacaaac ttaggccatc           50

<210> SEQ ID NO 52
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
catgcagtag tagccggcct ggtgcggagg aagtacacct agaggatgcg           50

<210> SEQ ID NO 53
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
ccagtgtgag tgtttgcgtc cggctccata gtaaacgatt aacgccgcct           50

<210> SEQ ID NO 54
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
ggcaccgggc cactccccgt taatgcaact aatccagtca cattgtcacg           50

<210> SEQ ID NO 55
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
ggccgtgaac aatctaccct ccaccacgcc ttctccttgt aaacagctcc           50

<210> SEQ ID NO 56
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
tcctgtctgg cttcccctttt ctcgtcgtca tttcacttgt gctcgatccg          50

<210> SEQ ID NO 57

<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57 tggaggggggg gattaatcta gcaagcgacg ggtgaacta                       39

<210> SEQ ID NO 58
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
tccaagttcg aattatcttg gcataccacc tatgctcatg taggacgggg            50

<210> SEQ ID NO 59
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
gggtagttag gacgtatgtg ttgttttccc tgtccaaagg atggccgcgc            50

<210> SEQ ID NO 60
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
cccgatgaag ttactaacgt gacagggttc cattgagctc gcgcccaagg            50

<210> SEQ ID NO 61
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
caggcaagtg aaggcctcat tttatgtgag acatattttc caggcagagg            50

<210> SEQ ID NO 62
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
ctagagtttc aaggctgtct gttatgtatc gggatgatta aggacgaggt            50

<210> SEQ ID NO 63
<211> LENGTH: 49

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
aagtacagtc ccatctagtc ggagtcatgg aacaatttga cttaccggg          49

<210> SEQ ID NO 64
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
ccggacgata caattcacct gttactgtgg attcgttaag cttagtcggt          50

<210> SEQ ID NO 65
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
ccggacgata caattcacct gttactgtgg agtcgttaag cttagtcggt          50

<210> SEQ ID NO 66
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
ccggacgata caatccatct gttactgtgg attcgttaag cttagtcggt          50

<210> SEQ ID NO 67
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
ccggacgata caatccacct gttactgtgg gttcgttaag cttagtcggt          50

<210> SEQ ID NO 68
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
ccggacgata caatccacct gttactgtgg attcgttaag cttagtcggt          50

<210> SEQ ID NO 69
<211> LENGTH: 50
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 69
ccggacgata caatccacct gttattgtgg attcgttaag cttagtcggt        50

<210> SEQ ID NO 70
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
ccggacgata caatccacct gttactgtgg attcgtcgag cttagtcggt        50

<210> SEQ ID NO 71
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
ccgggcgata caatccacct gttactgtgg attcgttaag cttagtcggt        50

<210> SEQ ID NO 72
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
ccggacgata caatccacct gttactgtgg atccgttaag cttagtcggt        50

<210> SEQ ID NO 73
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
tttttttttt tttttttttt tttttttttt tttttttttt tttttttttt        50

<210> SEQ ID NO 74
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
ggttctagaa atgccgattt gttgaccaca acaaacaaac ttaggccatc        50

<210> SEQ ID NO 75
<211> LENGTH: 50
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 75
ccgcgttgtg caatttcacg gatggcgtca ctggggggggg tggggttccg            50

<210> SEQ ID NO 76
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
gtgttagagt tccttagggg gggtttcgtt tttcggtggg gctcggggtg            50

<210> SEQ ID NO 77
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
gcttattcgg catgtatgat tgggggtgag tttggggggg gtcacttgtg            50

<210> SEQ ID NO 78
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
gtgttagagt tccttagggg ggggtttcgt ttttcggtgg ggctcggggt            50

<210> SEQ ID NO 79
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
gcttattcgg catgtatgat tgggggtgag tttggggggg gggtcacttg            50

<210> SEQ ID NO 80
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
gtgttagagt tccttagggg gggggtttcg tttttcggtg gggctcgggg            50

<210> SEQ ID NO 81
<211> LENGTH: 50
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 81
gtccgccagg taaaattgtt ggagattcgt gggtgggtat gggggatggg            50

<210> SEQ ID NO 82
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
cgcgcaagtt ccaatccgat agaaaggggg gagcgggggg tcgggatgag            50

<210> SEQ ID NO 83
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
gggtgtcact tcaaggggct aggttggtcg gttgttcggt gggggggcagg           50

<210> SEQ ID NO 84
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84
tgcccgtctg cttgggggta ttttcggggt gggcctttttg ttgttggcac           50

<210> SEQ ID NO 85
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
aggacgagga cctgacgttg aggacgtagt tttggtcggg ggggggtaca           50

<210> SEQ ID NO 86
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
ccttcaacgt atccctggga aagggtggtt atttggccta ggggggggggc           50

<210> SEQ ID NO 87
<211> LENGTH: 50
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 87
ggataattgc tcacattcgt tgggggggg gggagtggtg tgtttaaccg        50

<210> SEQ ID NO 88
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 88
cgcgcaagtt ccaatccgat agaaagaggg gagcgggggt cgggatgagg        50

<210> SEQ ID NO 89
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89
ggcaataaaa ggctgatcat tccagattac gtctcgtggg gggggtcgg        50

<210> SEQ ID NO 90
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90
gtccaccagg taaaattgtt ggagattcgt gggtgggtat ggggatgga        50

<210> SEQ ID NO 91
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
cgccacttgg ttgtcttacg atggctttag tttccgaggg gggtgagagg        50

<210> SEQ ID NO 92
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
ctcagactcg tacaccacaa tcaggactgc ggttcggggt ggcgtgggaa        50

<210> SEQ ID NO 93
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 93
atcatgggct acctcacaac gggtttatca tttctggggt ttgggggggcg            50

<210> SEQ ID NO 94
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 94
ctgcttttgg cgttcgatcg tgttcctggt ttgtgtccgt ggggtgggtg            50

<210> SEQ ID NO 95
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
tgaccgacac ttatgcgggt aagaagagta gcgcggggtg gggcatgccg            50

<210> SEQ ID NO 96
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 96
taagtgtcgg ggtctgtcca tattgtaagg catggggtgt gtcggggcg            50

<210> SEQ ID NO 97
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 97
ttgacgtttt cctctgggat aagggttggg ggggatgtgg gcactgcgag            50

<210> SEQ ID NO 98
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98
aatggggcac agactacgga gcggaaggta gctgtctggt cggggggtct            50

<210> SEQ ID NO 99
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 99
cagttgcttt gtgggggtcg tcttgctgtg gttgtgggtt tatgggggca        50

<210> SEQ ID NO 100
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
aatggggcac agactacgga gcggaaagta gctgtctggt cggggggtc         50

<210> SEQ ID NO 101
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101
tgaccaacgg ccattgactt actggtgccc aacatcccgg ggtaggggtg        50

<210> SEQ ID NO 102
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102
gctgttattc tttacacgtg acgcgtttgg ggtcttgcga cctggggtg         50

<210> SEQ ID NO 103
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103
cgctttctcc attagtggcc tcatgacggt aaggagtaga gggggaggtg        50

<210> SEQ ID NO 104
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104
gcttattcgg catgtatgat tgggggtgag tttgggggg ggtcacttgt         50

<210> SEQ ID NO 105
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
cgcgcaagtt ccaatccgat agaaagaggg gagcgggggg tcgggatgag        50

<210> SEQ ID NO 106
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106
gtgttagagt tccttagggg ggggtttcgt ttttcggtgg ggctcaggut        50

<210> SEQ ID NO 107
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107
gtccgccggg taaaattgtt ggagattcgt gggtgggtat gggggatgga        50

<210> SEQ ID NO 108
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 108
gtccaccagg taaaattgtt ggagattcgt gggtgggtat gggggatgga        50

<210> SEQ ID NO 109
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109
ggcaataaaa ggctgatcac tccagattac gtctcgtggg ggggtcggt         50

<210> SEQ ID NO 110
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 110
ggataattgc tcacattcgt tgggggggg ggagtggtgt gtttaaccga         50

<210> SEQ ID NO 111
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111
gtccgccagg taaaattgtt ggagattcgt gggtgggtat ggggatgga            50

<210> SEQ ID NO 112
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 112
aggacgagga cctgacgttg aggacgtagt tttggtcggg ggggtacag             50

<210> SEQ ID NO 113
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 113
ggcaataaaa ggctgatcat tccagattac gcctcgtggg ggggtcggt             50

<210> SEQ ID NO 114
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 114
ggataattgc tcacattcgt tggggggggg gagtggtgtg tttaaccgac            50

<210> SEQ ID NO 115
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 115
cgccacttgg ttgtcttatg atggctttag tttccgaggg gggtgggagg            50

<210> SEQ ID NO 116
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 116
cgccacttgg ttgtcttatg atggctttag tttccgaggg gggtgagggg            50

<210> SEQ ID NO 117
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 117
ggcaataaaa ggctgatcat tccagattac gtctcgtggg ggggtcggt             50

<210> SEQ ID NO 118
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 118
ccttcaacgt atccctggga aagggtggtt attcggccta gggggaggc          50

<210> SEQ ID NO 119
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 119
gatcacgctt gtcgctaggg gggtgcgggt gggaagccat tttcgtccca          50

<210> SEQ ID NO 120
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 120
tcccgtccga tagttggggt aggtgtatgc ggttgtttat ggggggggat          50

<210> SEQ ID NO 121
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 121
gtatatctct cagtgtccgc cggttacggg gcccgaacca agtgggggg          49

<210> SEQ ID NO 122
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 122
ggcaataaaa ggctgatcat tccggattac gtctcgtggg ggggtcggt          50

<210> SEQ ID NO 123
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123
ccttcaacgt accctggga aagggtggtt atttggccta gggggaggc           50

<210> SEQ ID NO 124
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 124
ccttcaacgt atccctggga aagggtggtt atttggtcta gggggaggc                50

<210> SEQ ID NO 125
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 125
ctgcttttgg cgttcgatcg tgttcctggt ttgtgtccac ggggtgggtg                50

<210> SEQ ID NO 126
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 126
ccttcaacgt atccctggga agggtggtt atttggccta gggggaggc                  50

<210> SEQ ID NO 127
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 127
ggcaataaaa ggctgatcat tccagattac gtctcgcggg ggggtcggt                 50

<210> SEQ ID NO 128
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 128
gtccgccagg taaaattgtt ggagattcgt gggagggtat gggggatgga                50

<210> SEQ ID NO 129
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 129
cgccacttgg ttgtcttatg atggctttag tttccggggg gggtgagagg                50

<210> SEQ ID NO 130
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 130
ctcagactcg tacaccacaa tcaggactgc ggttcggggt ggcgtggg                 48

<210> SEQ ID NO 131
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 131
ctgcttttgg cgttcgatcg cgttcctggt ttgtgtccat ggggtgggtg              50

<210> SEQ ID NO 132
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 132
ctgctttcgg cgttcgatcg tgttcctggt ttgtgtccat ggggtgggtg              50

<210> SEQ ID NO 133
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 133
ggataattgc tcacattcgt tgggggggggg gagtggtgcg tttaaccgac             50

<210> SEQ ID NO 134
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 134
ctgcttttgg cgttcgaccg tgttcctggt ttgtgtccat ggggtgggtg              50

<210> SEQ ID NO 135
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 135
ggtcctaaag gtcgagcgtt agaaacagcc tagagggggg gtgg                    44

<210> SEQ ID NO 136

<210> SEQ ID NO 136
<211> LENGTH: 50
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 136
ctgcttttgg cgctcgatcg tgttcctggt ttgtgtccat ggggtgggtg    50

<210> SEQ ID NO 137
<211> LENGTH: 50
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 137
cctccaacgt atccctggga aagggtggtt atttggccta gggggaggc    50

<210> SEQ ID NO 138
<211> LENGTH: 50
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 138
gcggcgtcgg tccagggggt agtagtactt acagggtgg gatgcttgtc    50

<210> SEQ ID NO 139
<211> LENGTH: 50
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 139
ccttcaacgt atccctggga aagggtggtc atttggccta gggggaggc    50

<210> SEQ ID NO 140
<211> LENGTH: 50
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 140
ctgcttttgg cgttcgatcg tgttcctggt ctgtgtccat ggggtgggtg    50

<210> SEQ ID NO 141
<211> LENGTH: 50
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 141
ctgcttttgg cgtccgatcg tgttcctggt ttgtgtccat ggggtgggtg    50

<210> SEQ ID NO 142
<211> LENGTH: 50

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 142
gtccctcgtt ttcttgtact accttactcc cccccaaccc gctgttctgt                50

<210> SEQ ID NO 143
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 143
ctgcttttgg cgttcgatcg tgttcccggt ttgtgtccat ggggtgggtg                50

<210> SEQ ID NO 144
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 144
ccgcttttgg cgttcgatcg tgttcctggt ttgtgtccat ggggtgggtg                50

<210> SEQ ID NO 145
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 145
ctgcttttgg cgttcgatcg tgttcctggt tcgtgtccat ggggtgggtg                50

<210> SEQ ID NO 146
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 146
ggataattgc tcacattcgt tggggggggg agtggtgtgt ttaaccgacg                50

<210> SEQ ID NO 147
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 147
ctgcttctgg cgttcgatcg tgttcctggt ttgtgtccat ggggtgggtg                50

<210> SEQ ID NO 148
<211> LENGTH: 50
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 148
ccttcagcgt atccctggga aagggtggtt atttggccta ggggggaggc        50

<210> SEQ ID NO 149
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 149
gggtcttatt ctggtattgt tagttatggg ggtgtcgtcg gcgggacctg        50

<210> SEQ ID NO 150
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 150
cagttgcttt gtgggggtca tcttgctgtg gttgtgggtc tatgggggca        50

<210> SEQ ID NO 151
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 151
gtgtctcgct tgcaggttag ggggggttgg ggattgaccc ttatacagcg        50

<210> SEQ ID NO 152
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 152
ctagcggggg gtttatctag atgtcgtggg ccctgggggg gcctgctacg        50

<210> SEQ ID NO 153
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 153
ccttcaacgc atccctggga aagggtggtt atttggccta ggggggaggc        50

<210> SEQ ID NO 154
<211> LENGTH: 50
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 154
tcccgtccga tagctggggt aggtgtatgc ggttatttat ggggggggat                50

<210> SEQ ID NO 155
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 155
cgccacttgg ttgtcttatg atggctttag tttccgaggg ggggtgagag                50

<210> SEQ ID NO 156
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 156
ggaaagttgt tgtccggcga agtctgaagg gtcgggtctg gggcattcgg                50

<210> SEQ ID NO 157
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 157
ccttcaacgt atccctggga aagggtggtt atttggccta gggggaggc                 50

<210> SEQ ID NO 158
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 158
gtccctcgtt ttcttgtgct actttactcc cccccaaccc gctgttctgt                50

<210> SEQ ID NO 159
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 159
cagttgcttt gtggggtca tcttgctgtg gttgtgggtt tgtgggggca                 50

<210> SEQ ID NO 160
<211> LENGTH: 50
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 160
ctgcttttgg cgttcgatcg tgttcctggt ttgtgtccat ggggcgggtg          50

<210> SEQ ID NO 161
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 161
ccctcaacgt atccctggga aagggtggtt atttggccta gggggaggc          50

<210> SEQ ID NO 162
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 162
ctgcttttgg cgttcgatcg tgttcctggt ttgtgtccat ggggtgggtg          50

<210> SEQ ID NO 163
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 163
ccttcaacgt atccctggga aagggtggtt atttggccta aggggaggc          50

<210> SEQ ID NO 164
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 164 gccctcgtt ttcttgtact actttactcc cccccaaccc gctgttctgt          50

<210> SEQ ID NO 165
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 165
ttaacattct ggattccctg tttcagccag caaagactgg gggggcaag          50

<210> SEQ ID NO 166
<211> LENGTH: 50
<212> TYPE: DNA
<213> ORGANISM: Artificial Sequence
<220> FEATURE:
<223> OTHER INFORMATION: Description of Artificial Sequence: Synthetic -continued oligonucleotide

<400> SEQUENCE: 166
gtccctcgtt ttcttgtact actttactcc ccccaaccc gctgttctgt        50

<210> SEQ ID NO 167
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 167
ctgctttggc gttcgatcgt gttcctggtt tgtgtccatg gggtgggtgg        50

<210> SEQ ID NO 168
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 168
ccggggtgca gcggccagta tatacgaaat ctcacagaag gggtgggggc        50

<210> SEQ ID NO 169
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 169
ccttcaacgt atccctggga gagggtggtt atttggccta ggggggaggc        50

<210> SEQ ID NO 170
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 170
acgtaaccat caccgggtgc ccctcgggg gggcagggta atgtcgcgcc        50

<210> SEQ ID NO 171
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 171
gaggcgggga tttagaaatg tgatcaacga accattccaa ggggtggggg        50

<210> SEQ ID NO 172
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 172
gttgcaattt ttctaccttg gaggcgccgt tcttgggggt cacgggtggc          50

<210> SEQ ID NO 173
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 173
ggcaataaaa ggctgatcat tccagattac gtctcgtggg ggggtcggtg          50

<210> SEQ ID NO 174
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 174
gtccctcgtt ttcttgtact actttactcc cccccaacc cgctgttctg           50

<210> SEQ ID NO 175
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 175
gtcccccgtt ttcttgtact actttactcc ccccaaccc gctgttctgt           50

<210> SEQ ID NO 176
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 176
ctgaaggacg tgcgccattg tttcagtggg gtcgggggat aaattctcgg          50

<210> SEQ ID NO 177
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 177
ctcagactcg tacaccacga tcaggactgc ggttcggggt ggcgtggg            48

<210> SEQ ID NO 178
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 178
aatacgtctg cgggaacgc tctgaatcca tggtgcttcg gcgggtggga        50

<210> SEQ ID NO 179
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 179
cgccacttgg ttgtcttatg atggctttag gttccgaggg gggtgagagg        50

<210> SEQ ID NO 180
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 180
cagttgcttt gtgggggtca tcttgctgtg gttgtgggtt tatgggggta        50

<210> SEQ ID NO 181
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 181
taggtcacaa gagctgatag ggcaatcgac ggggtgggtg agtataggca        50

<210> SEQ ID NO 182
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 182
agtgtgcttg tgagcccgtg aatatcgcgt aggggtggct tcggggccg        50

<210> SEQ ID NO 183
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 183
taccaaacga caggaatata aagggggat ggggtctact gggcgacgtg        50

<210> SEQ ID NO 184
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 184
cagttgctct gtgggggtca tcttgctgtg gttgtgggtt tatgggggca                50

<210> SEQ ID NO 185
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 185
ggccgcctcg aaggctcgtt aattgttggg accgggtggg ctattgttcg                50

<210> SEQ ID NO 186
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 186
cgccacttgg ttgtctcatg atggctttag tttccgaggg gggtgagagg                50

<210> SEQ ID NO 187
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 187
ctgcttttgg cgttcgatcg tgctcctggt ttgtgtccat ggggtgggtg                50

<210> SEQ ID NO 188
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 188
tttgtagaca ttgtggctgg tggggatggg gtttggctgt ggtggtagtt                50

<210> SEQ ID NO 189
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 189
aggacgagga cctgacgttg aggacgtagt tttggtcggg ggggtacagg                50

<210> SEQ ID NO 190
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 190
cgggggtcac cggtcatgga ttaaggcgta gttgatggta tggggtgggg                50

<210> SEQ ID NO 191
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 191
tcccgtccga tagctggggt aggtgtatgc ggttgtttat ggggggggatg              50

<210> SEQ ID NO 192
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 192
catgtcgaaa caatcttggg ccgggggggg ggtccatcct aaaaaggtga               50

<210> SEQ ID NO 193
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 193
cgccacttgg ttgtcttatg gtggctttag tttccgaggg gggtgagagg               50

<210> SEQ ID NO 194
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 194
tcccgtccga tagctggggt aggtgtatgc ggttgtttat gggggggggat              50

<210> SEQ ID NO 195
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 195
agttgccaat ggcggtcata caatggacct acgcgcgcgg atgggggggtc              50

<210> SEQ ID NO 196
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 196
gcaaggtatg gtgtgtgatg ggtgggggggt gcagagggtt cagggaggtg              50

<210> SEQ ID NO 197
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 197
cggagagaca ggctggttcg tttcggtcag tgggggggtt ttatgagttg             50

<210> SEQ ID NO 198
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 198
aacaatgctg gatatagcat gctgggaggg tggtgtcgac ggggggttgta            50

<210> SEQ ID NO 199
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 199
gtccctcgtt ttcttgtact actttacccc cccccaaccc gctgttctgt             50

<210> SEQ ID NO 200
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 200
ctgcttttgg cgttcgatcg tgttcctggc ttgtgtccat ggggtgggtg             50

<210> SEQ ID NO 201
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 201
cagttgcttt gtgggggtca tcttgctgtg gttgtgggtt tatgggggc              50

<210> SEQ ID NO 202
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 202
ctgcttttgg cgttcgatca tgttcctggt ttgtgtccat ggggtgggtg             50

<210> SEQ ID NO 203
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 203
cagttgcttt gtgggggtca tcttgctgtg gttgtgggtt atgggggcag         50

<210> SEQ ID NO 204
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 204
tcttggatca ccgtacatct ttgccattgc taccgccata ggggttcttg         50

<210> SEQ ID NO 205
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 205
aatggggcac agactacgga gcggaaagta gctgtctggt cgggggggtct        50

<210> SEQ ID NO 206
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 206
cgccacttgg ttgtcttatg atggccttag tttccgaggg gggtgagagg         50

<210> SEQ ID NO 207
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 207
gttaaagtga agtgcgagcg ttgtttagca ttgtcgggtg ggctatttgg         50

<210> SEQ ID NO 208
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 208
ctgctcttgg cgttcgatcg tgttcctggt ttgtgtccat ggggtgggtg         50

```
<210> SEQ ID NO 209
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 209
cagttgcttt gtgggggtca tcttgctgtg gctgtgggtt tatgggggca          50

<210> SEQ ID NO 210
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 210
gaaatatctg gtgtctctta ctggggcgca aaaaaacggg ggttacgggg          50

<210> SEQ ID NO 211
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 211
cagttgcttt gtgggggtca tcttgctgtg gttgtgggtt tatgggggca          50

<210> SEQ ID NO 212
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 212
cgccacttgg ttgtcttatg atggctttag ttcccgaggg gggtgagagg          50

<210> SEQ ID NO 213
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 213
gtgtctcgct tgcaggttag gggggttggg ggttgaccct tatacagcgt          50

<210> SEQ ID NO 214
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 214
tcagattgtc gacaaaccag tccggacgga tagggtgctc gggggctcgg          50

<210> SEQ ID NO 215
```

<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 215
tgtcatttgt gcggtgaggt gggtccagct ggtccgggcg ggcttaaggg                 50

<210> SEQ ID NO 216
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 216
aatggggcac agactacgga gcggaaagta gccgtctggt cgggggggtct                50

<210> SEQ ID NO 217
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 217
cagctggaca acagagaggc gatgaactca atctcggggg gggtcatttg                 50

<210> SEQ ID NO 218
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 218
cagttgcctt gtgggggtca tcttgctgtg gttgtgggtt tatgggggca                 50

<210> SEQ ID NO 219
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 219
ggcatatact ggtgcgatcc gaatgccggc cggtcccata ggcgggggt                  50

<210> SEQ ID NO 220
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 220
gtcaagtatt caagttcgac caggggggggt tccgggacag ggatagggggg               50

<210> SEQ ID NO 221
<211> LENGTH: 50

<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 221
tgtactattg acggttggta aacccggggg tttttctgca tgggggatgg          50

<210> SEQ ID NO 222
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 222
cgccacttgg ttgtcttatg acggctttag tttccgaggg gggtgagagg          50

<210> SEQ ID NO 223
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 223
cagcatgggt catttcgagc ttgatagtgt ctatggcggg gcgttgcggg          50

<210> SEQ ID NO 224
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 224
ccttcaacgt atccctgggg aagggtggtt atttggccta ggggggaggc          50

<210> SEQ ID NO 225
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 225
tgggggcgaa tacatgatgg gtttctaatg tagaggcaga ggggggagac          50

<210> SEQ ID NO 226
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 226
acgggagttt accatggggg cttgttaggg gggtagatat gtatcagata          50

<210> SEQ ID NO 227
<211> LENGTH: 50
<212> TYPE: DNA

```
<213> ORGANISM: Artificial Sequence
<220> FEATURE:
<223> OTHER INFORMATION: Description of Artificial Sequence: Synthetic
      oligonucleotide

<400> SEQUENCE: 227
cgccacttgg ttgccttatg atggctttag tttccgaggg gggtgagagg            50

<210> SEQ ID NO 228
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 228
aggatgttta gtcctagtgg gggggtctat ttcaacataa ggggtggtga            50

<210> SEQ ID NO 229
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 229
caccacttgg ttgtcttatg atggctttag tttccgaggg gggtgagagg            50

<210> SEQ ID NO 230
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 230
acaaccccga ggtgcaacga cgagttaggt atcctgggga gggcacacgt            50

<210> SEQ ID NO 231
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 231
ggataattgc tcacattcgt tggggggga gtggtgtgtt taaccgacg              49

<210> SEQ ID NO 232
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 232
ctgcctttgg cgttcgatcg tgttcctggt ttgtgtccat ggggtgggtg            50

<210> SEQ ID NO 233
<211> LENGTH: 50
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 233
aggaaagtaa cccggaacgt acttccgttt ctgggtgggg atgagcgacg              50

<210> SEQ ID NO 234
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 234
acttcatagt cacattagag ggggggggta tgtcaccgtc tgttttttgct             50

<210> SEQ ID NO 235
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 235
cagttgcttt gtgggggtca tcttgccgtg gttgtgggtt tatgggggca              50

<210> SEQ ID NO 236
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 236
aaggtcactg gctcataata ctgtgaaggg gtgctcaacg ggttgggtgc              50

<210> SEQ ID NO 237
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 237
cgccacttgg ttgtcttatg atggctttag tttccgaggg gggtgagagg              50

<210> SEQ ID NO 238
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 238
ctgcttttgg cgttcgattg tgttcctggt ttgtgtccat ggggtgggtg              50

<210> SEQ ID NO 239
<211> LENGTH: 50
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 239
tcagcagcga ctatttgggg ccaagccggc catgagctgt ggggtcgccg                    50

<210> SEQ ID NO 240
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 240
cgccacttgg ctgtcttatg atggctttag tttccgaggg gggtgagagg                    50

<210> SEQ ID NO 241
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 241
cggcaaggca tatgatccgt cgactcgata tacacttccc ggggtggcgg                    50

<210> SEQ ID NO 242
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 242
cgccacttgg ttgtcttatg atggctttag cttccgaggg gggtgagagg                    50

<210> SEQ ID NO 243
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 243
tagcaggttt aggccagcgc actactacac caaggatggg ggggatgctg                    50

<210> SEQ ID NO 244
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 244
acgggagttt accgtggggg cttgttaggg gggtagatat gtatcagata                    50

<210> SEQ ID NO 245
<211> LENGTH: 50
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 245
cgccacttgg ttgtcctatg atggctttag tttccgaggg gggtgagagg      50

<210> SEQ ID NO 246
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 246
ccttcaacgt atccctggga aagggtggtt atttggccta ggggaggcg      50

<210> SEQ ID NO 247
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 247
ggtctgtcac tctttctctc gcttgcccat gtccccaccc ccctaggcca      50

<210> SEQ ID NO 248
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 248
cagtcgcttt gtgggggtca tcttgctgtg gttgtgggtt tatgggggca      50

<210> SEQ ID NO 249
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 249
cagttgcttt gtgggggtca tcctgctgtg gttgtgggtt tatgggggca      50

<210> SEQ ID NO 250
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 250
tgtactattg acggttggta aacccgaggg tttttctgcg tgggggatgg      50

<210> SEQ ID NO 251
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 251
ggtctgtcac tctttctctc gcttgcccat gtccccgtcc ccctaggcca                50

<210> SEQ ID NO 252
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 252 gctttttaa cctgggggcc catgctggga gtggggattt gtaggggatg                 50

<210> SEQ ID NO 253
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 253
gtgtcggatc cgaggagcgc tcggctattg cgcggggag gttgtctgga                  50

<210> SEQ ID NO 254
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 254
cgcgaagtga catacgagac gcggtatcgg ttgggggag aagacttcga                  50

<210> SEQ ID NO 255
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 255
cgccactcgg ttgtcttatg atggctttag tttccgaggg gggtgagagg                 50

<210> SEQ ID NO 256
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 256
acactaccaa ctgcctacca tcacaccaca cgttttcaa aaacttcgca                  50

<210> SEQ ID NO 257
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 257
aacaatgctg gatatagcat gctgggaggg tggtgtcgac ggggattgta            50

<210> SEQ ID NO 258
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 258
cgccacttgg ttgtcttatg atggcttcag tttccgaggg gggtgagagg            50

<210> SEQ ID NO 259
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 259
tgtactattg acggttggta acccgagggt ttttctgcat ggggatggg             50

<210> SEQ ID NO 260
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 260
gtccctcgtt ttcttgtact actttactcc ccccaacccg ctgttctgtg            50

<210> SEQ ID NO 261
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 261
aaatggtggt ggaggaacaa agtataagcc taaggggagg gttggccatg            50

<210> SEQ ID NO 262
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 262
ggtctgtcac tctttccctc gcttgcccat gtccccatcc ccctaggcca            50

<210> SEQ ID NO 263
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 263
ttgggggtcc gttaatggga tgctgttatc tacgtcgcgg cgtagggggg          50

<210> SEQ ID NO 264
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 264
gaatacttct gcggggtggc agcggggtcg tgggcaacat tttcactacg          50

<210> SEQ ID NO 265
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 265
ctgcttttgg cgttcgatcg tgtccctggt ttgtgtccat ggggtgggtg          50

<210> SEQ ID NO 266
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 266
acaaggttgt cccgtgggag aacctaggtc aaaccctatg tgggtgggta          50

<210> SEQ ID NO 267
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 267
acttcatagt cacattagag ggggggtat gtcaccgtct gttttttgcta          50

<210> SEQ ID NO 268
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 268
cggtatgttg cccaagtatt tctagaaggg gttggtagtg ggcggtcttg          50

<210> SEQ ID NO 269
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 269
gcatcggggg cgcgcatggg ggggacacct tgttgtcggg gagacccact            50

<210> SEQ ID NO 270
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 270
catgtcgaaa caatcttggg ccggggggg gtccatccta aaaaggtgag              50

<210> SEQ ID NO 271
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 271
cagctggaca acagagaggc gatgaactca atctcggggg ggtcatttgg            50

<210> SEQ ID NO 272
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 272
tgggtaccgt cgaacacccc attgctgcag tgtcggggca tgggtggcaa            50

<210> SEQ ID NO 273
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 273
gtgcctcgct tgcaggttag gggggttggg gattgacccct tatacagcgt            50

<210> SEQ ID NO 274
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 274
gtcaagtatt caagttcggc caggggggggt tccgggacaa ggataggggg            50

<210> SEQ ID NO 275
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 275
aacattgctg gatatagcat gctgggaggg tggtgtcgac ggggattgta            50

<210> SEQ ID NO 276
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 276
taagtgtcgg ggtctgtcca tattgtaggg catggggtgt gtcgggagcg          50

<210> SEQ ID NO 277
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 277
ctgcttttgg cgttcgatcg tgtttctggt ttgtgtccat ggggtgggtg          50

<210> SEQ ID NO 278
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 278
cgccacttgg ttgtcttatg atggctttag tctccgaggg gggtgagagg          50

<210> SEQ ID NO 279
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 279
ggtctgtcac tctttctctc gcctgcccat gtccccatcc ccctaggcca          50

<210> SEQ ID NO 280
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 280
gtgtctcgct tgcaggttag gggggtcggg gattgaccct tatacagcgt          50

<210> SEQ ID NO 281
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 281
acgaccatcg gaacggctgg ttcgggtcat ggtcctggta gggggtcatc          50

<210> SEQ ID NO 282
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 282
gttcctaggc cctggtttca tggtgccctc tcgcatgagc cggtaggggt          50

<210> SEQ ID NO 283
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 283
aacccacctt acagggcaat tgactccgga ccgtcggggg tgctctgacg          50

<210> SEQ ID NO 284
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 284
gtcgaacgct cccttgatct tggtcagcga gtatactagc tgggggggggc          50

<210> SEQ ID NO 285
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 285
ggtccgtcac tctttctctc gcttgcccat gtccccatcc ccctaggcca          50

<210> SEQ ID NO 286
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 286
gtacttctct gtttttttgct tgggtagtgt gggggtacca tatagggtcg          50

<210> SEQ ID NO 287
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 287
taagtgtcgg ggtctgtcca tattgtaagg cgtggggtgt gtcgggagcg          50

```
<210> SEQ ID NO 288
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 288
tgtcatttgt gcggtgaggt gggtccggct ggtccgggcg ggcttaaggg            50

<210> SEQ ID NO 289
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 289
cgcgaagtga catacgagac gcggtatcgg ttgggggag aagacttcaa             50

<210> SEQ ID NO 290
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 290
cagcatgggt catttcgagc ttgataatgt ctatggcggg gcgttgcggg            50

<210> SEQ ID NO 291
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 291
gtgtctcgct tgcaggttag gggggttggg gattgaccct tatacagcgt            50

<210> SEQ ID NO 292
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 292
tgtactattg acggttggta aacccgaggg ttttctgca tgggggtgg              50

<210> SEQ ID NO 293
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 293
aatctaactg cgatacacct cttgtgttcg gggggttggg taaggcccca            50

<210> SEQ ID NO 294
```

<210> SEQ ID NO 294
<211> LENGTH: 50
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 294
ggtctgtcac tccttctctc gcttgcccat gtccccatcc ccctaggcca            50

<210> SEQ ID NO 295
<211> LENGTH: 50
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 295
cgtcctaccg ttacttgaat cccttcctag tcgttagctt accccctatg            50

<210> SEQ ID NO 296
<211> LENGTH: 50
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 296
taagtgtcgg ggtctgtcca tattgtgagg catggggtgt gtcgggagcg            50

<210> SEQ ID NO 297
<211> LENGTH: 50
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 297
tgcgttgccg gtataggtag agctgtactg tgcgggagta tggtgggggc            50

<210> SEQ ID NO 298
<211> LENGTH: 50
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 298
cgcgaagtga catacaagac gcggtatcgg ttgggggag aagacttcaa             50

<210> SEQ ID NO 299
<211> LENGTH: 50
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 299
aacaatgctg gatatagcat gctgggaggg tggcgtcgac ggggattgta            50

<210> SEQ ID NO 300
<211> LENGTH: 50

<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 300
atttgttact actctagcgg catcatgttg caggacacga tggtggggga         50

<210> SEQ ID NO 301
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 301
ctgcttttgg cgttcggtcg tgttcctggt ttgtgtccat ggggtgggtg         50

<210> SEQ ID NO 302
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 302
ttgacgtttt cctctgggat aagggttggg ggaggtgtgg gcactgcgag         50

<210> SEQ ID NO 303
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 303
acctgtggct gttccttaaa gatatatacg gtcgggggtt ccacggggc          50

<210> SEQ ID NO 304
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 304
tctcaggggg gggggagcag cttttctttt cttccgacgt gcagggccgc         50

<210> SEQ ID NO 305
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 305
gggatttcga tacatcgttg ctgggtaata aggaggcga gaaggggtg           50

<210> SEQ ID NO 306
<211> LENGTH: 50
<212> TYPE: DNA

```
<213> ORGANISM: Artificial Sequence
<220> FEATURE:
<223> OTHER INFORMATION: Description of Artificial Sequence: Synthetic
      oligonucleotide

<400> SEQUENCE: 306
cgccacttgg ttgtcttatg atggctttag tttccgaggg gggcgagagg                 50

<210> SEQ ID NO 307
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 307
aacaatgctg gatatagcat gctgggaggg tggtgtcgac ggggattgtg                 50

<210> SEQ ID NO 308
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 308
catgtttact acgccattgg ggcccagtgg cgcggcgggt ggactcggta                 50

<210> SEQ ID NO 309
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 309
tacctactcc gtaactacac tgggtgtgac tgggggatt ggtctatgtc                  50

<210> SEQ ID NO 310
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 310
gtgtctcgcc tgcaggttag gggggttggg gattgaccct tatacagcgt                 50

<210> SEQ ID NO 311
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 311
gtatatctct cagtgtccgc cggttacggg gcccaaaccg agtgggggg                  49

<210> SEQ ID NO 312
<211> LENGTH: 50
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 312
cggagagaca ggctggttcg tttcggtcgg tgggggagtt ttatgagttg         50

<210> SEQ ID NO 313
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 313
cagcatgggt catttcgagc ttgataatgt ctacggcggg gcgttgcggg         50

<210> SEQ ID NO 314
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 314
ggataattgc tcacattcgt tgggaggggg gagtggtgtg tttaaccgac         50

<210> SEQ ID NO 315
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 315
cggtttcgtt ttcagtgggg gtatcgtttc tatgttagtt tcggtggtgt         50

<210> SEQ ID NO 316
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 316
gtgtcccgct tgcaggttag gggggttggg gattgaccct tatacagcgt         50

<210> SEQ ID NO 317
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 317
gctgttattc cttacacgtg acacgtttgg ggtcttgcga cctggggtg         50

<210> SEQ ID NO 318
<211> LENGTH: 50
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 318
ccgggagaaa agctggtacg ttactcgttt ggtgtggggg ctacaagggc                 50

<210> SEQ ID NO 319
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 319
tgtactattg acggttggta aacccgaggg ttcttctgca tgggggatgg                 50

<210> SEQ ID NO 320
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 320
cgccacttgg tcgtcttatg atggctttag tttccgaggg gggtgagagg                 50

<210> SEQ ID NO 321
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 321
ataagtctcc ccagcgatgt tgaattcagc tcagggagg gcacgggtgt                  50

<210> SEQ ID NO 322
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 322
agaatacgaa tgttactagg ggtgggcaat actagggcat attgagtagt                 50

<210> SEQ ID NO 323
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 323
ggccccacga gtgttagggg aaaagtggtg gggtagtatc tgggtcggct                 50

<210> SEQ ID NO 324
<211> LENGTH: 50
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 324
cgccacttgg ttgtcttatg atggctttag tttccgaggg ggtgagaggg    50

<210> SEQ ID NO 325
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 325
cgccgcttgg ttgtcttatg atggctttag tttccgaggg gggtgagagg    50

<210> SEQ ID NO 326
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 326
ggtctgtcac tctttctctc gcttgcccat gtccccatcc ccctgggcca    50

<210> SEQ ID NO 327
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 327
ggtctgtcac tcttcctctc gcttgcccat gtccccatcc ccctaggcca    50

<210> SEQ ID NO 328
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 328
gtcaccgtac ttttgttttc tcgccctctc tcatccgtat gctcttgggg    50

<210> SEQ ID NO 329
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 329
gctgttattc tttacgcgtg acacgtttgg ggtcttgcga cctggggggtg    50

<210> SEQ ID NO 330
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 330
aaacgaagca agctcgagcc catgccaccg gtggcccttg cttgggggtg              50

<210> SEQ ID NO 331
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 331
ctttctagtc aaggaatgaa ctgctttggg gttgtagggg taagtgtcgg              50

<210> SEQ ID NO 332
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 332
ggtctgtcac tctttctctc gcttgcccgt gtccccatcc ccctaggcca              50

<210> SEQ ID NO 333
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 333
ggatactggt aggggaagt tttgtggaat cgtggagcag tgggggttgg               50

<210> SEQ ID NO 334
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 334
ctttctagtc aaggaatgaa ctgctttagg gttgtggggg taagtgtcgg              50

<210> SEQ ID NO 335
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 335
cagttgcttt gtgggggcca tcttgctgtg gttgtgggtt tatgggggca              50

<210> SEQ ID NO 336
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 336
cagttgcttt gtgggggtca tcttgctgtg gttgtgggtt tatggggcag          50

<210> SEQ ID NO 337
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 337
ctggaattaa acaatctcgc cgggggggggg acctaagcac tgtgatcg           48

<210> SEQ ID NO 338
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 338
cagcatgggt catttcgagc ctgataatgt ctatggcggg gcgttgcggg          50

<210> SEQ ID NO 339
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 339
gcctcaggaa ggtcgggctt gggatagtgg ggtagctata tacggggtag          50

<210> SEQ ID NO 340
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 340
ctgacgtatt aggtggggaa caccaatgac atagtagggc tgcggggtg           50

<210> SEQ ID NO 341
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 341
tcagcagcga ctatttgggt ccaagccggc catgggctgt ggggtcgccg          50

<210> SEQ ID NO 342
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 342
```
ggtgttattc tttacacgtg acacgtttgg ggtcttgcga cctgggggtg         50

<210> SEQ ID NO 343
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 343
cagttgcttt gtgggggtca tcttgctgtg gttgtgggct tatgggggca         50

<210> SEQ ID NO 344
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 344
ctttctcaca tatgcggggt tgcatctcag ggagcgggga tctaagggta         50

<210> SEQ ID NO 345
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 345
cagcatgggt catttcgggc ttgataatgt ctatggcggg gcgttgcggg         50

<210> SEQ ID NO 346
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 346
ttcgtgcagc gttcatcaca gaatagtggg ttgggggatc gtagtaacag         50

<210> SEQ ID NO 347
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 347
gcctcaggaa ggtcgggctt aggatagtgg ggtggctata tacggggtag         50

<210> SEQ ID NO 348
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 348

```
<210> SEQ ID NO 349
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 349
taagcgtcgg ggtctgtcca tattgtaagg catggggtgt gtcgggagcg            50

<210> SEQ ID NO 350
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 350
cccagtctgt agcgtaatct ctgcgcaaac ctcgagaacc gggggggtagg           50

<210> SEQ ID NO 351
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 351
gcgtctcgct tgcaggttag gggggttggg gattgaccct tatacagcgt            50

<210> SEQ ID NO 352
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 352
gtatatctct cagtgtccgc cggttacggg gcccaaacca agtgggggga            50

<210> SEQ ID NO 353
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 353
cggtatgttg tccaagtatt tctagaaggg gttggtagtg ggcggtcttg            50

<210> SEQ ID NO 354
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 354
ccttctcccg catttccttt tttcccgctt atatgcccctt acgtttggac           50
```

(preceding line, continued from prior page:)
cagttgcttt gtgggggtca tcttgctgtg gttgtgggtt tatggggggcg            50

<210> SEQ ID NO 355
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 355
acgaccgtcg aacggctgg ttcgggtcat gatcctggta gggggtcatc                50

<210> SEQ ID NO 356
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 356
cagcgacgag tccattgtgg gacgtagggc ggggagcttt tagttgttcg                50

<210> SEQ ID NO 357
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 357
tatcatatcc ctggccttcg agggtctact taggcggggg tccaatggcc                50

<210> SEQ ID NO 358
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 358
aatggggcac agactacgga gcggaaagta gctgtctggt cggggtctg                 50

<210> SEQ ID NO 359
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 359
tgtactattg gcggttggta aacccgaggg tttttctgca tgggggatgg                50

<210> SEQ ID NO 360
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 360
ggtctgtcac tctttctctc gcttgcccac gtccccatcc ccctaggcca                50

<210> SEQ ID NO 361
<211> LENGTH: 50
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 361
ttgacgtttt cctctgggat aagggttggg ggagatgtgg gcactgcggg          50

<210> SEQ ID NO 362
<211> LENGTH: 50
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 362
cagcatgggt catttcgagc ttgataatgc ctatggcggg gcgttgcggg          50

<210> SEQ ID NO 363
<211> LENGTH: 50
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 363
ggtctgtcac tctttctccc gcttgcccat gtccccatcc ccctaggcca          50

<210> SEQ ID NO 364
<211> LENGTH: 50
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 364
ggccccacga gtgctagggg aaaagtggtg gggtagtatc tgggccggct          50

<210> SEQ ID NO 365
<211> LENGTH: 50
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 365
taagtgtcgg ggtctgtcca tattgtaagg cacggggtgt gtcgggagcg          50

<210> SEQ ID NO 366
<211> LENGTH: 50
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 366
ccgcgtgtcg gggggctatt cggtatatat cacgtctgcg tgggtgtggg          50

```
<210> SEQ ID NO 367
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 367
ccttctccca catttccttt tttcccgctt atgtgccctt acgtttggac            50

<210> SEQ ID NO 368
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 368
accgaccgcc tcgactaaaa aagttgtagg actggtgagg gtttgggtga            50

<210> SEQ ID NO 369
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 369
ccagtctgca cattacgggg atacgggcgg gggatttcgg agtgcttttg            50

<210> SEQ ID NO 370
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 370
tgtactattg acggtcggta aacccgaggg ttttctgca tgggggatgg             50

<210> SEQ ID NO 371
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 371
ggggttaagc tactaggggg tcgtacgaat ggggttttgt tgtcctaggt            50

<210> SEQ ID NO 372
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 372
atgcgttaaa tcgttcctct gtagtgtatt gggttttgtg gtgggtgcgg            50

<210> SEQ ID NO 373
```

```
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 373
acaaccccga ggtgcaacga cgagttaggt atcctagggg gggcacacgt            50

<210> SEQ ID NO 374
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 374
tcccgcattc ctctcgcgtt cctgcaccat ggggggcgga ccccatctac            50

<210> SEQ ID NO 375
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 375
cagttgcttt gcggggtca tcttgctgtg gttgtgggtt tatgggggca             50

<210> SEQ ID NO 376
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 376
gctgttattc tttacacgtg acacgtttgg ggtcttgcga cctggggtg             50

<210> SEQ ID NO 377
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 377
gtcaccgtac ttttgtcttc tcgccctctc tcatccgtat gttcttgggg            50

<210> SEQ ID NO 378
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 378
taagtgtcgg ggtctgtcca tatcgtaagg catggggtgt gtcgggagcg            50

<210> SEQ ID NO 379
<211> LENGTH: 50
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 379
ggccccacga gtgttagggg aaaggtggtg gggtagtatc tgggccggct                50

<210> SEQ ID NO 380
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 380
gtcaccgtac tttcgttttc tcgccctctc tcatccgtat gttcttgggg                50

<210> SEQ ID NO 381
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 381
gtcaagtatt caagttcgac caggggggtt ccgggacaag gataggggg                 50

<210> SEQ ID NO 382
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 382
aatagcctaa aaatggtgag ttgctattag gatttagggg ggccgagcac                50

<210> SEQ ID NO 383
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 383
catgaggtaa gatggcgtcg ggggggggaa tcggtcaccc gcaccttcgc                50

<210> SEQ ID NO 384
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 384
gctgttattc tttacacgtg acacatttgg ggtcttgcga cctgggggtg                50

<210> SEQ ID NO 385
<211> LENGTH: 50
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 385
gtcaagtatt caagttcgac caggggggt tccgggacaa ggataggggg        50

<210> SEQ ID NO 386
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 386
ctggtttcag gaccgacacg gttcgcgttg ggagcgggcg gtgaggctcg        50

<210> SEQ ID NO 387
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 387
ctcagactcg tacaccacaa tcaggactgc ggttcggggt ggcgtgg          47

<210> SEQ ID NO 388
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 388
tcgattccga cgtgatctgg gcttatacca ctgggggga acaccgtggg        50

<210> SEQ ID NO 389
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 389
cagcatgggt catttcgagc ttgataatgt ctatggcggg cgttgcgggg        50

<210> SEQ ID NO 390
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 390
tcccgcattt ctctcgcgtt cctgcaccat ggggggcggg ccccatctac        50

<210> SEQ ID NO 391
<211> LENGTH: 50
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 391
taagtgtcgg ggtctgtcta tattgtaagg catggggtgt gtcgggagcg                 50

<210> SEQ ID NO 392
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 392
ccagtctgca cattacgggg atacgggcag ggggtttcgg agtgcttttg                 50

<210> SEQ ID NO 393
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 393
gtcgaacgct cccttgatct tggtcagcga gtatactagc tggggggggcg                50

<210> SEQ ID NO 394
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 394
gtcaccgtac ttttgttttc tcaccctctc tcatccgtat gttcttgggg                 50

<210> SEQ ID NO 395
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 395
ccgcgttgtg caatttcacg gatggcgtca ctggggggggg tggggttccg                50

<210> SEQ ID NO 396
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 396
gtgttagagt tccttagggg gggtttcgtt tttcggtggg gctcggggtg                 50

<210> SEQ ID NO 397
<211> LENGTH: 50
<212> TYPE: DNA
<213> ORGANISM: Artificial Sequence
<220> FEATURE:
```

-continued

```
<223> OTHER INFORMATION: Description of Artificial Sequence: Synthetic
      oligonucleotide

<400> SEQUENCE: 397
gcttattcgg catgtatgat tgggggtgag tttggggggg gtcacttgtg                50

<210> SEQ ID NO 398
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 398
gtgttagagt tccttagggg ggggtttcgt ttttcggtgg ggctcggggt                50
```